(12) United States Patent
Khera et al.

(10) Patent No.: US 10,399,968 B2
(45) Date of Patent: Sep. 3, 2019

(54) HYDROXYALKYL THIADIAZOLE DERIVATIVES

(71) Applicant: Daiichi Sankyo Company, Limited, Chuo-ku, Tokyo (JP)

(72) Inventors: Manoj Kumar Khera, Haryana (IN); Tarun Mathur, Haryana (IN); Jitendra A. Sattigeri, Haryana (IN); Nobuhisa Masuda, Suginami-ku (JP); Tsuyoshi Soneda, Fujisawa (JP); Yoshiko Kagoshima, Edogawa-ku (JP); Toshiyuki Konosu, Kawaski (JP); Tetsuya Suzuki, Edogawa-ku (JP); Makoto Yamaoka, Hiratsuka (JP); Ryo Itooka, Hiratsuka (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/764,264

(22) PCT Filed: Sep. 28, 2016

(86) PCT No.: PCT/IB2016/055795
§ 371 (c)(1),
(2) Date: Mar. 28, 2018

(87) PCT Pub. No.: WO2017/056012
PCT Pub. Date: Apr. 6, 2017

(65) Prior Publication Data
US 2018/0327399 A1    Nov. 15, 2018

(30) Foreign Application Priority Data
Sep. 30, 2015  (IN) ............... 3119/DEL/2015

(51) Int. Cl.
C07D 417/14    (2006.01)
A61P 31/04    (2006.01)

(52) U.S. Cl.
CPC ............ C07D 417/14 (2013.01); A61P 31/04 (2018.01)

(58) Field of Classification Search
CPC ................................ C07D 417/14; A61P 31/04
USPC ........................................................ 546/209
See application file for complete search history.

(56) References Cited

FOREIGN PATENT DOCUMENTS

| EP | 2 226 322 A1 | 9/2010 | |
| JP | 2011-26305 A | 2/2011 | |
| WO | WO-2017056012 A1 * | 4/2017 | ........... C07D 417/14 |

OTHER PUBLICATIONS

Colombian Office Action dated Jul. 10, 2018, issued in corresponding Colombian Application No. NC2018/0003548, filed Sep. 28, 2016, 5 pages.

International Search Report and Written Opinion dated Dec. 21, 2016, issued in corresponding International Application No. PCT/IB2016/055795, filed Sep. 28, 2016, 8 pages.

* cited by examiner

*Primary Examiner* — Rita J Desai
(74) *Attorney, Agent, or Firm* — Christensen O'Connor Johnson Kindness PLLC

(57) ABSTRACT

Problem to be Solved
There is a need for a new antibiotic having a novel mechanism of action which exhibit strong antibacterial activity not only against sensitive bacteria but also against resistant bacteria thereof, and at the same time possesses excellent solubility an a safety profile amenable to human use.
Solution to the Problem
As a result of intensive research, the present inventors have found that a compound represented by general formula (I),

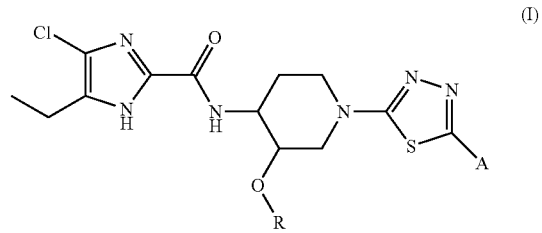

a stereoisomer, or a pharmaceutically acceptable salt thereof inhibits DNA gyrase GyrB subunit and/or topoisomerase IV ParE subunit possesses excellent solubility and a safety profile for use in humans for the treatment of bacterial infectious diseases.

23 Claims, 9 Drawing Sheets

HYDROXYALKYL THIADIAZOLE DERIVATIVES

FIELD OF THE INVENTION

The present invention provides a hydroxyalkyl thiadiazole compound, or a pharmaceutically acceptable salt thereof, having excellent antibacterial activity, and also being excellent in terms of safety. Furthermore, the present invention provides a pharmaceutical composition comprising a hydroxyalkyl thiadiazole compound, a polymorph, or a pharmaceutically acceptable salt thereof as a pharmaceutically active ingredient. Particularly, the present invention provides hydroxyalkyl thiadiazole compound, a polymorphic form, or a pharmaceutically acceptable salt thereof useful for treating and/or preventing infectious diseases.

BACKGROUND OF THE INVENTION

There are several Gram-positive species that cause diseases in human. The most common organisms include *Staphylococcus, Streptococcus, Enterococcus, Clostridium, Bacillus, Corynebacterium*, and *Listeria* species. Infections with common Gram-positive organisms have become more problematic to treat because of the growing trend of antibiotics drug-resistance.

Examples of such difficult-to-treat resistant bacteria include methicillin-resistant *Staphylococcus aureus* (MRSA), penicillin-resistant *Streptococcus pneumoniae* (PRSP), and vancomycin-resistant *Enterococcus* (VRE).

*Staphylococcus aureus* can cause a range of illnesses such as pimples, impetigo, boils, cellulitis folliculitis, furuncles, carbuncles, scalded skin syndrome, pneumonia, meningitis, osteomyelitis, endocarditis, toxic shock syndrome and sepsis. *S. aureus* is one of the most common causes of hospital-acquired infections. *Streptococcus pneumoniae* can cause many types of infections such as community acquired pneumonia, bronchitis, rhinitis, acute sinusitis, otitis media, conjunctivitis, meningitis, bacteremia, sepsis, osteomyelitis, septic arthritis, endocarditis, peritonitis, pericarditis, cellulitis, and brain abscess. *Enterococcus* can cause urinary tract infections, bacteremia, endocarditis, diverticulitis, and meningitis.

*Clostridium difficile* infection (CDI) is another problematic Gram-positive bacterial infection. CDI-related death has increased due to the spread of a hyper virulent NAP1/027 strain. Current treatments lead to more than 23% recurrence and have limitations against this virulent strain.

*Haemophilus influenzae*, a gram negative bacteria, can cause many kinds of infections including, but not limited to, ear infections, bacteremia, community-acquired respiratory infections, pneumonia and acute bacterial meningitis.

Treatment of bacterial infectious diseases is becoming more difficult and expensive due to developing resistance to existing antibiotics, spreading hypervirulent strains, and non-availability of more effacacious novel antibacterial agents.

In view of the above facts, the inventors of the present invention have realized that there should be a novel class of antibacterial agent having novel mechanism of action. After an exhaustive research, the inventors of the present invention have discovered novel compounds targeting the DNA gyrase GyrB subunit and/or topoisomerase IV ParE subunit, and hence are ready to meet the requirements of millions of patients worldwide.

In developing antibiotics having a novel mechanism of action, synthetic inhibitors targeting the DNA gyrase GyrB subunit are known in the art. For example, WO 2005/026149, WO 2006/087543, WO 2006/087544, WO 2006/087548, WO 2006/092599, WO 2006/092608, WO 2008/152418, WO 2008/020222, WO 2008/020227, WO 2008/020229, WO 2010/013222, WO 2010/067123, and WO 2010/067125 describe pyrrole derivatives having antibacterial activity. WO 2007/071965 describes bicyclic heteroaromatic compounds. WO 2014/57415 describes quinoline based compounds. These compounds had the problems of insufficient activity, low water solubility and toxicity. In addition, none of the cited references disclosed imidazole derivatives.

WO 2009/084614, incorporated herein by reference in its entirety, describes imidazole derivatives. The compounds disclosed in WO 2009/084614 have good properties, for example, sufficient in vitro antibacterial activity and no cytotoxicity. However, compound No. 150 having a thiadiazole substituent had a problem of not being efficacious in animal infection models, hence not suitable for use in human.

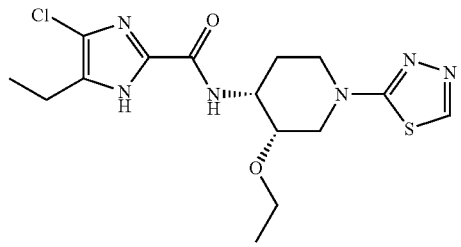 [SMILES: CCO[C@H]1CN(c2nncs2)CC[C@H]1NC(=O)c1nc(Cl)c(CC)[nH]1]

Compound No. 150 (WO 2009/084614)

In addition, the solubility is low compared to compounds disclosed hereinafter in this patent application for oral absorption.

Surprisingly, the hydroxyalkyl thiadiazole compounds of the present invention showed not only sufficient in vitro antibacterial activity, no cytotoxicity, good water solubility for oral absorption, but also remarkably good efficacy and safety, and hence are suitable for use in human.

Thus, the present invention provides great hope for a new antibiotic to meet the challenges of a serious global health concern due to problematic bacteria thereof causing bacterial infections, for example, but not limited to, community-acquired respiratory infections, hospital-acquired infections, urinary tract infections, and *Clostridium difficile* infections.

SUMMARY OF THE INVENTION

Problems to be Solved by the Invention

As realized by the inventors of the present invention, there is a need for a new antibiotic having a novel mechanism of action, which exhibits strong antibacterial activity not only against sensitive bacteria, but also against resistant bacteria thereof, and at the same time possess excellent solubility for oral absorption and safety profile amenable to human use.

Means for Solving the Problems

As a result of intensive studies, the present inventors have found that a compound represented by general formula (I), or a pharmaceutically acceptable salt thereof inhibits DNA gyrase GyrB subunit and/or topoisomerase IV ParE subunit. In particular, compounds of the present invention exhibit strong antibacterial activity, and possess excellent solubility and safety profile amenable to human use.

Thus, in one aspect, the present invention provides:

[1] A compound represented by general formula (I), or a pharmaceutically acceptable salt thereof;

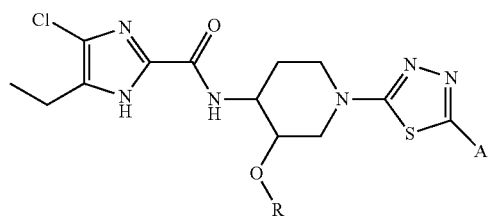
(I)

wherein R represents ($C_1$-$C_3$) alkyl, and
A represents following formulae:

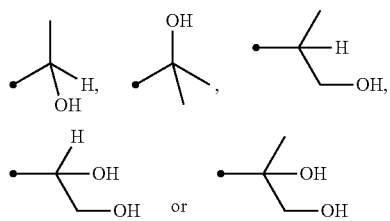

provided that, in the general formula (I), for example, tautomers with a hydrogen at different positions of the imidazole ring are included.

[2] The compound, or a pharmaceutically acceptable salt thereof according to [1], wherein the compound of general formula (I) has following structures:

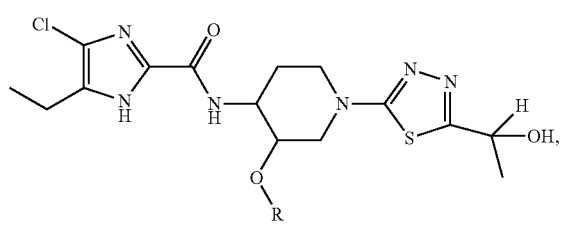
(Ia)

(Ib)

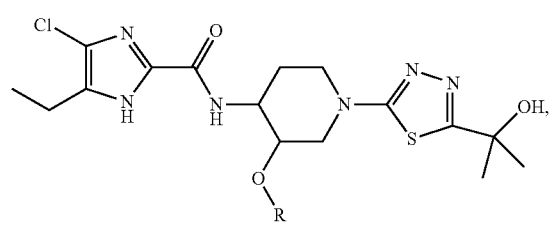

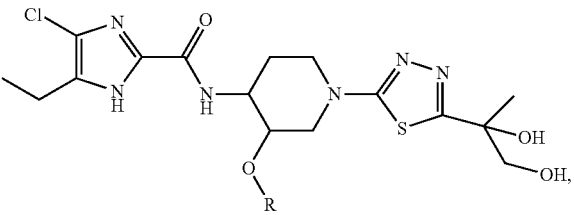
(Ic)

(Id)

(Ie)

[3] The compound or a pharmaceutically acceptable salt thereof according to [1], wherein the compound of general formula (I) has following structure:

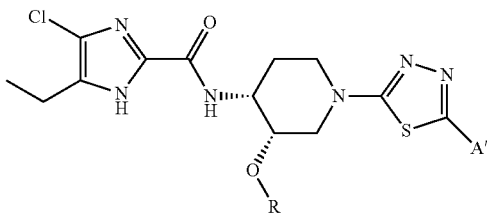

wherein R represents ($C_1$-$C_3$) alkyl, and
A' represents following formulae:

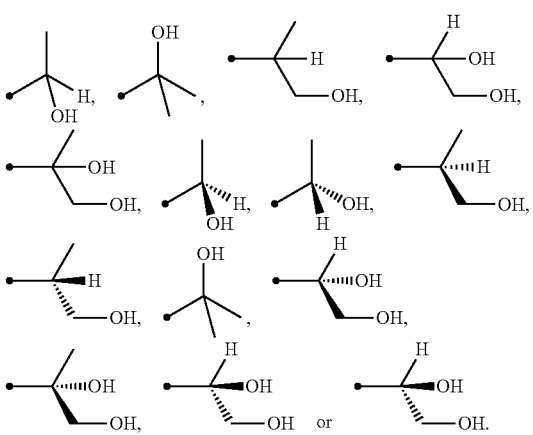

[4] The compound or a pharmaceutically acceptable salt thereof according to [3], wherein A' represents following formulae:

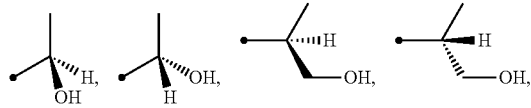

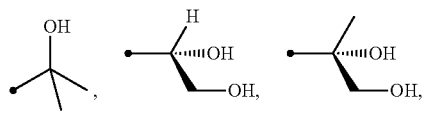

[5] The compound or a pharmaceutically acceptable salt thereof according to [1] or [3], wherein the compound of general formula (I) has following structure:

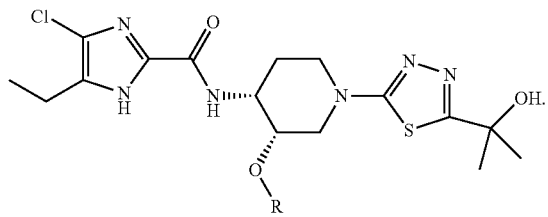

[6] The compound or a pharmaceutically acceptable salt thereof according to [1] or [4], wherein the compound of general formula (I) has following structures:

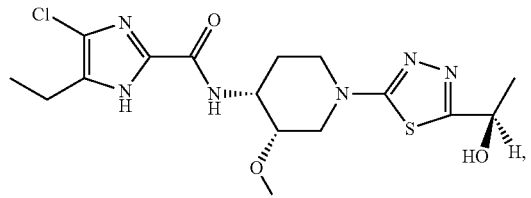

[7] The compound or a pharmaceutically acceptable salt thereof according to [1] or [4], wherein the compound of general formula (I) has following structures:

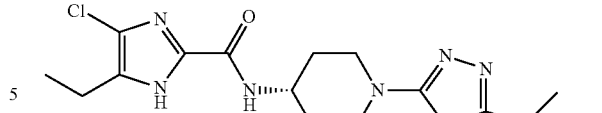

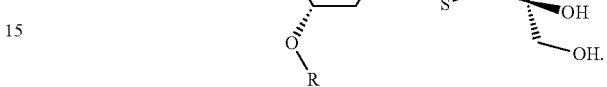

[8] The compound or a pharmaceutically acceptable salt thereof according to [1] or [4], wherein the compound of general formula (I) has following structures:

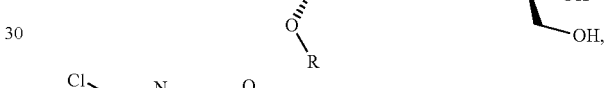

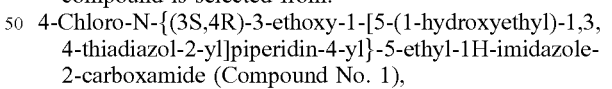

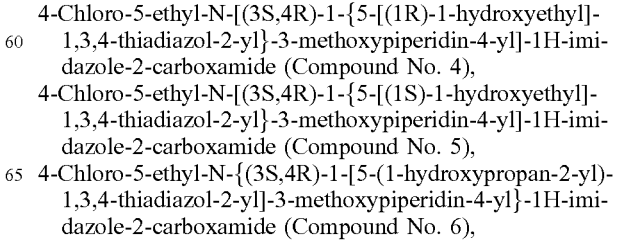

[9] The compound or a pharmaceutically acceptable salt thereof according to any one of [1] to [8], wherein R represents methyl.

[10] The compound or a pharmaceutically acceptable salt thereof according to any one of [1] to [8], wherein R represents ethyl.

[11] The compound or a pharmaceutically acceptable salt thereof according to any one of [1] to [10], wherein the compound is selected from:

4-Chloro-N-{(3S,4R)-3-ethoxy-1-[5-(1-hydroxyethyl)-1,3,4-thiadiazol-2-yl]piperidin-4-yl}-5-ethyl-1H-imidazole-2-carboxamide (Compound No. 1), 4-Chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (Compound No. 2), 4-Chloro-5-ethyl-N-{(3S,4R)-1-[5-(1-hydroxyethyl)-1,3,4-thiadiazol-2-yl]-3-methoxypiperidin-4-yl}-1H-imidazole-2-carboxamide (Compound No. 3), 4-Chloro-5-ethyl-N-[(3S,4R)-1-{5-[(1R)-1-hydroxyethyl]-1,3,4-thiadiazol-2-yl}-3-methoxypiperidin-4-yl]-1H-imidazole-2-carboxamide (Compound No. 4), 4-Chloro-5-ethyl-N-[(3S,4R)-1-{5-[(1S)-1-hydroxyethyl]-1,3,4-thiadiazol-2-yl}-3-methoxypiperidin-4-yl]-1H-imidazole-2-carboxamide (Compound No. 5), 4-Chloro-5-ethyl-N-{(3S,4R)-1-[5-(1-hydroxypropan-2-yl)-1,3,4-thiadiazol-2-yl]-3-methoxypiperidin-4-yl}-1H-imidazole-2-carboxamide (Compound No. 6),

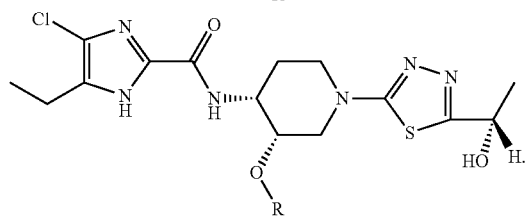

4-Chloro-N-{(3S,4R)-3-ethoxy-1-[5-(2-hydroxypropan-2-yl)-1,3,4-thiadiazol-2-yl]piperidin-4-yl}-5-ethyl-1H-imidazole-2-carboxamide (Compound No. 7), 4-Chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide (Compound No. 8), 4-Chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide (Compound No. 9), 4-Chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide (Compound No. 10), 4-Chloro-N-[(3S,4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamide (Compound No. 11).

[12] The crystalline 2/3 hydrate form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide, characterized by powder x-ray diffraction (XRD) spectrum substantially in accordance with the pattern shown in FIG. 2.

[13] The anhydrous crystalline form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide, characterized by powder x-ray diffraction (XRD) spectrum substantially in accordance with the pattern shown in FIG. 5.

[14] The crystalline form of 4-chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide, characterized by powder x-ray diffraction (XRD) spectrum substantially in accordance with the pattern shown in FIG. 8.

[15] The crystalline form of 4-chloro-N-[(3S,4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamide, characterized by powder x-ray diffraction (XRD) spectrum substantially in accordance with the pattern shown in FIG. 9.

[16] The anhydrous crystalline form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide.

[17] A pharmaceutical composition comprising a therapeutically effective amount of a compound, or a pharmaceutically acceptable salt thereof according to any one of [1] to [16] as its active ingredient.

[18] A pharmaceutical composition according to [17], wherein said pharmaceutical composition is administered to treat or prevent bacterial infectious diseases.

[19] The pharmaceutical composition according to [18], wherein said bacterial infectious diseases is caused by Gram-positive bacteria selected from genus *Staphylococcus, Streptococcus, Enterococcus, Clostridium, Bacillus, Corynebacterium*, and *Listeria* species.

[20] The pharmaceutical composition according to [18], wherein said bacterial infectious diseases is caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

[21] The pharmaceutical composition according to [18], wherein said bacterial infectious diseases is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[22] The pharmaceutical composition according to [18], wherein said bacterial infectious diseases is selected from community-acquired respiratory infections, hospital-acquired infections or *Clostridium difficile* infections.

[23] A method for treating bacterial infectious disease in a patient comprising administering to said patient a therapeutically effective amount of a compound or a pharmaceutical salt thereof according to any one of [1] to [16].

[24] The method according to [23], wherein said bacterial infectious diseases is caused by Gram-positive bacteria selected from genus *Staphylococcus, Streptococcus, Enterococcus, Clostridium, Bacillus, Corynebacterium*, and *Listeria* species.

[25] The method according to [23], wherein said bacterial infectious diseases is caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

[26] The method according to [23], wherein said bacterial infectious diseases is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[27] The method according to [23], wherein said bacterial infectious diseases is selected from community-acquired respiratory infections, hospital-acquired infections or *Clostridium difficile* infections.

[28] A compound, or a pharmaceutically acceptable salt thereof according to any one of [1] to [16] for use as a pharmaceutical agent for treating bacterial infectious diseases.

[29] The use according to [28], wherein said bacterial infectious diseases is caused by Gram-positive bacteria selected from genus *Staphylococcus, Streptococcus, Enterococcus, Clostridium, Bacillus, Corynebacterium*, and *Listeria* species.

[30] The use according to [28], wherein said bacterial infectious diseases is caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

[31] The use according to [28], wherein said bacterial infectious diseases is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[32] The use according to [28], wherein said bacterial infectious diseases is selected from community-acquired respiratory infections, hospital-acquired infections or *Clostridium difficile* infections.

[33] A DNA gyrase GyrB subunit and/or topoisomerase IV ParE subunit inhibitor for use in the treatment of bacterial infectious diseases having structure of general formula (I), a polymorphic form, a hydrate, or a pharmaceutically acceptable salt thereof:

(I)

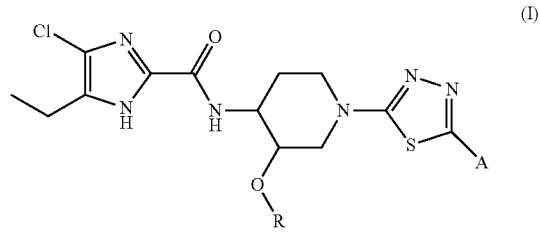

wherein R represents ($C_1$-$C_3$) alkyl, and
A represents following formulae:

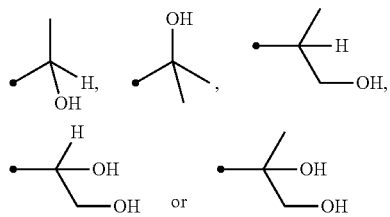

provided that, in the general formula (I), for example, tautomers with a hydrogen at different positions of the imidazole ring are included.

[34] The DNA gyrase GyrB subunit and/or topoisomerase IV ParE subunit inhibitor according to [33], wherein the compound is selected from:

(Ia)

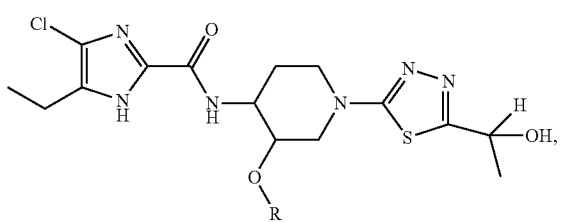

(Ib)

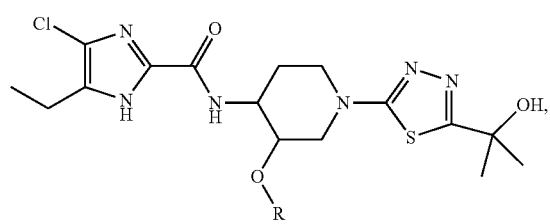

(Ic)

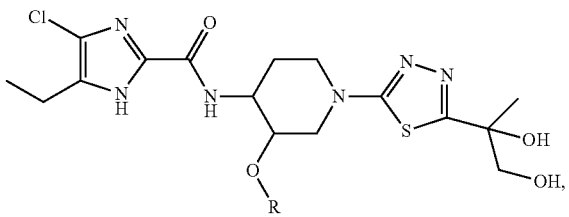

(Id)

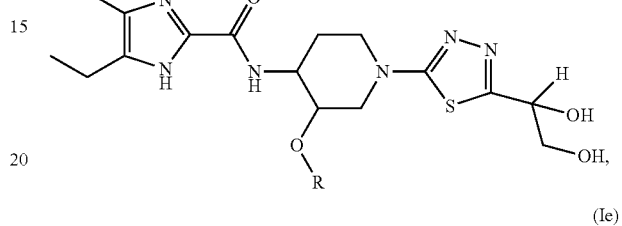

(Ie)

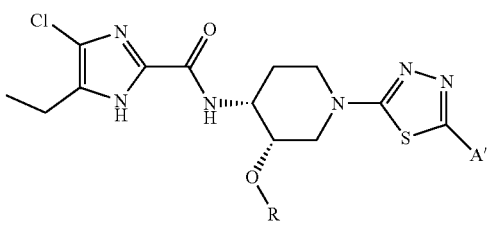

wherein R represents ($C_1$-$C_3$) alkyl.

[35] The DNA gyrase GyrB subunit and/or topoisomerase IV ParE subunit inhibitor according to [33], wherein the compound is represented by:

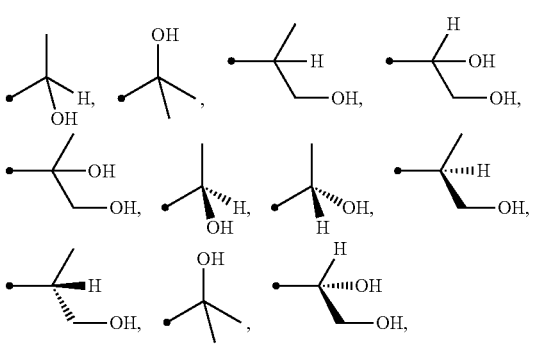

wherein R represents ($C_1$-$C_3$) alkyl, and
A' represents following formulae:

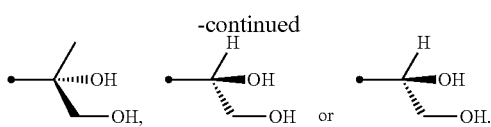

[36] The compound or a pharmaceutically acceptable salt thereof according to [35], wherein A' represents following formulae:

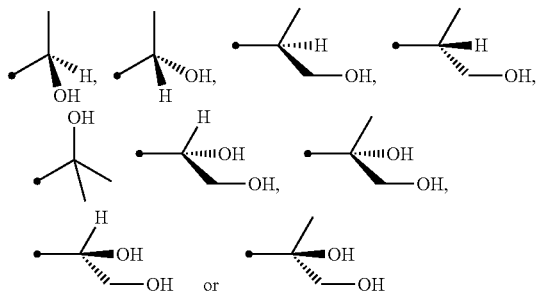

[37] The DNA gyrase GyrB subunit and/or topoisomerase IV ParE subunit inhibitor according to any one of [33] to [36], wherein said bacterial infectious diseases is caused by Gram-positive bacteria selected from genus *Staphylococcus, Streptococcus, Enterococcus, Clostridium, Bacillus, Corynebacterium*, and *Listeria* species.

[38] The DNA gyrase GyrB subunit and/or topoisomerase IV ParE subunit inhibitor according to any one of [33] to [36], wherein said bacterial infectious diseases is caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

[39] The DNA gyrase GyrB subunit and/or topoisomerase IV ParE subunit inhibitor according to any one of [33] to [36], wherein said bacterial infectious diseases is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[40] The DNA gyrase GyrB subunit and/or topoisomerase IV ParE subunit inhibitor according to any one of [33] to [36], wherein said bacterial infectious diseases is selected from community-acquired respiratory infections, hospital-acquired infections or *Clostridium difficile* infections.

[41] Use of a compound, a polymorphic form, or a pharmaceutically acceptable salt thereof according to any one of [1] to [16] for the production of a therapeutic agent for bacterial infections.

[42] The use according to [41], wherein said bacterial infections are caused by Gram-positive bacteria selected from genus *Staphylococcus, Streptococcus, Enterococcus, Clostridium, Bacillus, Corynebacterium*, and *Listeria* species.

[43] The use according to [42], wherein resistant bacteria is selected from methicillin-resistant *Staphylococcus aureus* (MRSA), penicillin-resistant *Streptococcus pneumoniae* (PRSP), and vancomycin-resistant *Enterococcus* (VRE).

[44] The use according to any one of [41] to [42], wherein said bacterial infectious diseases is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

[45] The use according to [44], wherein said bacterial infectious diseases is selected from community-acquired respiratory infections, hospital-acquired infections or *Clostridium difficile* infections.

[46] A method for the preparation of a compound of the following formula, a stereoisomer, or a pharmaceutically acceptable salt thereof:

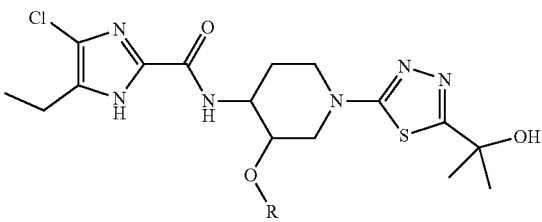

in which di-methylation is conducted on carbonyl carbon atom of —C(=O)—O—$R_1$ moiety of a compound having the following formula or a stereoisomer thereof:

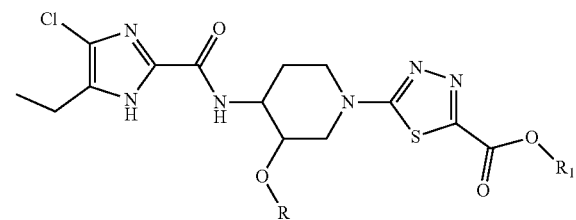

wherein, R represents ($C_1$-$C_3$) alkyl group and $R_1$ represents an alkyl group.

[47] The method according to [46], wherein the di-methylation is conducted by Grignard reaction.

[48] A method for the preparation of a compound of the following formula, a stereoisomer, or a pharmaceutically acceptable salt thereof:

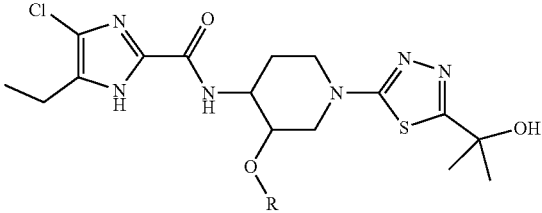

in which a compound of the following formula or a stereoisomer thereof:

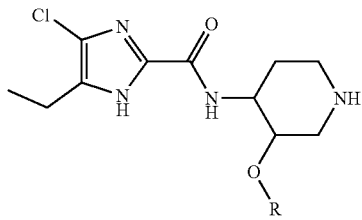

is reacted with a compound of the following formula:

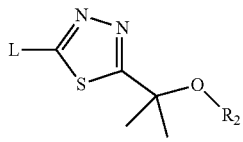

wherein, L represents a leaving group, $R_2$ represents a protective group for hydroxy group, and R is as defined in [46], to yield a compound of the following formula or a stereoisomer thereof:

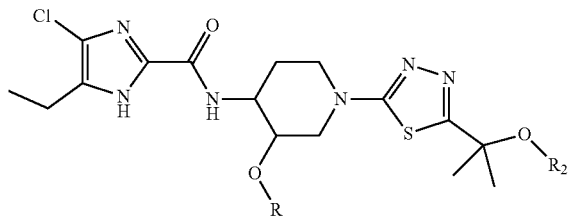

and then the protective group thereof is removed.

[49] The method according to [48], wherein L is a halogen atom.

[50] The method according to [49], wherein L is a bromine atom.

[51] A method for the preparation of a compound having the following formula, a stereoisomer, or a pharmaceutically acceptable salt thereof:

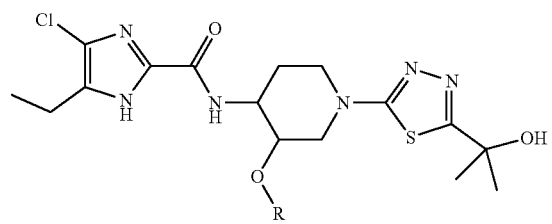

in which a compound of the following formula or a stereoisomer thereof:

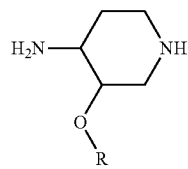

is reacted with a compound of the following formula:

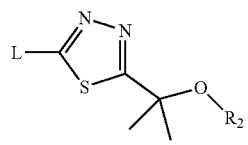

to yield a compound having the following formula or a stereoisomer thereof:

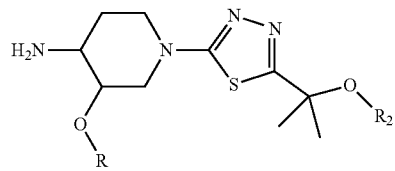

and said compound is reacted with a compound having the following formula:

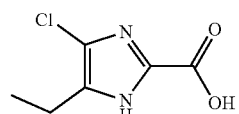

to yield a compound having the following formula or a stereoisomer thereof:

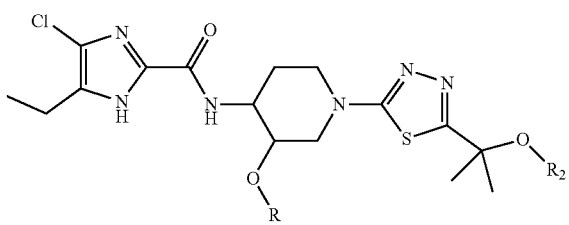

and then the protective group thereof is removed, wherein L, R and $R_2$ are as defined in [48].

[52] The method according to any one of [48] 51], wherein $R_2$ is alkyl group, aralkyl group, or acyl group.

[53] The method according to [52], wherein $R_2$ is acyl group.

[54] The method according to any one of [48] to [51], wherein $R_2$ is selected from a group of methyl group, tert-butyl group, benzyl group, p-methoxy benzyl group, methoxymethyl group, ethoxymethyl group, 2-tetrahydropyranyl group, acetyl group, pivaloyl group, and benzoyl group.

[55] The method according to [54], wherein $R_2$ is selected from the group of acetyl group, pivaloyl group, and benzoyl group.

[56] The method according to [54], wherein R₂ is benzoyl group.

[57] The method according to any one of [46] to [56], wherein the compound thus obtained has the following structure:

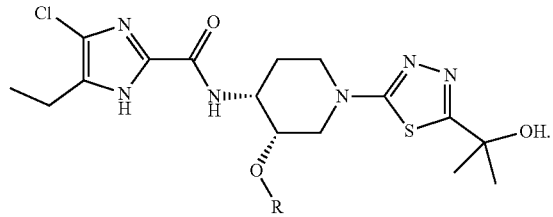

[58] The method according to any one of [46] to [57], wherein R is a methyl group or an ethyl group.

[59] The method according to any one of [46] to [57], wherein R is a methyl group.

[60] A method for the preparation of a compound of the following formula, a stereoisomer, or a pharmaceutically acceptable salt thereof:

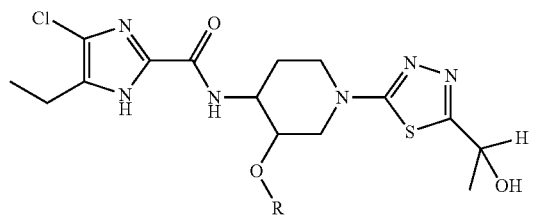

in which the compound of the following formula or a stereoisomer thereof:

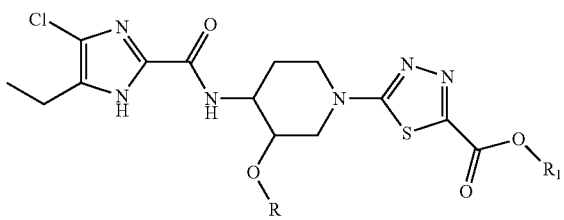

is reduced to yield the compound of the following formula or a stereoisomer thereof:

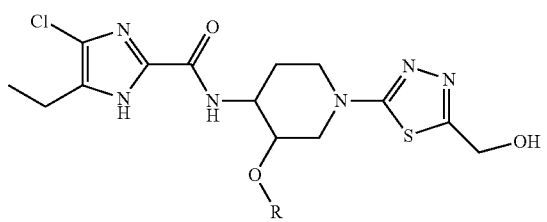

and then oxidation is conducted with said compound to yield compound of the following formula or a stereoisomer thereof:

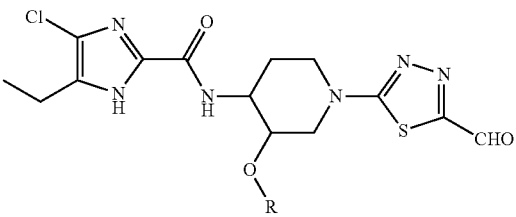

and methylation is conducted on the carbon atom of formyl group of said compound.

[61] The method according to [60], wherein the reduction is conducted by borohydride.

[62] The method according to [61], wherein the reduction is conducted by sodium borohydride.

[63] The method according to any one of [60] to [62], wherein the methylation is conducted by Grignard reaction.

[64] The method according to any one of [60] to [63], wherein the compound thus obtained has a structure of

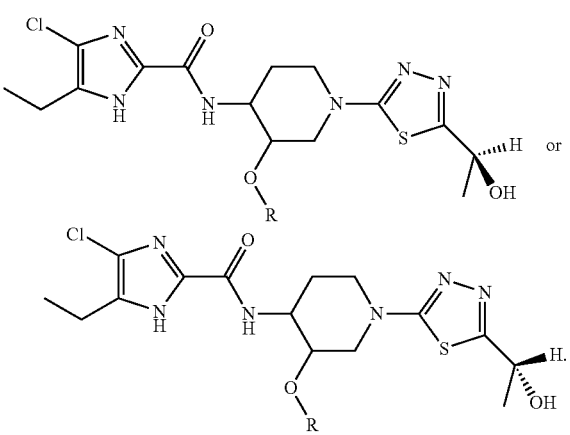

[65] The method according to any one of [60] to [64], wherein the compound thus obtained has a structure of

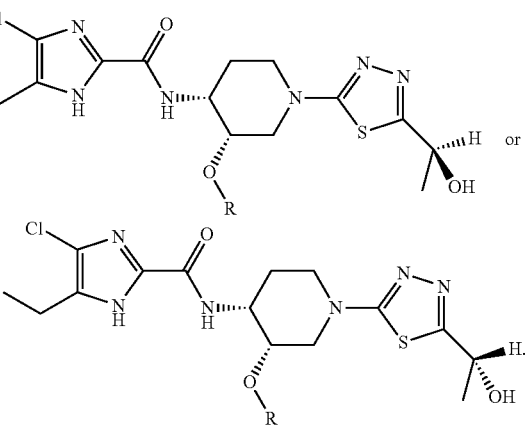

[66] A method for the preparation of a compound of the following formula, a stereoisomer, or a pharmaceutically acceptable salt thereof:

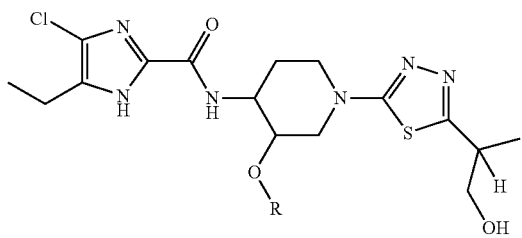

in which the compound of the following formula or a stereoisomer thereof:

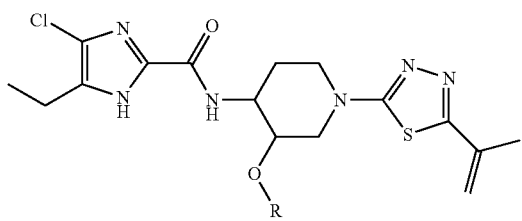

is reacted with borane and followed by treatment with hydrogen peroxide.

[67] The method according to [66], wherein compound thus obtained has the structure of

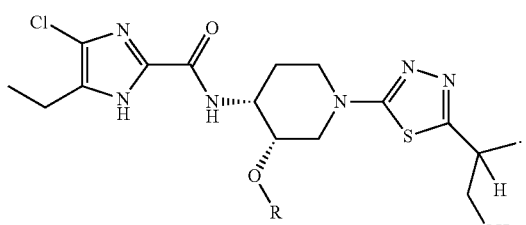

[68] A method for the preparation of a compound of the following formula, a stereoisomer, or a pharmaceutically acceptable salt thereof:

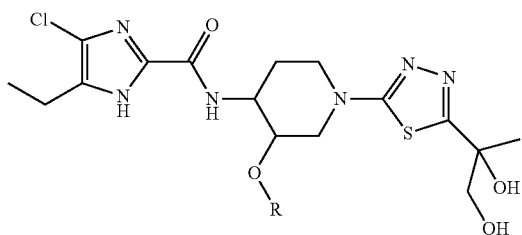

in which dihydroxylation is conducted on 5-ethenyl group of 1,3,4-thiadiazole moiety of a compound of the following formula or a stereoisomer thereof:

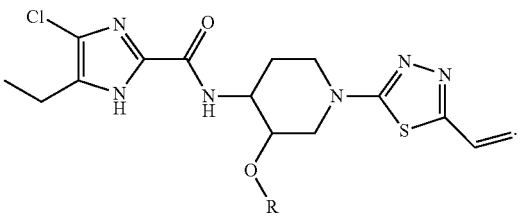

[69] The method according to [68], wherein the dihydroxylation is asymmetric dihydroxylation.

[70] The method according to [69], wherein the asymmetric dihydroxylation is Sharpless asymmetric dihydroxylation.

[71] The method according to any one of [68] or [70], wherein the compound thus obtained has a structure of

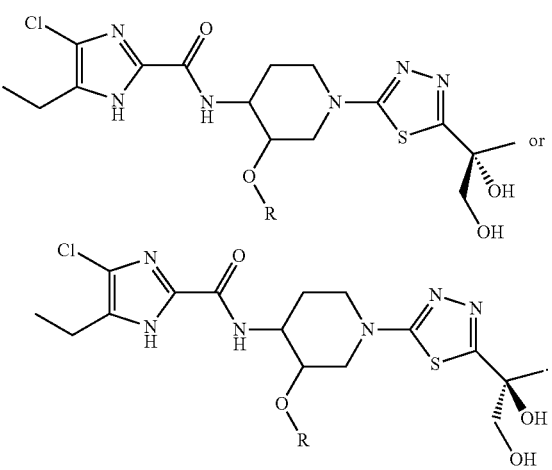

[72] The method according to any one of [68] or [70], wherein the compound thus obtained has a structure of

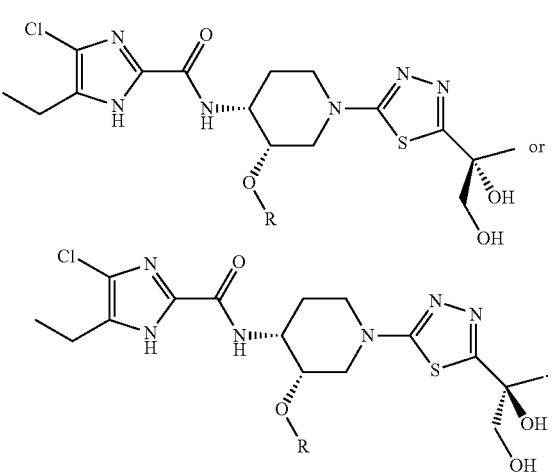

BRIEF DESCRIPTION OF THE DRAWINGS

Various aspects of the present invention are illustrated by reference to the following drawings.

Figure 1:
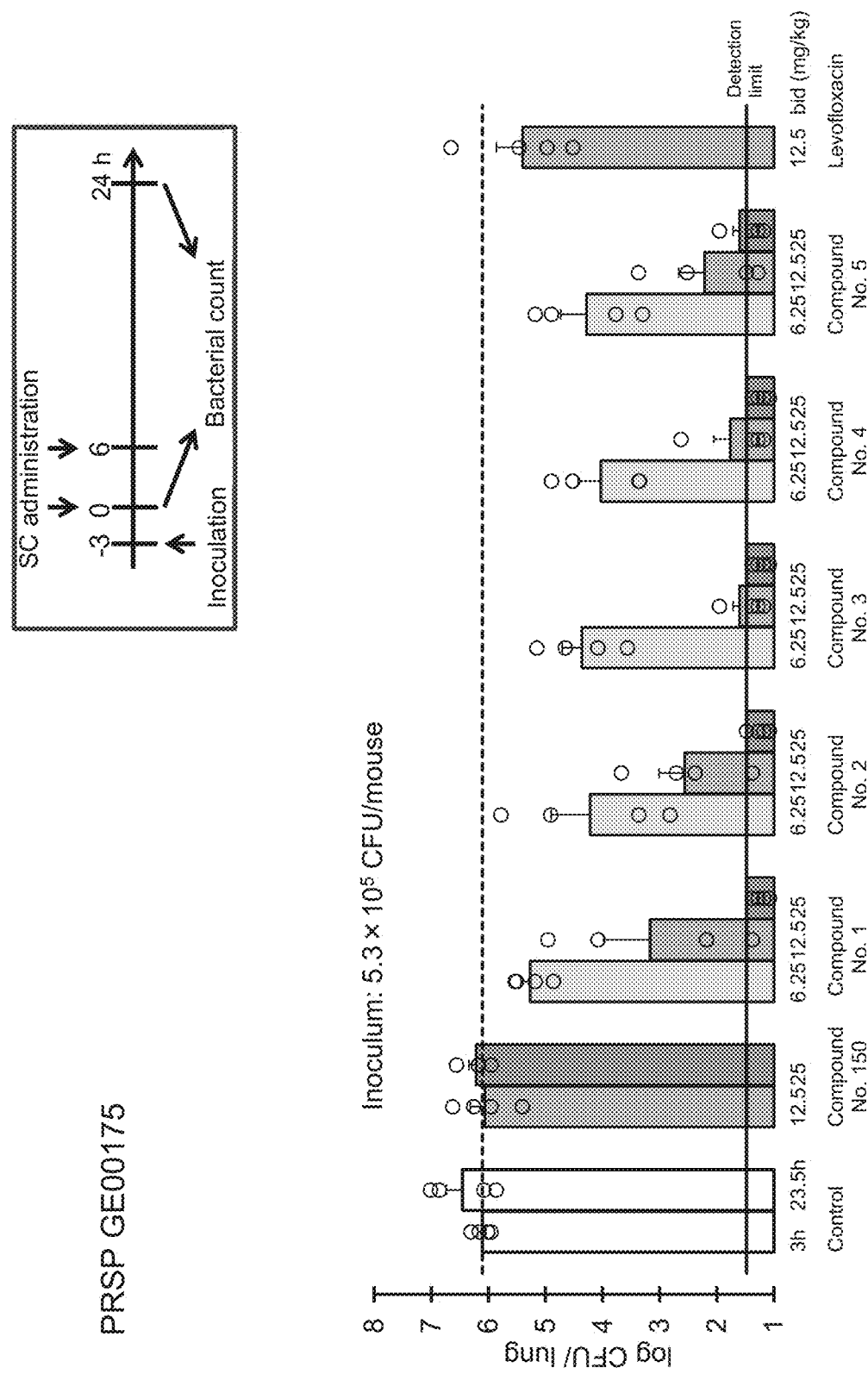
FIG. 1: Efficacy in mouse lung infection model by penicillin-resistant *Streptococcus pneumoniae* (PRSP).

The aforementioned aspects and embodiments, and other aspects, objects, features and advantages of the present invention will be apparent from the following detailed description and the appended claims thereof.

DETAILED DESCRIPTION OF THE INVENTION

As used herein the following definitions apply unless clearly indicated otherwise.

It should be understood that unless expressly stated to the contrary, "a compound of general formula (I)" refers to and includes any and all compounds described by formula (I), its embodiments, as well as subgenuses, inclusive of all salts, stereoisomers thereof. It should also be noted that the singular forms "a" "an" and "the" include plural reference unless the context clearly dictates otherwise.

In one aspect of the present invention, there is provided a compound of general formula (I), a stereoisomer, or a pharmaceutically acceptable salt thereof:

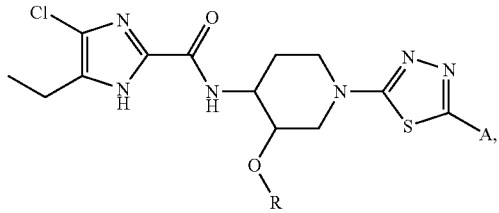
(I)

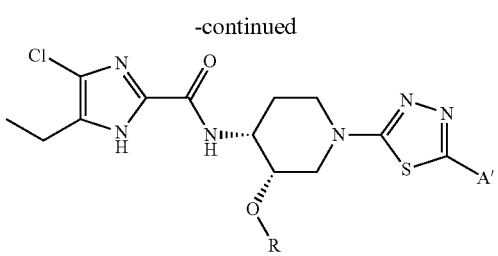
-continued wherein R, A and A' are as defined above.

The compound of general formula (I) may have tautomers with a hydrogen at different positions of the imidazole ring. All such tautomers are within the scope of the present invention. The compound of general formula (I) includes following structures:

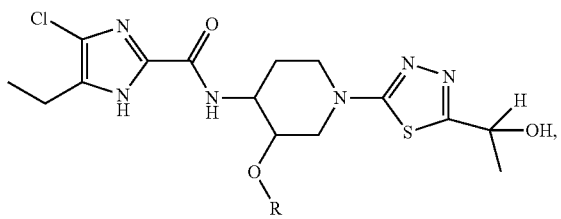
(Ia)

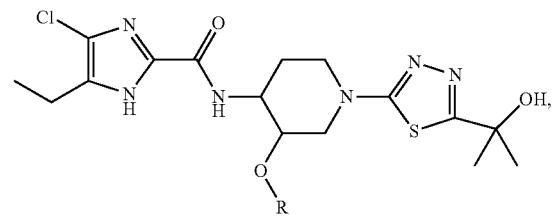
(Ib)

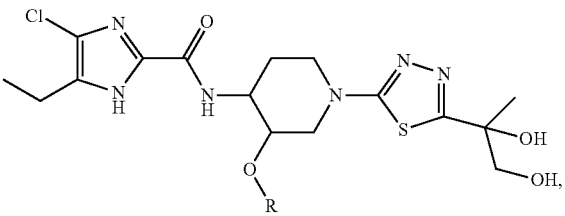
(Ic)

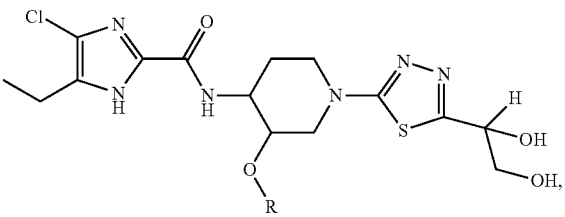
(Id)

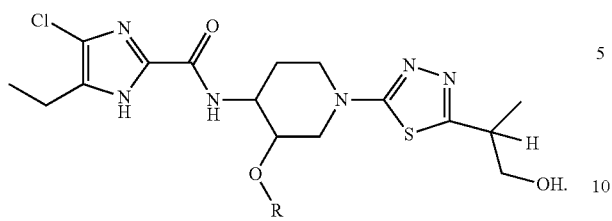

In a preferred embodiment, there is provided a compound of formula (Ia), a stereoisomer, or a pharmaceutically acceptable salt thereof;

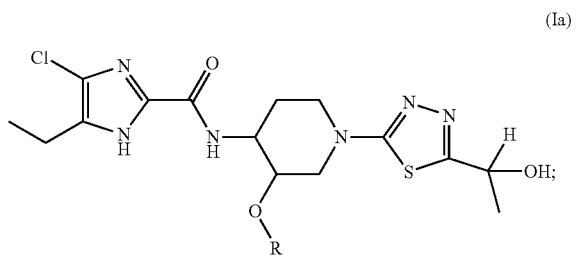

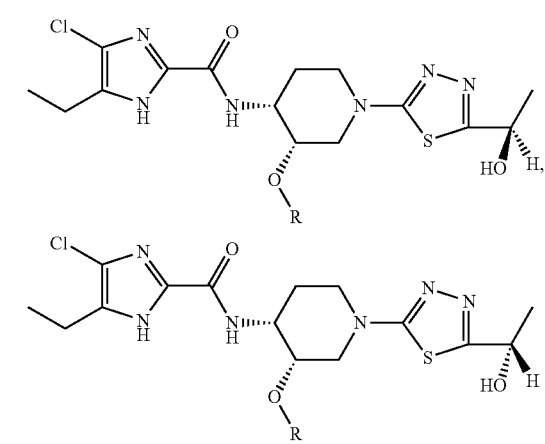

wherein R represents $(C_1-C_3)$ alkyl, and tautomers with a hydrogen at different positions of the imidazole ring are included.

In another preferred embodiment, there is provided a compound of formula (Ib), a stereoisomer, or a pharmaceutically acceptable salt thereof;

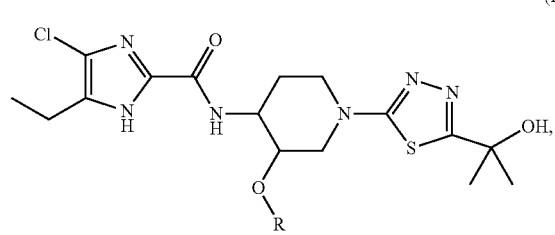

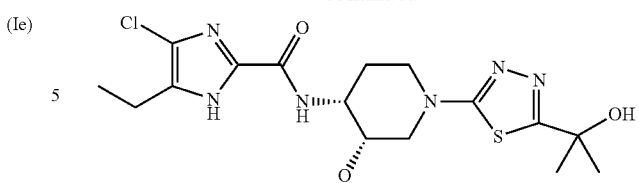

wherein R represents $(C_1-C_3)$ alkyl, and tautomers with a hydrogen at different positions of the imidazole ring are included.

In another preferred embodiment, there is provided a compound of formula (Ic), a stereoisomer, or a pharmaceutically acceptable salt thereof;

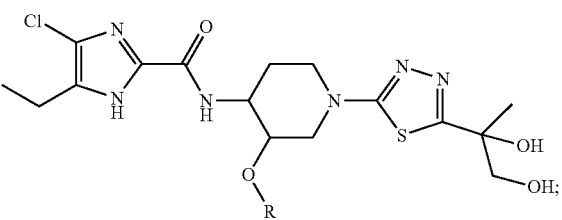

wherein R represents $(C_1-C_3)$ alkyl; and tautomers with a hydrogen at different positions of the imidazole ring are included.

In another preferred embodiment, there is provided a compound of formula (Id), a stereoisomer, or a pharmaceutically acceptable salt thereof;

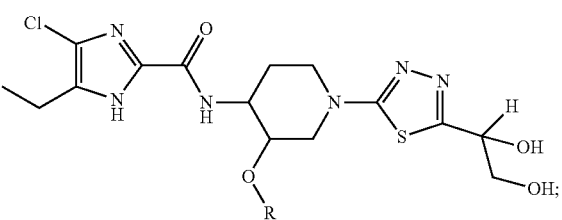

-continued

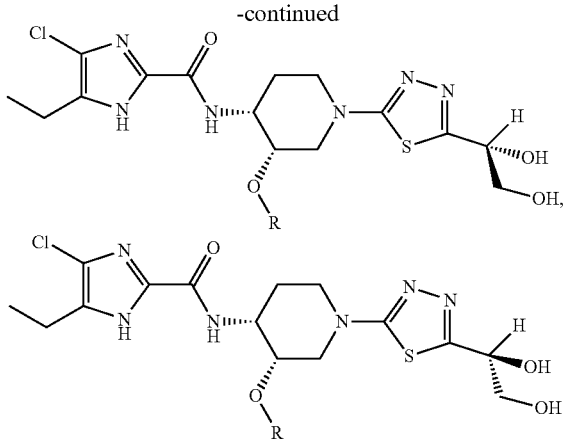

wherein R represents (C$_1$-C$_3$) alkyl; and tautomers with a hydrogen at different positions of the imidazole ring are included.

In another preferred embodiment, there is provided a compound of formula (Ie), a stereoisomer, or a pharmaceutically acceptable salt thereof;

(Ie)

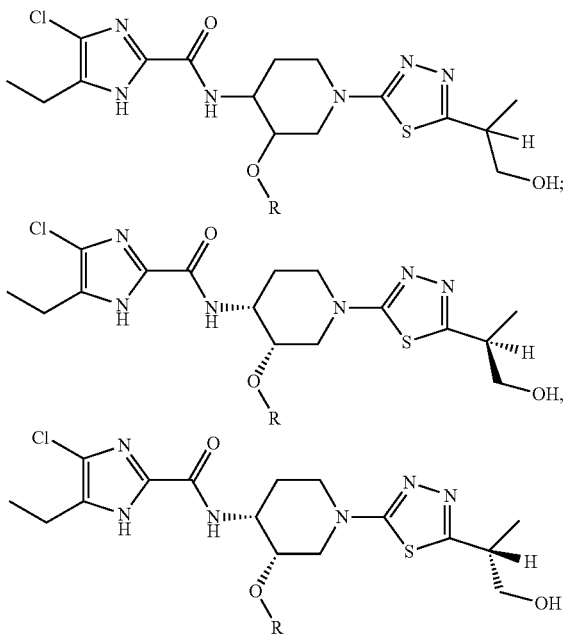

wherein R represents (C$_1$-C$_3$) alkyl; and tautomers with a hydrogen at different positions of the imidazole ring are included.

The present invention intends to include within the scope of the first aspect, various preferred embodiments for perfecting the invention as pointed out in the background section.

For example, in one embodiment, there is provided a compound of formula (Ia), a stereoisomer, a pharmaceutically acceptable salt thereof, wherein R represents methyl or ethyl.

In another embodiment, there is provided a compound of formula (Ib), a stereoisomer, a pharmaceutically acceptable salt thereof, wherein R represents methyl or ethyl.

In another embodiment, there is provided a compound of formula (Ic), a stereoisomer, a pharmaceutically acceptable salt thereof, wherein R represents methyl or ethyl.

In another embodiment, there is provided a compound of formula (Id), a stereoisomer, a pharmaceutically acceptable salt thereof, wherein R represents methyl or ethyl.

In another embodiment, there is provided a compound of formula (Ie), a stereoisomer, a pharmaceutically acceptable salt thereof, wherein R represents methyl or ethyl.

According to a particular embodiment of the present invention, there is provided specific compound of formula (I), which is selected from:
4-Chloro-N-{(3S,4R)-3-ethoxy-1-[5-(1-hydroxyethyl)-1,3,4-thiadiazol-2-yl]piperidin-4-yl}-5-ethyl-1H-imidazole-2-carboxamide,
4-Chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide,
4-Chloro-5-ethyl-N-{(3S,4R)-1-[5-(1-hydroxyethyl)-1,3,4-thiadiazol-2-yl]-3-methoxypiperidin-4-yl}-1H-imidazole-2-carboxamide,
4-Chloro-5-ethyl-N-[(3S,4R)-1-{5-[(1R)-1-hydroxyethyl]-1,3,4-thiadiazol-2-yl}-3-methoxypiperidin-4-yl]-1H-imidazole-2-carboxamide,
4-Chloro-5-ethyl-N-[(3S,4R)-1-{5-[(1S)-1-hydroxyethyl]-1,3,4-thiadiazol-2-yl}-3-methoxypiperidin-4-yl]-1H-imidazole-2-carboxamide,
4-Chloro-5-ethyl-N-{(3S,4R)-1-[5-(1-hydroxypropan-2-yl)-1,3,4-thiadiazol-2-yl]-3-methoxypiperidin-4-yl}-1H-imidazole-2-carboxamide,
4-Chloro-N-{(3S,4R)-3-ethoxy-1-[5-(2-hydroxypropan-2-yl)-1,3,4-thiadiazol-2-yl]piperidin-4-yl}-5-ethyl-1H-imidazole-2-carboxamide,
4-Chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide,
4-Chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide,
4-Chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide,
4-Chloro-N-[(3S,4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamide, or a pharmaceutically acceptable salt thereof.

Figure 2:
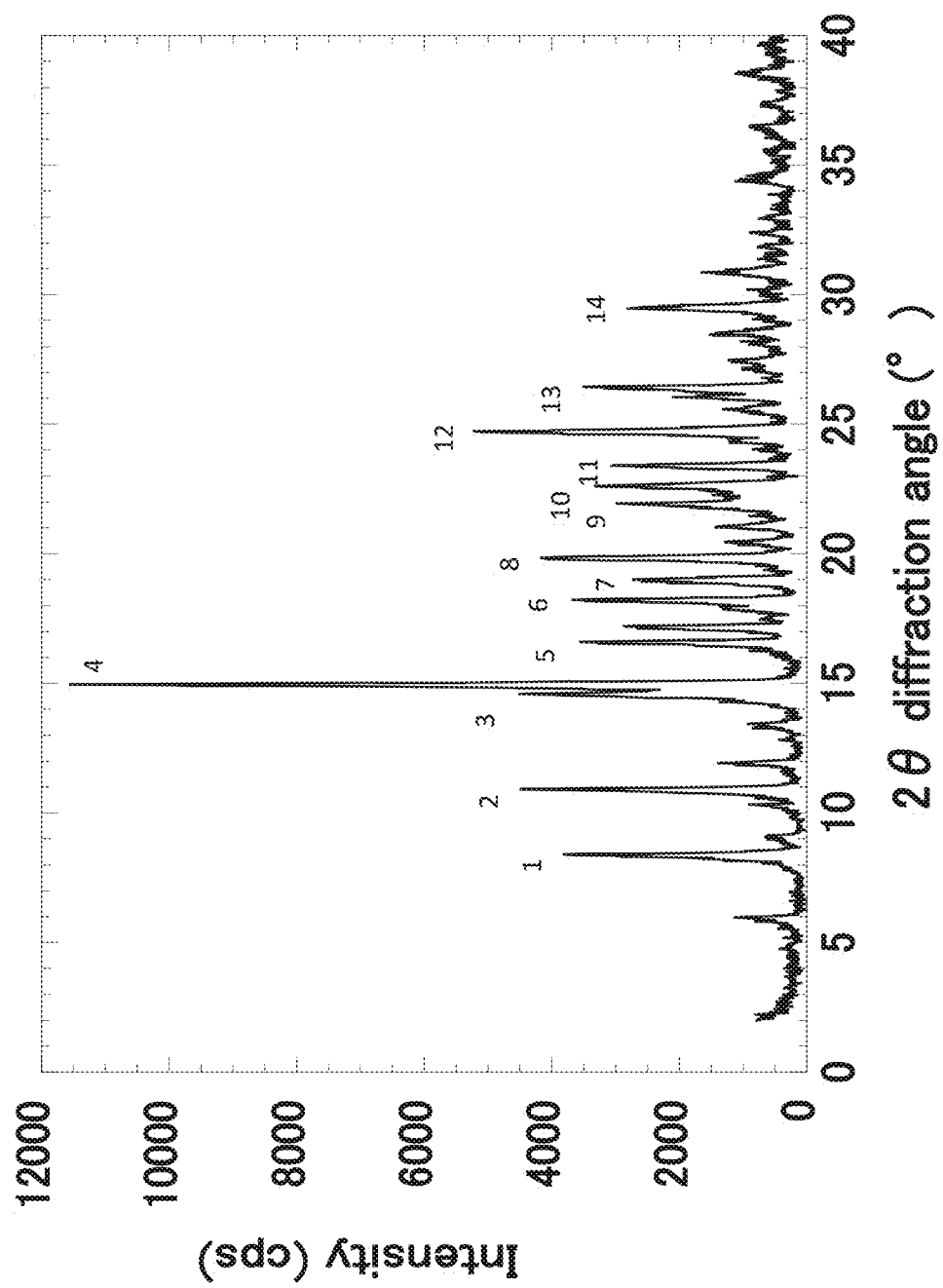
FIG. 2: The powder x-ray powder diffraction (XRD) pattern for crystalline 2/3 hydrate of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (Compound No. 2).

In a preferred embodiment, there is provided a crystalline 2/3 hydrate form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide, designated as Form I, characterized by powder x-ray diffraction (XRD) spectrum substantially in accordance with the pattern shown in FIG. 2.

Figure 3:
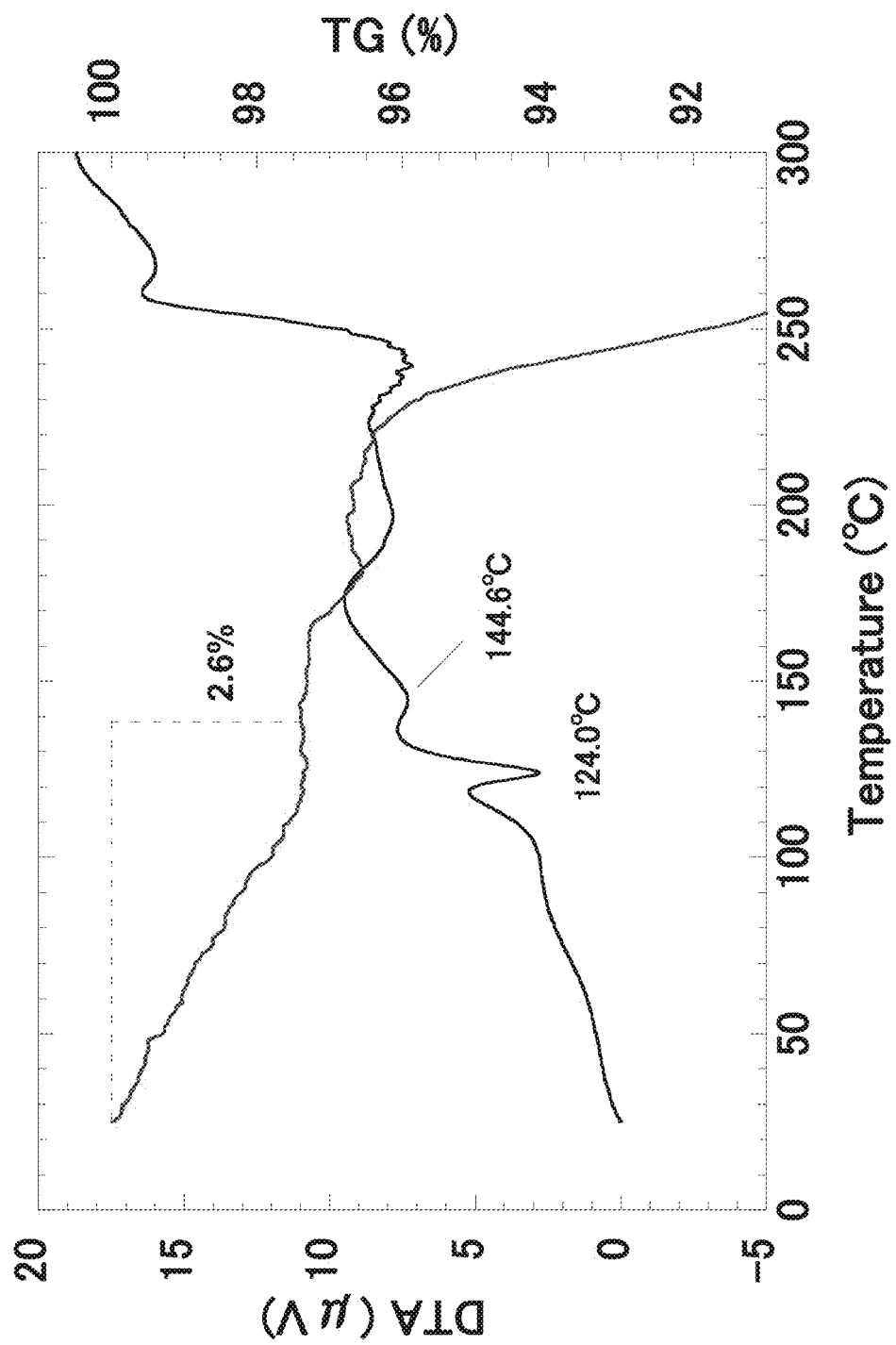
FIG. 3: The thermogravimetric analysis pattern (TG/DTA pattern) for crystalline 2/3 hydrate of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide.
Figure 4:
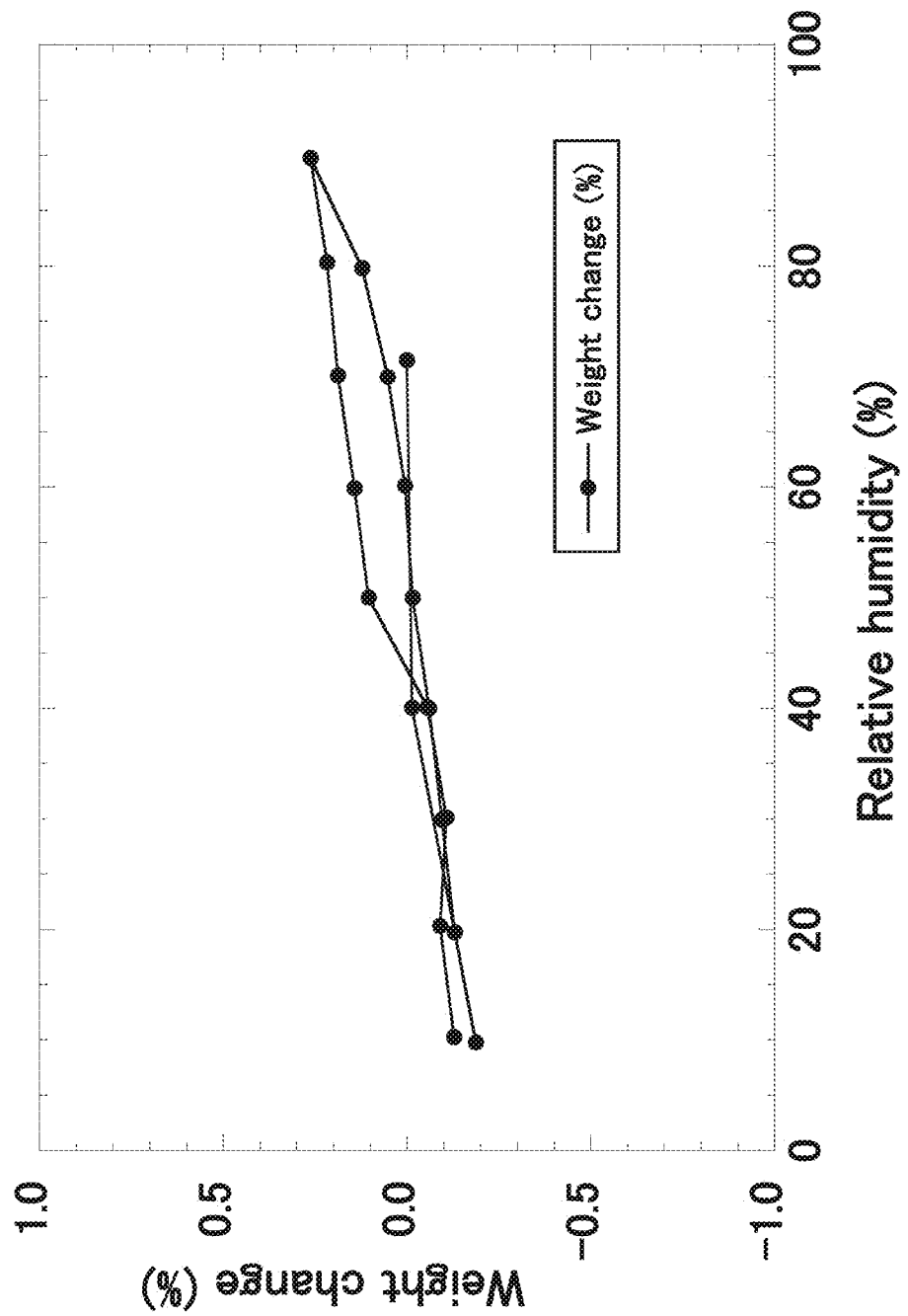
FIG. 4: The pattern of change of weight for crystalline 2/3 hydrate of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide.

Form I is further characterized by i) thermogravimetric analysis pattern (TG/DTA pattern) substantially in accordance with the pattern shown in FIG. 3, and ii) change in weight substantially in accordance with the pattern shown in FIG. 4.

Figure 5:
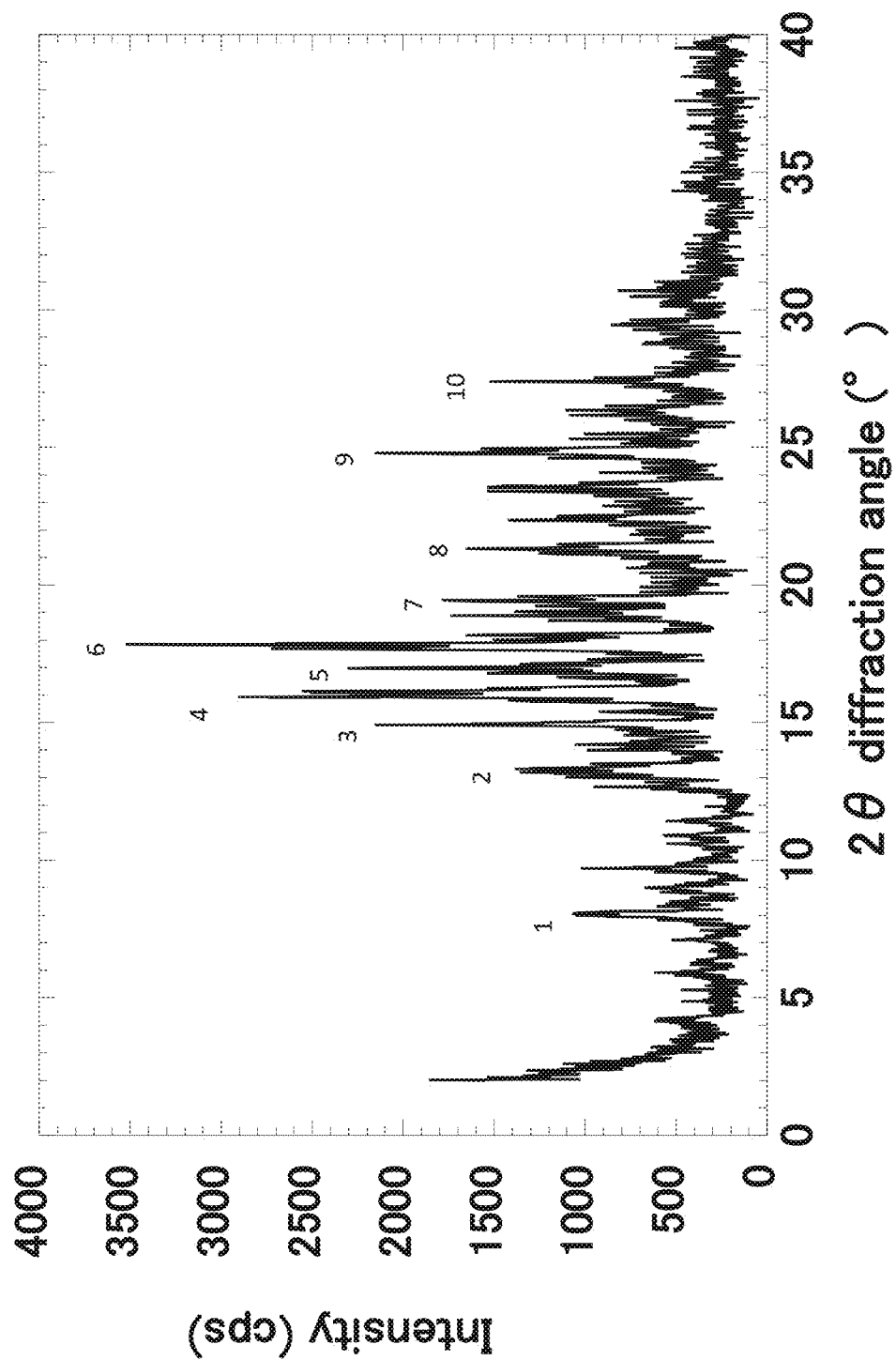
FIG. 5: The powder x-ray diffraction (XRD) pattern for anhydrous crystalline form of 4-chloro-5-ethyl-N-{(3S,4R)-1-[5-(1-hydroxy-1-methylethyl)-1,3,4-thiadiazol-2-yl]-3-methoxypiperidin-4-yl}-1H-imidazole-2-carboxamide.

In another embodiment, there is provided an anhydrous crystalline form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide, designated as Form II, characterized by powder x-ray diffraction (XRD) spectrum substantially in accordance with the pattern shown in FIG. 5.

Figure 6:
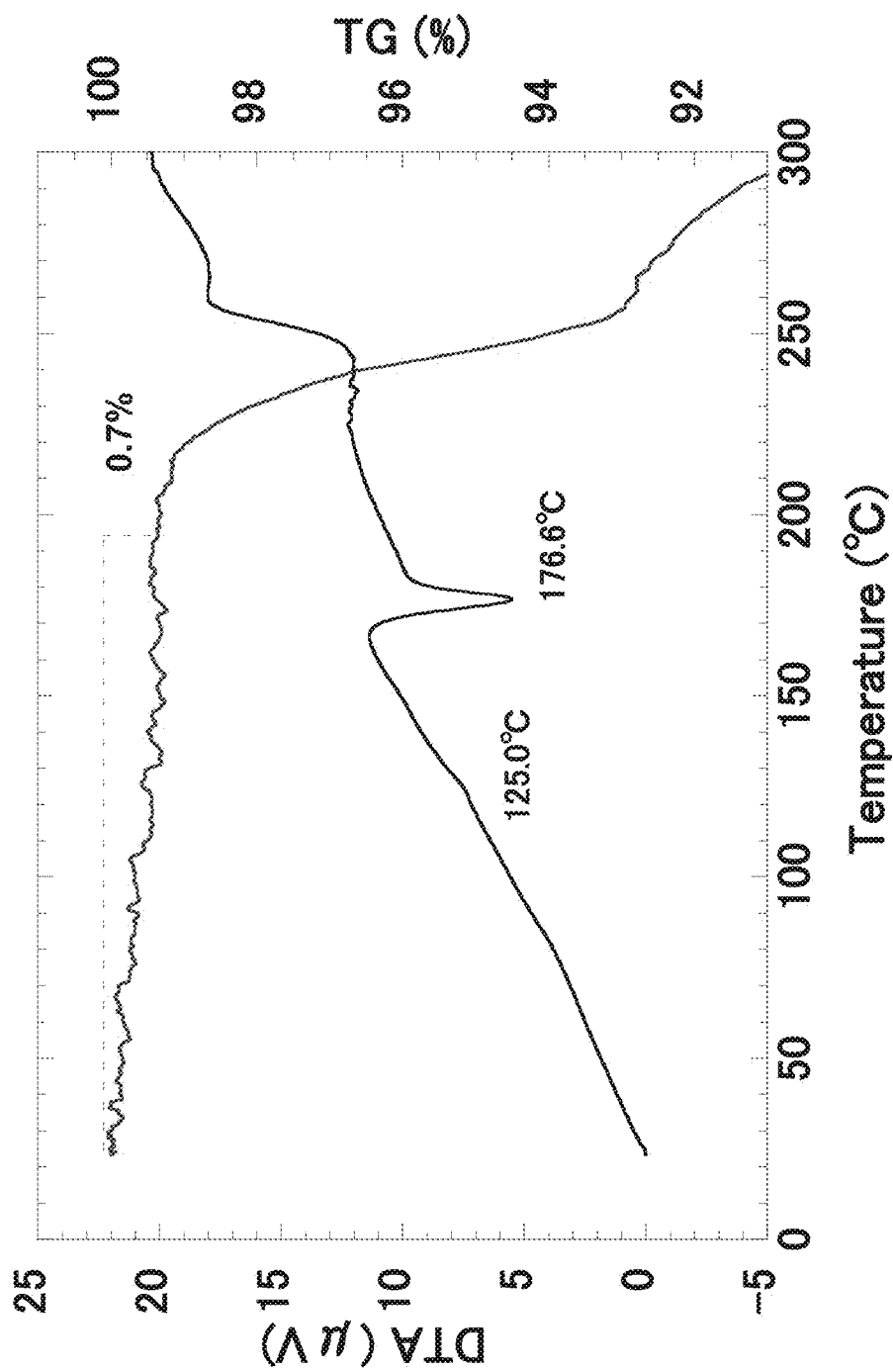
FIG. 6: The thermogravimetric analysis pattern (TG/DTA pattern) for anhydrous crystalline form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide.
Figure 7:
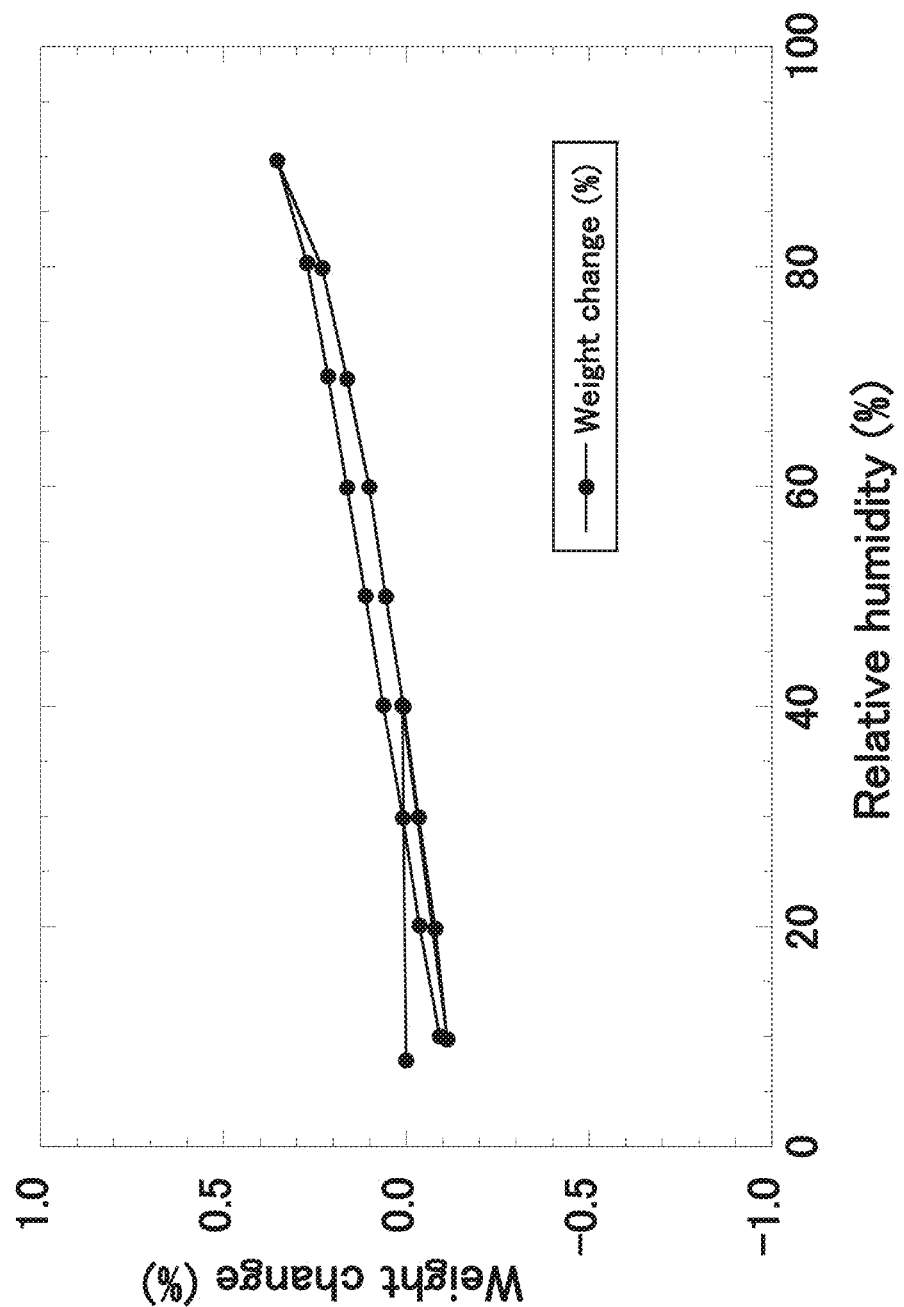
FIG. 7: The pattern of change of weight for anhydrous crystalline form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide.

Form II is further characterized by i) thermogravimetric analysis pattern (TG/DTA pattern) substancially in accordance with the pattern shown in FIG. 6, and ii) change in weight substancially in accordance with the pattern shown in FIG. 7.

Figure 8:
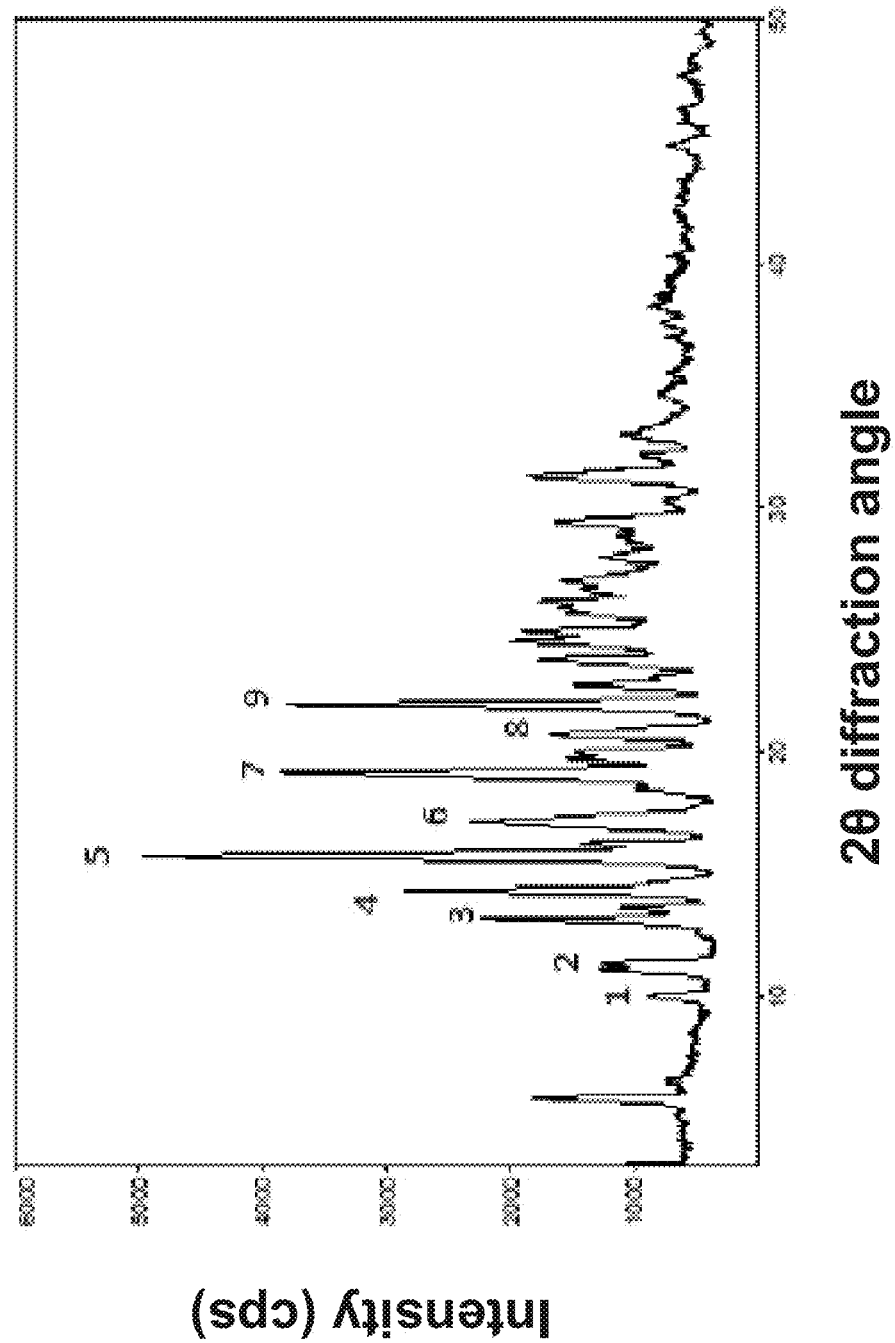
FIG. 8: The powder x-ray diffraction (XRD) pattern for 4-chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide.

In another embodiment, there is provided a crystalline form of 4-chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide, designated as Form A, characterized by an powder x-ray diffraction (XRD) spectrum substantially in accordance with the pattern shown in FIG. 8.

Figure 9:
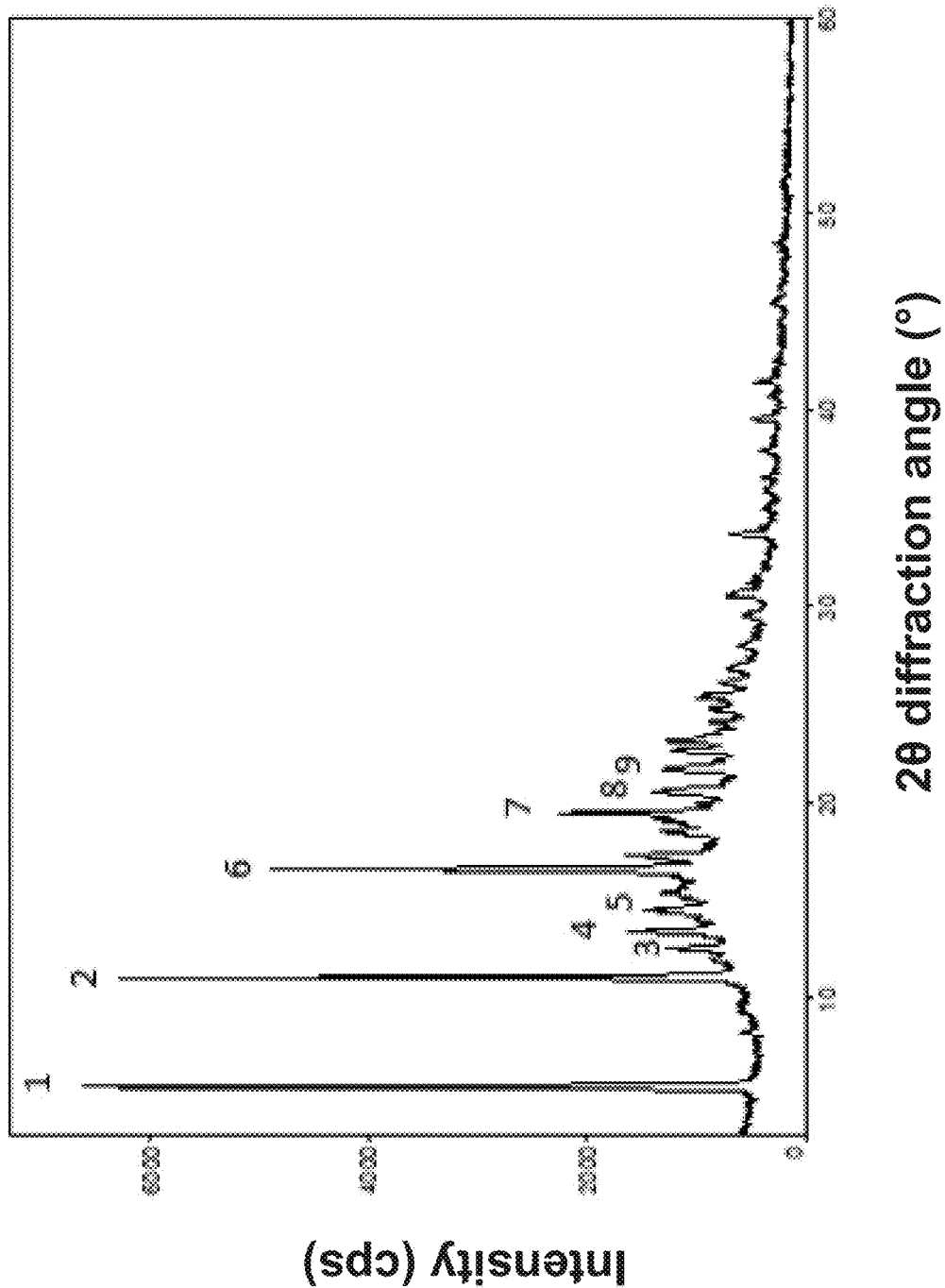
FIG. 9: The powder x-ray diffraction (XRD) pattern for 4-chloro-N-[(3S,4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamide.

In another embodiment, there is provided a crystalline form of 4-chloro-N-[(3S,4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamid, designated as Form B, characterized by powder x-ray diffraction (XRD) spectrum substantially in accordance with the pattern shown in FIG. 9.

In another embodiment, there is provided an anhydrous crystalline form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide.

In another preferred embodiment, Form I, Form II, Form A and Form B are further characterized by prominent XRD peaks as tabulated in Table 1.

TABLE 1

XRD (CuK, λ = 1.54 Å, scan rate = 20°/minute*)

| Peak | 2θ | d | Relative Intensity |
|---|---|---|---|
| Prominent Peaks (Form I) | | | |
| 1 | 8.38 | 10.54 | 34 |
| 2 | 10.90 | 8.11 | 43 |
| 3 | 14.50 | 6.08 | 38 |
| 4 | 14.94 | 5.92 | 100 |
| 5 | 16.56 | 5.35 | 31 |
| 6 | 18.18 | 4.88 | 31 |
| 7 | 18.96 | 4.68 | 23 |
| 8 | 19.82 | 4.48 | 36 |
| 9 | 21.90 | 4.06 | 23 |
| 10 | 22.60 | 3.93 | 27 |
| 11 | 23.38 | 3.80 | 27 |
| 12 | 24.68 | 3.60 | 42 |
| 13 | 26.38 | 3.38 | 26 |
| 14 | 29.48 | 3.03 | 23 |
| Prominent Peaks (Form II) | | | |
| 1 | 8.04 | 10.99 | 44 |
| 2 | 13.20 | 6.67 | 48 |
| 3 | 14.94 | 5.92 | 77 |
| 4 | 16.08 | 5.51 | 100 |
| 5 | 17.00 | 5.21 | 72 |
| 6 | 17.76 | 4.99 | 100 |
| 7 | 19.46 | 4.56 | 57 |
| 8 | 21.36 | 4.16 | 42 |
| 9 | 24.82 | 3.58 | 70 |
| 10 | 27.38 | 3.25 | 57 |
| Prominent Peaks (Form A) | | | |
| 1 | 9.98 | 8.84 | 9.92 |
| 2 | 11.04 | 8.00 | 12.15 |
| 3 | 13.13 | 6.73 | 36.11 |
| 4 | 14.27 | 6.20 | 45.92 |
| 5 | 15.70 | 5.63 | 100 |
| 6 | 17.06 | 5.19 | 56.8 |
| 7 | 19.10 | 4.64 | 88.67 |
| 8 | 20.65 | 4.29 | 27.64 |
| 9 | 21.92 | 4.05 | 64.80 |
| Prominent Peaks (Form B) | | | |
| 1 | 6.52 | 13.54 | 3.97 |
| 2 | 11.33 | 7.80 | 17.84 |
| 3 | 13.13 | 6.73 | 36.11 |

TABLE 1-continued

XRD (CuK, λ = 1.54 Å, scan rate = 20°/minute*)

| Peak | 2θ | d | Relative Intensity |
|---|---|---|---|
| 4 | 13.58 | 6.51 | 14.45 |
| 5 | 14.27 | 6.20 | 45.92 |
| 6 | 14.64 | 6.04 | 14.13 |
| 7 | 18.39 | 4.82 | 10.86 |
| 8 | 19.10 | 4.64 | 88.67 |
| 9 | 19.70 | 4.50 | 24.4 |

*Scan rate 10°/minute (Form A & Form B)

In a preferred embodiment, Form I is characterized by major XRD peaks at 8.38, 10.90, 14.50, 14.94, 19.82 and 24.68 (2θ).

In another preferred embodiment, Form II is characterized by major XRD peaks at 13.20, 14.94, 16.08, 17.76, 19.46 and 24.82 (2θ).

In another preferred embodiment, Form A is characterized by major XRD peaks at 15.70, 17.06, 19.10 and 21.92 (2θ).

In yet another preferred embodiment, Form B is characterized by major XRD peaks at 13.13, 14.27 and 19.10 (2θ).

In the invention, it should be understood that a compound of general formula (I) or a salt thereof may sometimes indicate the tautomeric phenomenon, and the formulae and figures in the present specification can only represent one of the possible tautomeric forms. It should be understood that the present invention encompasses any of the tautomeric forms which inhibits DNA gyrase GyrB subunit and/or topoisomerase IV ParE subunit and is not limited to only one of the tautomeric forms used in the formulae or figures. It should be understood that the formulae and figures in the present specification can only represent one of the possible tautomeric forms and the present specification encompasses not only the forms which can be shown in the formulae but also all possible tautomeric forms of the compounds shown in the formulae. The same is also applicable to the compound names.

The compound of the present invention represented by general formula (I) or a pharmaceutically acceptable salt thereof, when left in the air or recrystallized, may absorb water to associate with adsorbed water or to form a hydrate. Such water-containing compounds and salts are also encompassed by the present invention.

The compound of the present invention represented by general formula (I) has a basic group, hence a "pharmaceutically acceptable salt thereof" can be formed by reacting the compound with an acid.

The term "pharmaceutically acceptable" as used herein refers to a compound of formula (I) or pharmaceutical composition thereof suitable for administration to animals, preferably humans as approved by a regulatory agency such as European Medicine Agency (EMEA), US Food and Drug Administration (FDA) or any other National Regulatory Agency.

Preferred examples of a salt of the present invention includes, but not limited to, hydrochloride, hydrobromide, hydroiodide, nitrate, perchlorate, sulfate, phosphate, methanesulfonate, trifluoromethanesulfonate, ethanesulfonate, benzenesulfonate, p-toluenesulfonate, acetate, malate, fumarate, succinate, citrate, ascorbate, tartrate, oxalate, maleate, and amino acid salts such as glycine salt, lysine salt, arginine salt, ornithine salt, glutamate, and aspartate.

The compound represented by general formula (I), or pharmaceutically acceptable salt thereof, has an asymmetric carbon atom in the molecule, hence stereoisomers with an R or S configuration are included. Each of these stereoisomers and all mixtures of the stereoisomers at arbitrary ratios are also encompassed by the present invention. Such stereoisomers can be prepared, for example, by synthesizing the compound (I) using appropriate resolving agents or by optically resolving the synthesized compound (I) by a usual optical resolution or separation method or diastereoselective synthesis as desired.

The compound of the present invention represented by general formula (I) or a pharmaceutically acceptable salt thereof includes optical isomers. Each of these optical isomers and all mixtures of these optical isomers are also encompassed by the present invention.

The compound of the present invention represented by general formula (I) or a pharmaceutically acceptable salt thereof include stereoisomers based on the type of substitution at 3 or 4 position of piperidine ring. For example, in general formula (I), the cis-isomer is the preferred one as shown below:

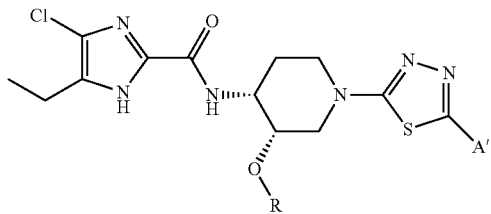

The present invention includes preferable isomers, but not limited to,

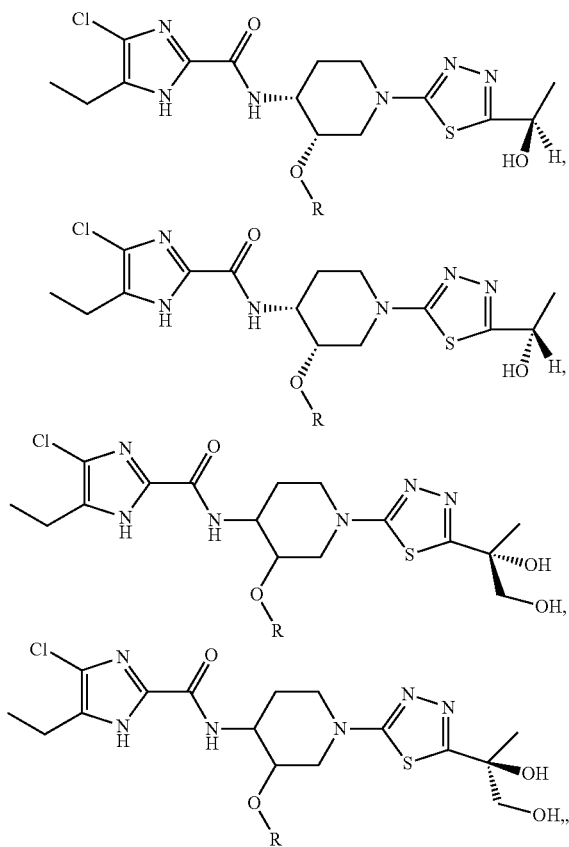

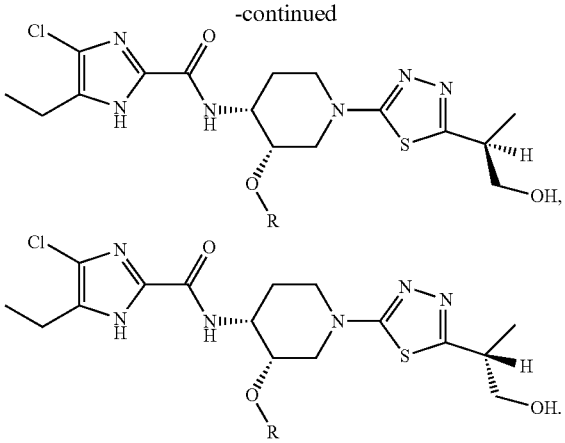

Some compounds as shown above showed polymorphic characters, hence it should be understood that the present invention encompasses polymorphic form in addition to every racemic, optically active, stereoisomeric form or mixtures thereof, which inhibits DNA gyrase GyrB subunit and/or topoisomerase IV ParE subunit.

In another embodiment, the present invention provides amorphous solid as exemplified in examples set out hereinafter, for instance, examples 1, 2, 3 and 4. Other polymorphic forms, for instance crystalline forms of examples 1, 2, 3 and 4 are also included within the scope of the present invention.

The optically active form can be prepared by methods known in the art, for example, i) resolution of the racemic form by recrystallization techniques, ii) synthesis from optically-active starting materials, iii) chiral synthesis, iv) enzymatic resolutions, v) bioconversion, or vi) chromatographic separation using a chiral stationary phase. Similarly, any method known in the art for measuring inhibitory effect for DNA gyrase GyrB subunit and/or topoisomerase IV ParE subunit can be employed including the method described hereinafter.

Next, a pharmaceutical composition comprising a compound of general formula (I), a stereoisomer, a polymorphic form, or pharmaceutically acceptable salt thereof is provided.

The compound of the present invention alone or in a form of pharmaceutical composition may be typically used to prevent or treat bacterial infections in animals including humans. Thus, for treating and preventing a suitable dosage form may be required. The suitable dosage forms will depend upon the use or route of administration. Techniques and formulations generally may be found in *The Science and Practice of Pharmacy*, 21$^{st}$ edition, Lippincott, Williams and Wilkins, Philadelphia, Pa., 2005 (incorporated herein by reference).

Thus, in another aspect, the present invention provides a pharmaceutical composition for use in treating bacterial infections in a warm-blooded animal such as human, wherein the composition comprises a compound of formula (I), a stereoisomer, a polymorphic form, or a pharmaceutically acceptable salt thereof, together with a pharmaceutically acceptable excipient or carrier.

The pharmaceutical composition of the present invention may be in a form suitable for oral use (e.g., tablets, lozenges, hard or soft capsules, aqueous or oily suspensions, emulsions, dispersible powders or granules, syrups and elixirs), topical use (e.g., creams, ointments, gels, and aqueous or oily solutions or suspensions), administration by an inhalation method (e.g., finely grained powders and liquid aerosols), administration by an aeration method (e.g., pulverized powders), or parenteral administration (e.g., sterile aqueous or oily solutions for intravenous, subcutaneous, or intramuscular administration and suppositories for rectal administration).

The pharmaceutical composition of the present invention can be obtained by conventional approaches using conventional pharmaceutical excipients well known in the art. Thus, the compositions intended for oral use may contain, for example, one or more coloring agent(s), sweetener(s), corrigent(s), and/or preservative(s).

Examples of pharmaceutically acceptable excipients suitable for tablet preparation include, but not limited to, inert diluents (e.g., lactose, sodium carbonate, calcium phosphate and calcium carbonate); granulating agents and disintegrants (e.g., corn starch and alginic acid); binders (e.g., starch); lubricants (e.g., magnesium stearate, stearic acid, and talc); preservatives (e.g., ethyl p-hydroxybenzoate and propyl p-hydroxybenzoate); and antioxidants (e.g., ascorbic acid).

The tablets so prepared may be uncoated or coated for altering their disintegration, and subsequent enteral absorption of the active ingredient, or for improving their stability and/or appearance. In both cases, conventional coating agents and approaches well known in the art can be employed.

The pharmaceutical compositions intended for oral use may be in a form of hard gelatin capsule. In this case, the active ingredient is mixed with an inert solid diluent, for example, calcium carbonate, calcium phosphate, or kaolin. Alternatively, for use as a soft gelatin capsule, the active ingredient is mixed with water or oil, for example, peanut oil, liquid paraffin, or olive oil.

The aqueous solutions generally comprise an active ingredient in a pulverized form, together with one or more suspending agent(s) (e.g., sodium carboxymethylcellulose, methylcellulose, hydroxypropylmethylcellulose, sodium alginate, polyvinylpyrrolidone, tragacanth gum, and gum arabic); and dispersant(s) or wetting agent(s) (e.g., lecithin, condensation products of alkylene oxides and fatty acids such as polyoxyethylene stearate), condensation products of ethylene oxide and long-chain aliphatic alcohols (e.g., heptadecaethylene oxycetanol), condensation products of ethylene oxide and partial esters derived from fatty acids and hexitols (e.g., polyoxyethylene sorbitol monooleate), condensation products of ethylene oxide and long-chain aliphatic alcohols (e.g., heptadecaethylene oxycetanol), condensation products of ethylene oxide and partial esters derived from fatty acids and hexitols (e.g., polyoxyethylene sorbitol monooleate), and condensation products of ethylene oxide and partial esters derived from fatty acids and hexitol anhydrides (e.g., polyethylene sorbitan monooleate).

The aqueous solutions may also contain one or more preservative(s) (e.g., ethyl p-hydroxybenzoate and propyl p-hydroxybenzoate), antioxidant(s) (e.g., ascorbic acid), coloring agent(s), corrigent(s), and/or sweetener(s) (e.g., sucrose, saccharine, and aspartame).

The oily suspensions may be prepared by suspending an active ingredient in a plant oil (e.g., peanut oil, olive oil, sesame oil, or coconut oil) or a mineral oil (e.g., liquid paraffin). The oily suspensions may also contain a thickener such as beeswax, solid paraffin, or cetyl alcohol. To provide palatable oral preparations, such sweetener(s) and corrigent(s) as described above may be added thereto. These compositions may be stored by adding thereto an antioxidant such as ascorbic acid.

The dispersible powders and granules suitable for producing aqueous suspensions by addition of water generally comprise the active ingredient, together with a dispersant or wetting agent, a suspending agent, and one or more preservative(s). Appropriate dispersants or wetting agents and suspending agents are as described above. Moreover, additional excipients such as sweeteners, corrigents, and coloring agents may be contained therein.

Moreover, the pharmaceutical compositions of the present invention may be in a form of water-in-oil emulsion. The oil phase can be a plant oil (e.g., olive oil or peanut oil) or a mineral oil (e.g., liquid paraffin), or any mixture thereof. Appropriate emulsifying agents can be, for example, naturally existing gums (e.g., gum arabic and tragacanth gum), naturally existing phosphatides (e.g., soybean and lecithin), esters or partial esters derived from fatty acids and hexitol anhydrides (e.g., sorbitan monooleate), and condensation products of the partial esters and ethylene oxide (e.g., polyoxyethylene sorbitan monolaurate). The emulsions may also contain a sweetener, a corrigent, and a preservative.

The syrups and the elixirs may be prepared together with a sweetener such as glycerol, propylene glycol, sorbitol, aspartame, or sucrose and may contain a demulcent, preservative, corrigent, and/or coloring agent.

The pharmaceutical composition may be in a form of sterile injectable. The injectables can be prepared according to known approaches using one or more of the appropriate dispersants or wetting agents and suspending agents described above.

Moreover, the sterile injectable formulations may be sterile injectable solutions or suspensions in a nontoxic, parenterally acceptable diluent or solvent, for example, 1,3-butanediol solutions.

The pharmaceutical compositions for use in administration by an inhalation method may be in a form of conventional pressurized aerosol that is adjusted to distribute an active ingredient either as an aerosol containing pulverized solid or as an aerosol containing liquid droplets. Conventional aerosol propellants such as volatile fluorinated hydrocarbons or hydrocarbons may be used. An aerosol apparatus is appropriately adjusted to distribute a constant amount of an active ingredient.

For further information about preparation, the reader may refer to chapter 25.2, Vol. 5, Comprehensive Medicinal Chemistry (Corwin Hansch; editor in chief; Pergamon Press, 1990).

The amount of an active ingredient contained together with one or more excipient(s) for producing one dosage form is inevitably predicted to vary according to the host to be treated and particular administration route. For example, a preparation intended for oral administration to a human is generally predicted to comprise, for example, 0.5 mg to 2 g of the active ingredient formulated together with an appropriate and convenient amount of excipient(s). In this context, the amount of excipients can vary within a range of, but not limited to, 5 to 98% by weight of total weight of a composition. A unit dosage form is generally predicted to comprise approximately 1 mg to approximately 500 mg of an active ingredient. For further information about administration routes and dose schedules, the reader may refer to Chapter 25.3, Vol. 5, Comprehensive Medicinal Chemistry (Corwin Hansch; editor in chief; Pergamon Press, 1990).

The pharmaceutical compositions of the present invention may also comprise, in addition to a compound disclosed herein, one or more known agent(s) selected from clinically useful antibacterial agents, for example, but not limited to, macrolide (e.g., erythromycin, telithromycin, dirithromycin, roxithromycin, clarithromycin, azithromycin or fidaxomicin), quinolone (e.g., ciprofloxacin, norfloxacin, levofloxacin, moxifloxacin or sitafloxacin), β-lactam (e.g., amoxicillin, cefalexin, cefaclor, cefuroxime, cefdaloxime, cefepime, ceftobiprole or cefetrizole), aminoglycosides (e.g., gentamicin, neomycin or streptomycin), and carbapenems (e.g., meropenem or imipenem) and/or other anti-infective agents (e.g., anti-fungal triazoles and amphotericin). Other active pharmaceutical agent which can be used in combination with compounds of the present invention include metronidazole and/or vancomycin. The other active agent may be co-administered with a compound of the present invention simultaneously, continuously, or separately. The use of such active agents can expand therapeutic effectiveness of a pharmaceutical composition of the present invention.

As described above, the magnitude of a dose necessary for therapeutic or preventive treatment of a particular condition is inevitably predicted to vary according to host to be treated, administration route, and severity of diseases to be treated. Preferably, the daily dose is used within the range of 1 to 50 mg/kg. However, the daily dose is inevitably predicted to vary according as described above. Thus, the optimum dose may be determined by any general practitioner that provides treatment to a patient.

In a particular embodiment, a pharmaceutical composition is provided to treat or prevent bacterial infectious diseases.

In another particular embodiment, a pharmaceutical composition is provided to treat or prevent bacterial infectious diseases caused by Gram-positive bacteria selected from genus *Staphylococcus, Streptococcus, Enterococcus, Clostridium, Bacillus, Corynebacterium,* and *Listeria* species.

In another particular embodiment, a pharmaceutical composition is provided to treat or prevent bacterial infectious diseases caused by resistant bacteria selected from methicillin-resistant *Staphylococcus aureus* (MRSA), penicillin-resistant *Streptococcus pneumoniae* (PRSP), and vancomycin-resistant *Enterococcus* (VRE).

In yet another particular embodiment, a pharmaceutical composition is provided to treat or prevent bacterial infectious diseases selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, gas gangrene, food poisoning, tetanus, botulism, diarrhea, pseudomembranous colitis, toxic mega colon, and perforation of colon.

As described, a compound of general formula (I) has therapeutic applications and may be used to treat or prevent bacterial infections.

Thus, the present invention in its another aspect provides a method for treating or preventing bacterial infection in a patient comprising the steps of administering to said patient a therapeutically effective amount of a compound of general formula (I), a stereoisomer, a polymorphic form, a hydrate, or a pharmaceutically acceptable salt thereof, or a pharmaceutical composition containing the same.

According to a further aspect, the present invention provides a compound represented by general formula (I) or a stereoisomer, a polymorphic form, or a pharmaceutically acceptable salt thereof, which is intended for use in treating bacterial infections in a patient.

According to a further aspect, the present invention provides a method for inhibiting bacterial DNA gyrase GyrB subunit and/or topoisomerase IV ParE subunit in a patient in need of antibacterial treatment. This method comprises administering an effective amount of a compound represented by general formula (I) or a stereoisomer, a polymorphic form, or a pharmaceutically acceptable salt thereof in a patient.

A further aspect of the present invention provides a compound represented by general formula (I) or a stereoisomer, a polymorphic form, or a pharmaceutically acceptable salt, which is intended for use as a pharmaceutical agent for producing antibacterial effect in a patient.

A further aspect of the present invention provides a compound represented by formula (I) or a stereoisomer, a polymorphic form, or a pharmaceutically acceptable salt, which is intended for use as a pharmaceutical agent for inhibiting bacterial DNA gyrase GyrB subunit and/or topoisomerase IV ParE subunit in a patient.

In one particular embodiment, there is provided a compound of formula (I), or a stereoisomer, a polymorphic form, or a pharmaceutically acceptable salt, which is intended for use as a pharmaceutical agent for treating bacterial infections in a patient.

According to a further aspect, the present invention provides use of a compound represented by general formula (I) or a stereoisomer, a polymorphic form, or a pharmaceutically acceptable salt, in the production of a pharmaceutical agent used for inhibiting bacterial DNA gyrase GyrB subunit and/or topoisomerase IV ParE subunit in a patient.

In a particular embodiment, the present invention provides use of a compound represented by general formula (I) or a stereoisomer, a polymorphic form, or a pharmaceutically acceptable salt, in the production of a pharmaceutical agent used for treating bacterial infections in a patient.

According to a further aspect, the present invention provides a compound represented by general formula (I) or a stereoisomer, a polymorphic form, or a pharmaceutically acceptable salt, which is intended for use for producing an antibacterial effect in a patient.

According to a further aspect, the present invention provides a compound represented by general formula (I) or a stereoisomer, a polymorphic form, or a pharmaceutically acceptable salt, which is intended for use for inhibiting bacterial DNA gyrase GyrB subunit and/or topoisomerase IV ParE subunit in a patient.

According to a particular embodiment, the present invention provides a compound represented by general formula (I) or a stereoisomer, a polymorphic form, or a pharmaceutically acceptable salt, which is intended for use for treating bacterial infections in a patient.

As used herein the term "therapeutically effective amount" refers to the amount of a compound of the present invention, when administered to a patient for treating or preventing bacterial infections, is sufficient to effect such treatment or prevention.

As used herein the term "patient" refers to a subject such as human suffering from bacterial infections as defined hereinafter and needs therapeutic intervention for the treatment and/or prevention of such bacterial infections.

As used herein the term "bacterial infections" refer to infections caused by Gram-positive, and Gram-negative bacteria including resistant bacteria thereof. The most common organisms include *Staphylococcus, Streptococcus, Enterococcus, Clostridium, Bacillus, Corynebacterium, Haemophilus* and *Listeria* species. The diseases caused by said bacteria include, but not limited to, pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, and perforation of colon.

In another embodiment of the present invention, there is provided a method for treating infectious diseases especially caused by a pathogen selected from methicillin-resistant *Staphylococcus aureus* (MRSA), penicillin-resistant *Streptococcus pneumoniae* (PRSP), and vancomycin-resistant *Enterococcus* (VRE), and *Clostridium difficile*.

MRSA is a bacterium that is resistant to common antibiotics like penicillin. It can cause skin, bloodstream and surgical wound infections and pneumonia. Compounds disclosed herein are superior to linezolid in terms of in vitro antibacterial activity, efficacy and Frequency of Resistance.

*Clostridium difficile* infection (CDI) is an intestinal disease caused by an anaerobic bacteria *C. difficile* which colonizes in colon. *C. difficile* produces spore and toxins which are responsible for its pathogenesis. The clinical symptoms due to CDI are diarrhea and abdominal pain and in severe cases pseudomembranous colitis, toxic mega colon, and death. Frequent recurrence is also very common even after successful treatment due to the formation of spores. CDI incidences are increasing worldwide. CDI-related death has increased due to the spread of a hyper virulent NAP1/027 strain in the US and Europe.

The compounds of the present invention are active against hypervirulent NAP1/027 strains, hence provide opportunity to treat bacterial infections such as MRSA and CDI.

Accordingly, the present invention provides compounds for use in the treatment of MRSA infections, community-acquired respiratory infections, *Clostridium difficile* infections and clinical symptoms thereof such as diarrhea, pseudomembranous colitis, toxic mega colon, perforation of colon and sepsis.

In another embodiment of the present invention, there is provided a method for treating infectious diseases caused by MRSA.

In another embodiment of the present invention, there is provided a method for treating CDI.

In another embodiment of the present invention, there is provided a method for treating infectious diseases caused by PRSP and VRE.

*Haemophilus influenzae*, a gram negative bacteria, can cause many kinds of infections including, but not limited to, ear infections, bacteremia, community-acquired respiratory infections, pneumonia and acute bacterial meningitis. Surprisingly, the compounds of the present invention were found to be very active against this pathogen, and hence can be employed for the treatment of said infections caused by *Haemophilus influenzae*.

Accordingly, the present invention provides compounds for use in the treatment of diseases such as community-acquired respiratory infections, pneumonia, bacteremia and acute bacterial meningitis caused *Haemophilus influenzae*.

*Propionibacterium acnes*, a gram-positive human skin commensal that prefers anaerobic growth conditions and is involved in the pathogenesis of acne, can cause skin disease such as acne vulgaris, which is the most commonly associated with *P. acnes* infection. In addition, *P. acnes* have been associated with endocarditis of prosthetic and native aortic valves, corneal infections and postoperative endophthalmitis. It has also been recognized as a source of infection in focal intracranial infections and various cerebrospinal fluid shunt infections. Surprisingly, the compounds of the present invention were found to be very active against this pathogen, and hence can be employed for the treatment of said infections, preferably acne vulgaris.

*Neisseria gonorrhoeae*, a gram-negative bacterium, can cause gonorrhoea, which is the most common disease associated with *N. gonorrhoeae*. In addition, *N. gonorrhoeae* can also cause conjunctivitis, pharyngitis, proctitis, urethritis, prostatitis or orchitis. Surprisingly, the compounds of the present invention were found to be very active against this pathogen, and hence can be employed for the treatment of said infections, preferably *gonorrhoea*.

In one particular embodiment, there is provided compounds for use in the treatment of diseases, but not limited to, community-acquired respiratory infections, hospital-acquired infections, urinary tract infections, acne vulgaris, gonorrhoea and *Clostridium difficile* infections.

Next, general methods of preparation of a compound of the present invention will be provided.

In general, a compound of the present invention can be prepared by following general scheme and experimental procedures described hereinafter and/or by additional or alternative known processes and procedures in combination with knowledge of ordinary skill in the art. It should be understood that the methods set forth in the following general scheme are intended for illustrative purposes and are not to be construed as limiting the scope of the disclosure.

Thus, in another aspect, the present invention provides synthetic methods for producing a compound represented by general formula (1) or a pharmaceutically acceptable salt thereof.

In Scheme 1, a general method of preparation of compounds of the present invention is provided.

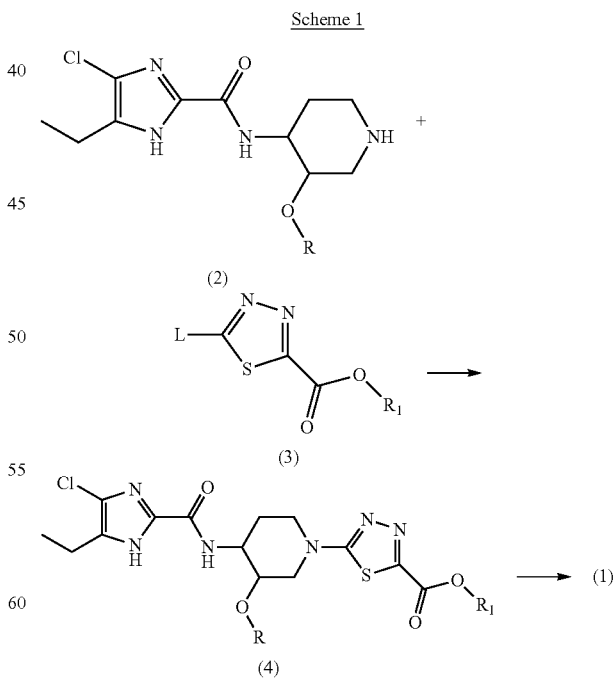

The compound of general formula (1) can be prepared by following the steps of Scheme 1. In a first step, a nucleophilic substitution reaction of a compound of formula (2) with (3) (wherein L represents a suitable leaving group such as halogen selected from fluorine, chlorine, bromine, or iodine; $R_1$ represents alkyl group) is carried out with heating in a suitable solvent such as dimethylformamide in the presence of a base such as diisopropylethylamine to obtain a compound of formula (4). In a second step, the ester group of intermediate compound of formula (4) is converted into a compound of general formula (I): (a) by alkylation (Grignard reaction), when A in general formula (I) is

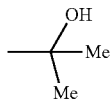

in a suitable solvent such as tetrahydrofuran in the presence of a methyl metal compound such as methylmagnesium bromide (in tetrahydrofuran) at or below 20° C., more preferably at or below 0° C. (b) by reduction, oxidation, followed by alkylation, when A in general formula (I) is

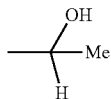

wherein, the reduction of a compound of formula (4) is carried out at room temperature in a suitable solvent such as methanol in the presence of a reducing agent such as sodium borohydride to obtain an alcohol intermediate, which upon oxidation at room temperature in a suitable solvent such as methylene chloride in the presence of an oxidizing agent such as manganese dioxide gives an aldehyde intermediate, which is finally subjected to alkylation (Grignard reaction) as described above.

The compound represented by formula (3) is commercially available, already known in literature, or synthesized by standard synthetic methods well known in the art.

The compound represented by formula (2) can be prepared following the reaction sequence as depicted below:

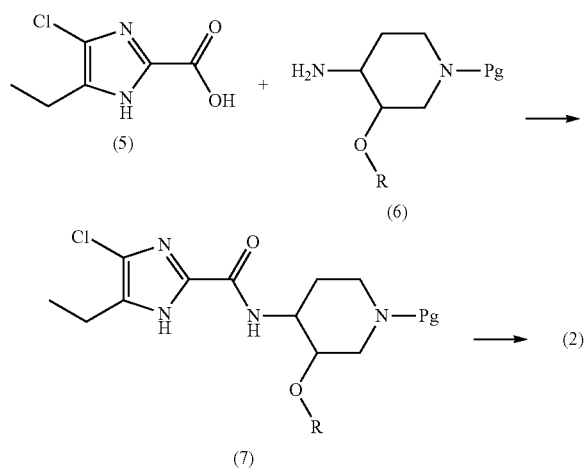

The intermediate compound of formula (2) can be prepared by condensation reaction, followed by deprotection. Firstly, an imidazole compound of formula (5) is condensed with a compound of formula (6) (wherein R is as defined above, and Pg is a protecting group such as tert-butyloxycarbonyl, methoxycarbonyl, ethoxycarbonyl or p-methoxy benzyl) in the presence of a suitable peptide coupling reagent known in the art, or a coupling agent such as 1-ethyl-3-(3-dimethylaminopropyl) carbodiimide hydrochloride (EDCl). Such a condensation reaction is sometimes carried out in the presence of a catalyst such as 1-hydroxybenzotriazole (HOBT) or dimethylamino pyridine, and sometimes in the presence of a base such as triethylamine or di-isopropylethylamine, in a suitable solvent such as dichloromethane, tetrahydrofuran, N,N-dimethylacetamide and dimethylformamide, and in a temperature range of −40° C. to 80° C.

In a second step, the compound of formula (7) is subjected to deprotection reaction in a suitable solvent such as methanol, in the presence of an acid such as a hydrogen chloride in ethyl acetate.

The imidazole compound of formula (5) is known in the literature (WO 2009/084614). The compound of formula (6) is commercially available or known in the literature. It can also be synthesized following procedure described in the art, for example WO 2006/087543.

In certain cases, optically pure compound of formula (6) can be prepared by following procedures described hereinafter.

A methylated derivative of the compound represented by formula (3) such as (3a), a dimethylated compound, or (3b), a monomethylated compound, is preferably employed as synthetic intermediates for compound (I).

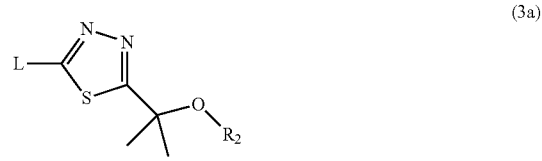

(3a)

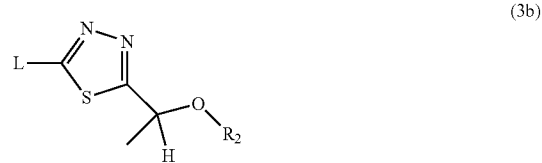

(3b)

Under these circumstances, the methylated compound of formula (4) such as (4a) or (4b) is directly prepared, which avoids alkylation step as shown in scheme 1 above.

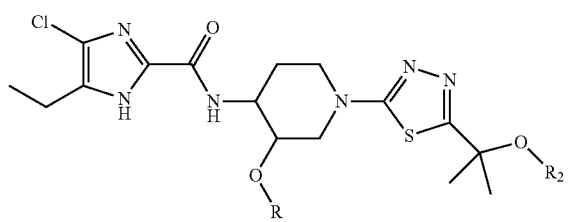

(4a)

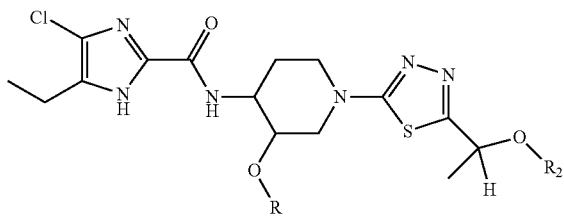

(4b)

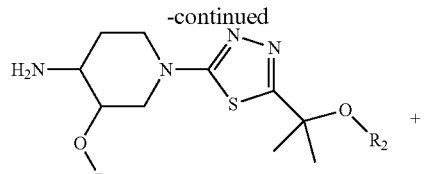

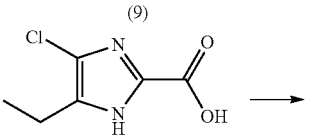

(5)

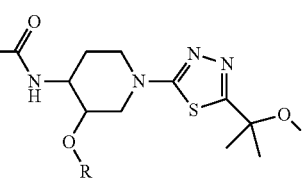

(4a)

The use of a compound (3a) or (3b) is advantageous as it enables to avoid contamination of carbonyl impurity at the alkylation step of the compound of formula (4).

More specifically, the bromo-derivative of (3a) or (3b), wherein L in the formula (3a) or (3b) is bromine, is preferably used for the reaction. The bromo-derivative of (3a) or (3b) is obtained by the reaction of corresponding amino-derivative of compound (3a) or (3b), wherein L in the formula (3a) or (3b) is —$NH_2$, by the bromination of diazonium compound obtained by reacting sodium nitrite with the amino compound of (3a) and (3b) according to the known method. The amino-derivative of compound (3a) or (3b) is obtained by the reaction of hydrazinecarbothioamide and 2-($R_2$—O—)-2-methylpropionic acid or 2-($R_2$—O—)— propionic acid in the presence of phosphorous chlorinating agent such as phosphorous oxy chloride, phosphorous pentachloride, phosphorous trichloride and the like. Any solvent which does not interfere with the reaction can be employed for this reaction, and ether such as dioxane, 1,2-dimethoxyethane; hydrocarbon such as benzene, toluene, xylene; halogenated hydrocarbon such as chloroform, 1,2-dichloethane; ester such as ethyl acetate, propyl acetate, butyl acetate are exemplified. With regard to the ($R_2$—O—)— moiety of 2-($R_2$—O—)— 2-methylpropionic acid ester or 2-($R_2$—O—)-propionic acid ester, this moiety is preferably those derived from the protection of hydroxy group of 2-hydroxy-propionic ester by some protective group for hydroxy group. Such protective group for hydroxy group may be selected from those known in the art; alkyl group such as methyl group, tert-butyl group; aralkyl group such as benzyl group, p-methoxy benzyl group; acyl group such as acetyl group, pivaloyl group, benzoyl group are exemplified. As for the ($R_2$—O—)— moiety, acyloxy group is preferably employed and benzoyloxy group is more preferable used. The deprotection of the protective group $R_2$ are able to be conducted by the known method corresponding to the protective group actually selected to yield hydroxy group. The reaction of bromo-derivative of (3a) or (3b) with compound (2) is conducted according to the method explained above.

Preferably, the compound of formula (1) is obtained according to Scheme 2, using a bromo-derivative of a compound (3a) or (3b), wherein L is bromine.

Scheme 2

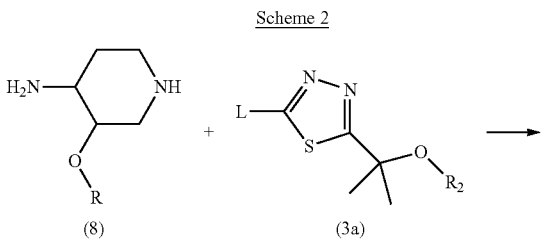

According to this process, thiadiazole moiety is introduced before the introduction of imidazole moiety. The compound of formula (9), specifically a dimethylated derivative, is obtained by the reaction of compound (3a) and compound (8). The resulting compound (9), especially a dimethylated derivative, was obtained as a solid salt of carboxylic acid and such a carboxylic acid salt was purified by a method well known in the relevant art, such as slurry method or recrystallization. As for the salt of compound (9) with carboxylic acid, propionic acid salt is preferably exemplified. This is very advantageous as high purity compound (9) can be obtained to be used as the synthetic intermediate, which can enable to obtain high purity of compound of formula (I). Free form of compound (9) can be obtained by a known method such as treatment of salt of compound (9) with a base. The reaction of compound (3a) and compound (8) is achieved by the condition explained above.

Compound (9), a dimethylated derivative, can be converted to compound (4a) by the reaction of compound (9) and 4-chloro-5-ethyl-1H-imidazole-2-carboxylic acid (5). This reaction can be achieved under the condition explained later. The removal of $R_2$ from compound (4a) yields compound (I). This removal can be achieved by known method according to $R_2$, a protective group, being employed.

The methods described herein intend to preferably include the following embodiments, for example, with regard to preparation of 5-(2-hydroxypropan-2-yl)-1,3,4-thiadiazol-2-yl derivative having the following formula or a stereoisomer thereof

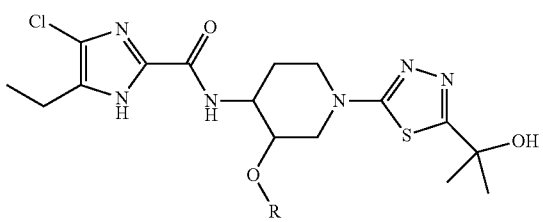

there is provided a method, which comprises di-methylation on carbonyl carbon atom of —C(═O)—O—$R_1$ of the compound of the following formula or a stereoisomer thereof:

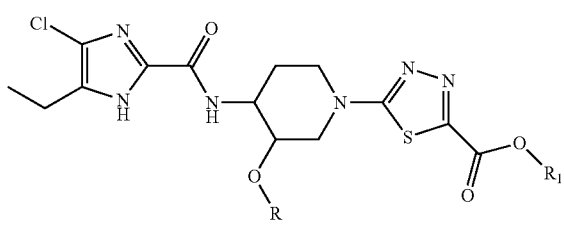

wherein, R represents ($C_1$-$C_3$) alkyl group and $R_1$ represents an alkyl group.

In another embodiment, there is provided a method for the preparation of a compound of the following formula or a stereoisomer thereof

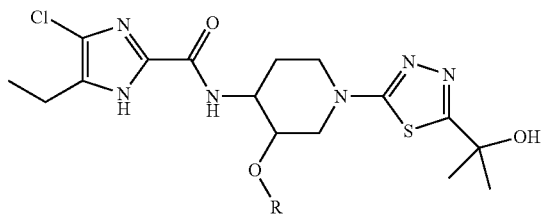

which method comprises the steps of:
i) reacting a compound of the following formula or a stereoisomer thereof:

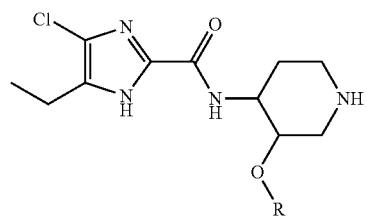

with a compound of the following formula:

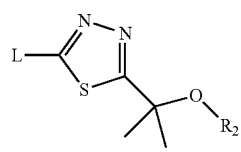

wherein L represents a leaving group, $R_2$ represents a protective group for hydroxy group, and R represents ($C_1$-$C_3$) alkyl group, to obtain a compound of the following formula or a stereoisomer thereof

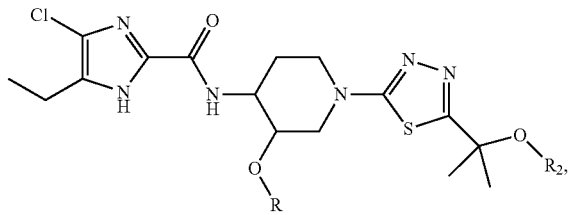

and
ii) deprotecting the compound obtained in step i).

In another embodiment, there is provided a method for the preparation of a compound of the following formula or a stereoisomer thereof:

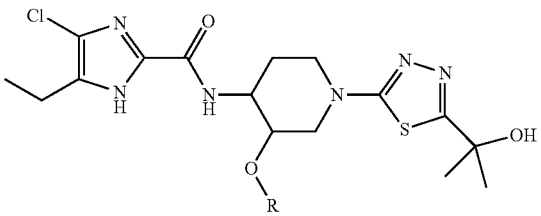

which method comprises the steps of:
i) reacting a compound of the following formula or a stereoisomer thereof:

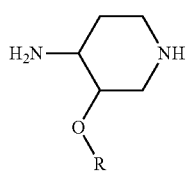

with a compound of the following formula:

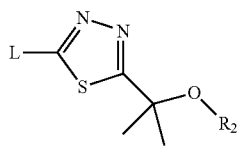

to obtain a compound of the following formula or a stereoisomer thereof

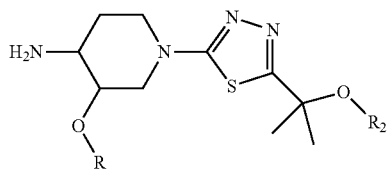

ii) the compound obtained in step i) is reacted with a compound of the following formula:

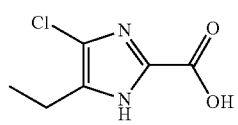

to obtain a compound of the following formula or a stereoisomer thereof:

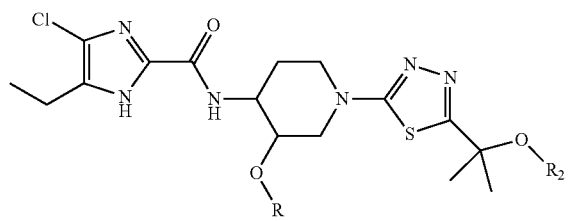

and then iii) deprotecting the compound obtained in step ii), wherein L, R and $R_2$ are as defined hereinbefore.

In a preferred embodiment, the compound obtained by any of the methods described above has the following structure formula:

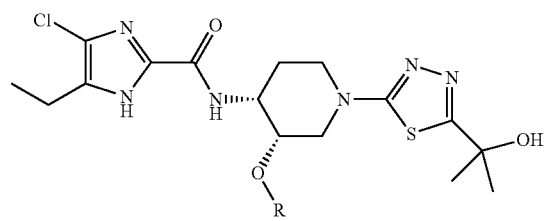

With regard to preparation of 5-(1-hydroxyethyl)-1,3,4-thiadiazol-2-yl derivative having the following formula or a stereoisomer thereof

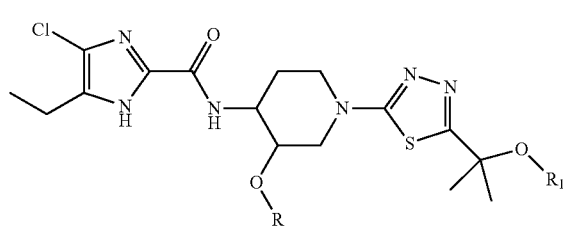

there is provided a method, which comprises the steps of:
i) reducing a compound of the following formula or a stereoisomer thereof:

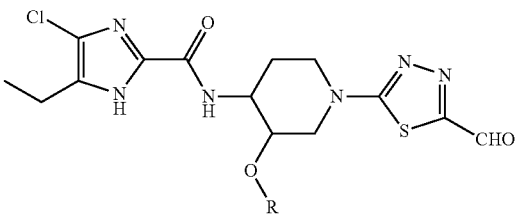

in presence of a suitable reducing agent such as sodium borohydride to obtain a compound of the following formula or a stereoisomer thereof:

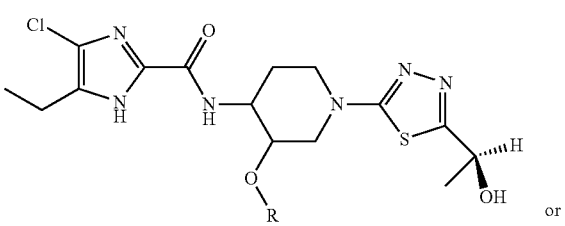

ii) oxidizing a compound obtained in step i) using a suitable oxidizing agent to obtain a compound of the following formula or a stereoisomer thereof:

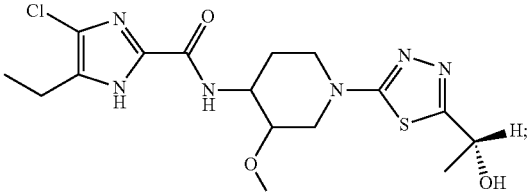

and iii) methylating on the carbon atom of formyl group with Grignard reagent.

In a preferred embodiment, the compound, obtained by following methods described above, has the following structural formula:

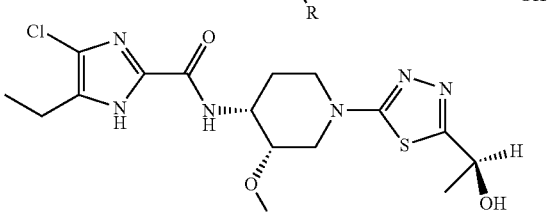

or

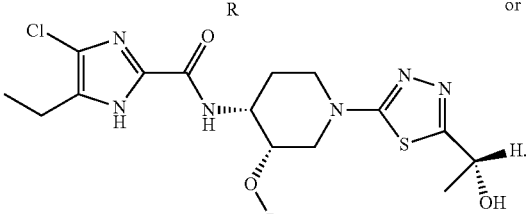

With regard to preparation of 5-(1-hydroxypropan-2-yl)-1,3,4-thiadiazol-2-yl derivative having the following formula or a stereoisomer thereof

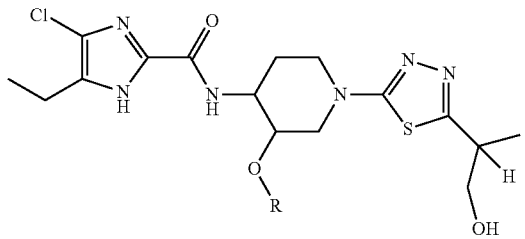

there is provided a method, which comprises reacting a compound of the following formula or a stereoisomer thereof

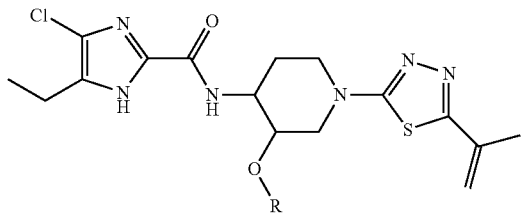

with borane, followed by treatment with hydrogen peroxide.

In a preferred embodiment, the compound obtained following the above method has a structural formula:

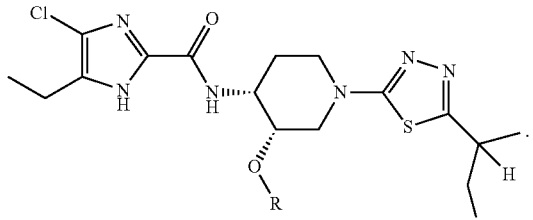

With regard to preparation of 5-[1,2-dihydroxyethyl]-1,3,4-thiadiazol-2-yl derivative having the following formula or a stereoisomer thereof:

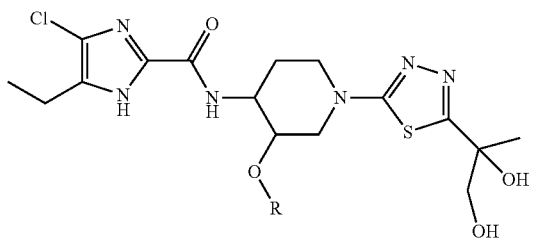

there is provided a method, which comprises dihydroxylating a compound (on-5-ethenyl group of 1,3,4-thiadiazole) of the following formula or a stereoisomer thereof

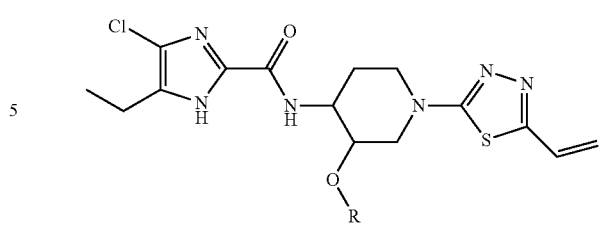

wherein dihydroxylation is Sharpless asymmetric dihydroxylation.

In a preferred embodiment, the compound obtained by following above method has the structural formula:

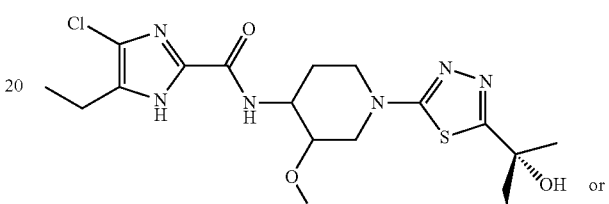

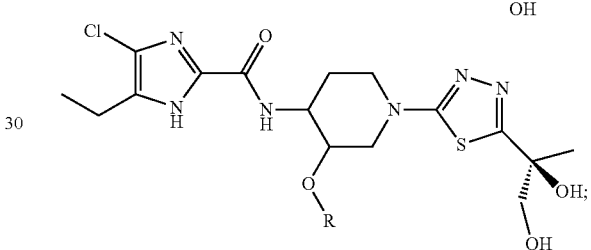

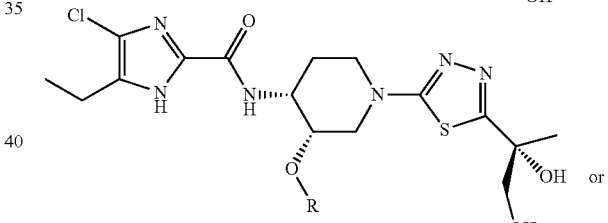

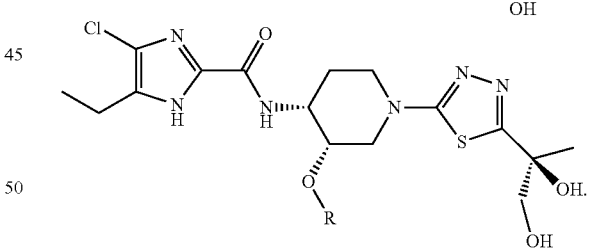

Synthetic methods routinely used by usual organic chemists for producing the pharmaceutically acceptable salts are within the scope of this patent application.

Skilled organic chemists can presumably obtain necessary starting materials and products by using reference documents described below, examples described therein, examples described hereinafter. When starting materials necessary for such approaches as described above are not commercially available, they may be prepared by an approach selected from standard organic chemical techniques similar to the synthesis of structurally similar compounds, and techniques similar to approaches of procedures described above or in examples.

It should be noted that many starting materials for the synthesis methods are commercially available and/or have been reported widely in scientific documents or can be formed from commercially available products by appropriately using synthetic methods reported in scientific documents. As a general guide to reaction conditions or reagents, see Advanced Organic Chemistry, Vol. 4 (Jerry March, ed., published by John Wiley and Sons, 1992).

In certain embodiments, it is to be understood that in place of reducing agent, solvent, protecting groups, organolithium reagents, and base, optionally indicated in one or more methods described herein, any other reducing agent, solvent, protecting agent, organolithium reagents, and base, as described herein, can also be employed.

Conventional protecting groups can be used according to standard techniques (for the illustrative purpose, see T. W. Greene, Protective Groups in Organic Synthesis, John Wiley and Sons, 1991).

Examples of a protecting group suitable for amino group include acyl groups such as alkanoyl groups (e.g., acetyl), alkoxycarbonyl groups (e.g., methoxycarbonyl, ethoxycarbonyl, and tert-butoxycarbonyl), arylmethoxycarbonyl groups (e.g., benzyloxycarbonyl), and aroyl groups (e.g., benzoyl) or p-methoxybenzyl.

Deprotection conditions for the protecting groups inevitably vary according to the selection of the protecting groups. Thus, for example, acyl groups such as alkanoyl or alkoxycarbonyl groups or aroyl groups may be removed, for example, by hydrolysis with an appropriate base such as an alkali metal hydroxide (e.g., lithium hydroxide or sodium hydroxide). Alternatively, alkoxycarbonyl groups (e.g., a tert-butoxycarbonyl group) may be removed, for example, by treatment with an appropriate acid such as hydrochloric acid, sulfuric acid, phosphoric acid, or trifluoroacetic acid. Arylmethoxycarbonyl groups (e.g., a benzyloxycarbonyl group) may be removed, for example, by treatment with hydrogen in the presence of a palladium-supported catalyst (e.g., active carbon) or by treatment with a Lewis acid, for example, boron tris(trifluoroacetate).

Examples of the protecting groups suitable for the carboxyl group include esterifiable substituents, for example, methyl, ethyl, tert-butyl, and benzyl groups.

Deprotection conditions for the protecting groups are inevitably predicted to vary according to the selection of the protecting groups.

Thus, for example, a methyl ester or ethyl ester group may be removed, for example, by hydrolysis with an appropriate base such as sodium hydroxide. For example, a tert-butyl ester group may be removed, for example, by treatment with an organic acid such as trifluoroacetic acid. A benzyl ester group may be removed, for example, by the hydrogenolysis in the presence of a palladium-supported catalyst (e.g., active carbon).

These protecting groups may be removed at any convenient stage of synthesis using conventional techniques well known in the chemical field. Alternatively, the protecting groups may be removed in subsequent reaction steps or during workup. The removal of every protecting group and the formation of a pharmaceutically acceptable salt are within the ability of usual organic chemists to use standard techniques.

When an optically active form of a compound of the present invention is required, this form may be obtained by subjecting an optically active starting material (e.g., formed by asymmetric derivatization in an appropriate reaction step) to any one of the approaches described above; or by resolving a racemic form of the present compound or an intermediate thereof using standard procedures; or by separating a diastereoisomer, if formed, by chromatography. Moreover, enzymatic techniques can also be useful in the production of the optically active compound and/or intermediate.

Likewise, when a pure diastereomer of a compound of the present invention is required, this isomer may be obtained by subjecting a purified diastereomer mixture as a starting material to any one of the approaches described above or by resolving a mixture of diastereomer or intermediates thereof using standard procedures.

The yield is shown only as an example, and is not always necessarily the maximum value achievable.

The structure of a final product of the present invention was generally determined by NMR (referred to the proton magnetic resonance spectrum) and/or mass spectrum (ESI method, APCI method or FAB method). The chemical shift in the proton magnetic resonance ($^1$H-NMR) spectrum is expressed in ppm in a lower magnetic field (δ scale) relative to tetramethylsilane as the internal standard, and the coupling constant (J) and the peak multiplicity are denoted as follows (s, singlet; d, doublet; dd, doublet of doublet; dt, triplet of doublet; t, triplet; q, quartet; m, multiplet; br, broad). Cation data and anion data are incorporated into mass spectrum as necessary by ESI method, APCI method or FAB method. The measurement was carried out at a rotation angle of 589 nm (25° C.).

Each intermediate is purified and structurally determined to a level required in subsequent steps (the purity is evaluated by TLC or NMR to suitably determine the identity by mass spectrum or NMR spectrum).

In the notation of the compound names, it should be understood that cis (±) or trans (±), when used, means a racemic mixture of cis or trans isomers, and (−) or (+), when referred, means a single enantiomer as in R, R or S, S.

As a reducing agent, unless otherwise indicated, a hydrogenated complex compound, a boron-containing compound such as sodium borohydride, sodium triacetoxy borohydride or sodium cyano borohydride can be used. In addition, catalytic reduction using a metal catalyst such as palladium carbon, Raney nickel, platinum oxide, palladium hydroxide or palladium black can preferably be used.

According to the present invention, the solvents, unless otherwise indicated, include polar and non-polar solvents well known in the art including polar aprotic and polar protic solvents. The examples of polar solvents include, but are not limited to, methanol, ethanol, isopropyl alcohol, tert-butanol, n-butanol, acetic acid, formic acid or water, or aprotic solvent such as tetrahydrofuran, acetonitrile, dioxane, methylene chloride, dimethylsulfoxide, acetone, N,N-dimethylformamide, N,N-dimethylacetamide, ethyl acetate, 1,2-dimethoxyethane, 1,2-dichloroethane, chloroform or pyridine. Polar solvent also include a mixture of water with any of the above, or a mixture of any two or more of the above solvents. The examples of non-polar solvents include, but are not limited to, toluene, benzene, chlorobenzene, xylenes and hexanes.

Base, unless otherwise indicated, includes, but are not limited to, potassium hydroxide, sodium hydroxide, potassium carbonate, sodium carbonate, cesium carbonate, magnesium carbonate, barium carbonate, methylamine, triethylamine, diisopropylethylamine or pyridine.

In certain embodiments, the present invention encompasses isotopically labeled compounds of general formula (I). All isotopes of any particular atom or element as specified are contemplated within the scope of the present invention. The examples of isotopes that can be incorporated into compounds of the present invention include, but are not limited to, isotopes of hydrogen (e.g., $^2$H or $^3$H), carbon (e.g., $^{13}$C or $^{14}$C), nitrogen (e.g., $^{13}$N or $^{15}$N), oxygen (e.g., $^{15}$O, $^{17}$O or $^{18}$O), phosphorous (e.g., $^{32}$P or $^{33}$P), sulphur (e.g., $^{35}$S), halogen (e.g., $^{18}$F, $^{36}$Cl, $^{123}$I or $^{125}$I). In a preferred embodiment, the present invention provides deuterium (D or $^2$H) compounds of general formula (I). Isotopically labeled compounds of formula (I) can be prepared by following general scheme and methods thereof using isotopically labeled reagents. Isotopically labeled of the present invention may be useful in compound and/or substrate tissue distribution assays. Such applications of isotopically labeled compounds are well known to person skill in the art, and are therefore within the scope of the present invention.

The following abbreviations may sometimes be used. TLC means thin layer chromatography; DMF means N,N-dimethylformamide; THF means tetrahydrofuran; HOBT means 1-hydroxybenzotriazole; EDCl means 1-ethyl-3-(3-dimethylaminopropyl)carbodiimide hydrochloride; DMSO-D6 means deuterated dimethyl sulfoxide; CDCl$_3$ means deuterated chloroform; CD$_3$OD means deuterated methanol; FAB means high-speed atomic collision ionization; ESI means electrospray ionization; APCI means atmospheric pressure chemical ionization.

Experimental Procedures

Hereinafter, the present invention is described in detail with reference to examples and test examples, but the scope of the preset invention is not limited thereto. Any modification in the procedures described herein, other synthetic procedures and modification thereon can be employed or adapted. All such modifications and alternative procedures are within the spirit and scope of the present application.

Example 1

Synthesis of 4-chloro-N-{(3S,4R)-3-ethoxy-1-[5-(1-hydroxyethyl)-1,3,4-thiadiazol-2-yl]piperidin-4-yl}-5-ethyl-1H-imidazole-2-carboxamide (Exemplified Compound No. 1)

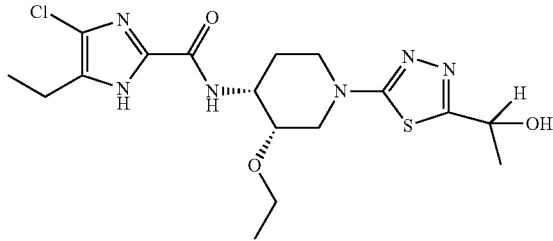

Step 1: Synthesis of tert-butyl (3R,4S)-4-{[(benzyloxy)carbonyl]amino}-3-ethoxypiperidine-1-carboxylate Tert-butyl cis(±)-4-{[(benzyloxy)carbonyl]amino}-3-ethoxypiperidine-1-carboxylate (200 g, 528 mmol) synthesized by the method described in the literature (WO 2009/084614) was optically resolved using an optically active column (CHIRALPAK IC®, elution solvent: hexane/2-propanol=80/20 (v/v)). The first-eluting peak compound (96.7 g) and the second-eluting peak compound (94.8 g) were obtained as colorless oily substances.

$^1$H-NMR (400 MHz, CDCl$_3$) δ ppm: 7.33-7.38 (5H, m), 5.17-5.24 (1H, m), 5.10 (2H, s), 4.28-4.40 (1H, m), 4.00-4.18 (1H, m), 3.68-3.76 (2H, m), 3.39-3.42 (1H, m), 3.32 (1H, dq, J=8.71, 7.34 Hz), 2.71-2.77 (2H, m), 1.62-1.78 (2H, m), 1.45 (9H, s), 1.14-1.18 (3H, m).

Step 2: Synthesis of tert-butyl (3S,4R)-4-{[(4-chloro-5-ethyl-1H-imidazol-2-yl)carbonyl]amino}-3-ethoxypiperidine-1-carboxylate 10% Palladium-carbon (1.3 g) was added to a solution of the first-eluting peak compound obtained in Step 1 (3.58 g, 9.47 mmol) in methanol (50 mL), and the mixture was stirred under a hydrogen atmosphere at room temperature for 1 hour and 40 minutes. Palladium-carbon was filtered through celite® and the filtrate was concentrated under reduced pressure to obtain crude tert-butyl (3S,4R)-4-amino-3-ethoxypiperidine-1-carboxylate as a colorless oily substance.

4-Chloro-5-ethyl-1H-imidazole-2-carboxylic acid (1.82 g, 10.4 mmol) synthesized by the method described in the literature (WO 2009/084614), WSC (4.79 g, 25 mmol) and HOBt (1.76 g, 13 mmol) were added to a solution of the crude tert-butyl (3S,4R)-4-amino-3-ethoxypiperidine-1-carboxylate obtained above in dimethylacetamide (50 mL), and the mixture was stirred at 70° C. for 1 hour. The reaction solution was diluted with ethyl acetate, washed with water 3 times and with brine and dried over anhydrous magnesium sulfate. The solvent was evaporated under reduced pressure, and the resulting residue was purified by silica gel column (ethyl acetate-hexane) to obtain the title compound (3.4 g, 90%) as a colorless amorphous solid.

$^1$H-NMR (400 MHz, CDCl$_3$) δ ppm: 11.92 (1H, s), 7.55 (1H, s), 4.05-4.52 (3H, m), 3.60-3.70 (1H, m), 3.41-3.49 (1H, m), 3.27 (1H, dt, J=8.71, 6.42 Hz), 2.71-2.86 (2H, m), 2.69 (2H, q, J=7.79 Hz), 1.85-1.94 (1H, m), 1.57-1.67 (1H, m), 1.47 (9H, s), 1.26 (3H, t, J=7.79 Hz), 0.92-0.99 (3H, m).

Step 3: Synthesis of ethyl 5-[(3S,4R)-4-{[(4-chloro-5-ethyl-1H-imidazol-2-yl)carbonyl]amino}-3-ethoxypiperidin-1-yl]-1,3,4-thiadiazole-2-carboxylate A hydrogen chloride/ethyl acetate solution (4N, 30 mL) was added to a solution of tert-butyl (3S,4R)-4-{[(4-chloro-5-ethyl-1H-imidazol-2-yl)carbonyl]amino}-3-ethoxypiperidine-1-carboxylate (3.4 g, 8.5 mmol) obtained in Step 2 in dichloromethane (20 mL), and the mixture was allowed to stand at room temperature for 30 minutes. The solvent was evaporated under reduced pressure to obtain crude 4-chloro-N-[(3S,4R)-3-ethoxypiperidin-4-yl]-5-ethyl-1H-imidazole-2-carboxamide hydrochloride as a colorless amorphous solid.

A solution of the crude 4-chloro-N-[(3S,4R)-3-ethoxypiperidin-4-yl]-5-ethyl-1H-imidazole-2-carboxamide hydrochloride obtained above, ethyl 5-bromo-1,3,4-thiadiazole-2-carboxylate (2.01 g, 8.5 mmol) and sodium bicarbonate (1.68 g, 20 mmol) in dimethylacetamide (40 mL) was stirred at 70° C. for 1 hour. The reaction solution was diluted with ethyl acetate, washed with water and brine, and dried over anhydrous magnesium sulfate. The solvent was evaporated under reduced pressure, and the resulting residue was purified by silica gel column (ethyl acetate-hexane) to obtain the title compound (3.75 g, 97%) as a colorless solid.

$^1$H-NMR (400 MHz, DMSO-D$_6$) δ ppm: 7.67 (1H, d, J=8.59 Hz), 4.35 (2H, q, J=7.16 Hz), 4.26-4.17 (2H, m), 4.05-3.97 (1H, m), 3.70-3.40 (5H, m), 2.55 (2H, q, J=7.45

Hz), 1.95-1.88 (1H, m), 1.72-1.68 (1H, m), 1.31 (3H, t, J=7.16 Hz), 1.14 (3H, t, J=7.45 Hz), 1.03 (3H, t, J=7.16 Hz).

Step 4: Synthesis of 4-chloro-N-{(3S,4R)-3-ethoxy-1-[5-(hydroxymethyl)-1,3,4-thiadiazol-2-yl]piperidin-4-yl}-5-ethyl-1H-imidazole-2-carboxamide Sodium borohydride (0.5 g, 13.3 mmol) was added to a solution of ethyl 5-[(3S,4R)-4-{[(4-chloro-5-ethyl-1H-imidazol-2-yl)carbonyl]amino}-3-ethoxypiperidin-1-yl]-1,3,4-thiadiazole-2-carboxylate obtained in Step 3 (0.95 g, 2.08 mmol) in methanol (30 mL), and the mixture was stirred at room temperature for 40 minutes. Water was added and the extraction was carried out with ethyl acetate. Following concentration under reduced pressure, and the resulting residue was purified by silica gel column to obtain the title compound (0.75 g, 87%) as a colorless amorphous solid.

$^1$H-NMR (400 MHz, CDCl$_3$) δ ppm: 11.12 (1H, s), 7.50 (1H, d, J=8.75 Hz), 4.88 (2H, d, J=5.73 Hz), 4.36-4.33 (1H, m), 4.26-4.21 (1H, m), 3.93-3.88 (1H, m), 3.73 (1H, dq, J=8.88, 7.15 Hz), 3.63-3.61 (1H, m), 3.44 (1H, dq, J=8.88, 7.15 Hz), 3.31-3.18 (2H, m), 2.74 (1H, t, J=5.73 Hz), 2.70 (2H, q, J=7.45 Hz), 2.15-2.10 (1H, m), 1.80-1.76 (1H, m), 1.27 (3H, t, J=7.45 Hz), 1.16 (3H, t, J=7.16 Hz).

Step 5: Synthesis of 4-chloro-N-{(3S,4R)-3-ethoxy-1-[5-(1-hydroxyethyl)-1,3,4-thiadiazol-2-yl]piperidin-4-yl}-5-ethyl-1H-imidazole-2-carboxamide Manganese dioxide (3.5 g) was added to a solution of the 4-chloro-N-{(3S,4R)-3-ethoxy-1-[5-(hydroxymethyl)-1,3,4-thiadiazol-2-yl]piperidin-4-yl}-5-ethyl-1H-imidazole-2-carboxamide (0.7 g) obtained in Step 4 in THF (20 mL), and the mixture was stirred at room temperature for 1 hour. After filtering through celite®, the reaction solution was concentrated under reduced pressure to obtain crude 4-chloro-N-[(3S,4R)-3-ethoxy-1-(5-formyl-1,3,4-thiadiazol-2-yl)piperidin-4-yl]-5-ethyl-1H-imidazole-2-carboxamide (0.68 g, 97%) as a colorless amorphous solid.

Methylmagnesium bromide (1.1 mol/L THF solution, 17 mL, 19 mmol) was added under ice-cooling to a solution of crude 4-chloro-N-[(3S,4R)-3-ethoxy-1-(5-formyl-1,3,4-thiadiazol-2-yl)piperidin-4-yl]-5-ethyl-1H-imidazole-2-carboxamide (0.68 g) obtained above in THF (30 mL), and the mixture was stirred for 1 hour. A saturated aqueous ammonium chloride solution was added thereto, followed by extraction with ethyl acetate, and the organic layer was washed with brine. The residue obtained by the concentration under reduced pressure was purified by silica gel column (ethyl acetate/methanol) to obtain the title compound (0.40 g, 75%) as a colorless amorphous solid.

$^1$H-NMR (400 MHz, CDCl$_3$) δ ppm: 11.65 (1H, s), 7.55 (1H, d, J=9.16 Hz), 5.13 (1H, q, J=6.11 Hz), 4.34-4.31 (1H, m), 4.25-4.22 (1H, m), 3.91-3.89 (1H, m), 3.72 (1H, dq, J=8.88, 7.16 Hz), 3.62 (1H, s), 3.44 (1H, dq, J=8.88, 7.16 Hz), 3.29-3.17 (3H, m), 2.71 (2H, q, J=7.64 Hz), 2.16-2.11 (1H, m), 1.79-1.76 (1H, m), 1.62 (3H, d, J=6.11 Hz), 1.26 (3H, td, J=7.64, 2.28 Hz), 1.16 (3H, td, J=7.16, 1.72 Hz).

Example 2

Synthesis of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (Exemplified Compound No. 2)

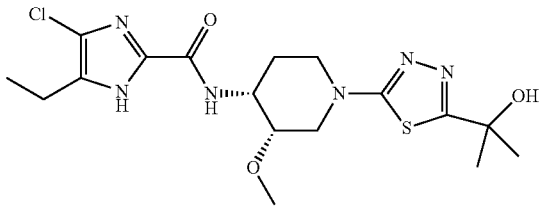

Step 1: Synthesis of tert-butyl cis(±)-4-{[(benzyloxy)carbonyl]amino}-3-methoxypiperidine-1-carboxylate Diisopropylethylamine (26.4g, 204mmol) was added to a solution of tert-butyl cis(±)-4-amino-3-methoxypiperidine-1-carboxylate (39.2 g, 170 mmol) in dichloromethane (400 mL), a solution of benzyl chloroformate (43.5 g, 255 mmol) in dichloromethane (80 mL) was added dropwise under ice-cooling, and the mixture was further stirred for 1 hour. The reaction solution was washed with water and 10% aqueous sodium chloride solution and concentrated under reduced pressure. The residue was purified by silica gel chromatography (elution solvent: hexane/ethyl acetate=100/0, 100/15, 100/30), and the resultant was further solidified using a ethyl acetate/hexane mixed solvent to obtain title compound (40.0 g, 65%) as a white solid.

$^1$H-NMR (400 MHz, CDCl$_3$) δ ppm: 7.29-7.40 (5H, m), 5.10 (2H, s), 5.04-5.16 (1H, m), 4.26-4.50 (1H, m), 3.91-4.22 (1H, m), 3.37 (3H, s), 3.25-3.37 (1H, m), 2.60-2.90 (2H, m), 1.63-1.76 (2H, m), 1.46 (9H, s).

Mass spectrum (ESI): m/z 365 (M+H)$^+$.

Step 2: tert-butyl (3S,4R)-4-{[(benzyloxy)carbonyl]amino}-3-methoxypiperidine-1-carboxylate The tert-butyl cis(±)-4-{[(benzyloxy)carbonyl]amino}-3-methoxypiperidine-1-carboxylate (100 g, 274 mmol) obtained in Step 1 was optically resolved using an optically active column (CHIRALCEL OJ-H®, elution solvent: hexane/2-propanol=90/10 (v/v)). The first-eluting peak compound (49.5 g) and the second-eluting peak compound (48.9 g) were obtained as colorless oily substances.

$^1$H-NMR (400 MHz, CDCl$_3$) δ ppm: 7.29-7.40 (5H, m), 5.10 (2H, s) 5.04-5.16 (1H, m), 4.26-4.50 (1H, m), 3.91-4.22 (1H, m), 3.37 (3H, s), 3.25-3.37 (1H, m), 2.60-2.90 (2H, m), 1.63-1.76 (2H, m), 1.46 (9H, s).

Mass (ESI): m/z 365 (M+H)$^+$.

Step 3: Synthesis of tert-butyl (3S,4R)-4-amino-3-methoxypiperidine-1-carboxylate 10% palladium-carbon (108 g) was added to a solution of the second-eluting peak compound obtained in Step 2 (230 mg, 0.631 mmol) in methanol (7 mL), and the mixture was stirred under a hydrogen gas atmosphere at room temperature for 1 hour and 30 minutes. The reaction solution, from which the catalyst was removed by filtration, was concentrated under reduced pressure to obtain title compound (141 mg, 97%) as a colorless oily substance.

Step 4: Synthesis of tert-butyl (3S,4R)-4-{[(4-chloro-5-ethyl-1H-imidazol-2-yl)carbonyl]amino}-3-methoxypiperidine-1-carboxylate The same operation as in Example 1 (Step 2) was performed using the tert-butyl (3S,4R)-4-amino-3-methoxypiperidine-1-carboxylate (224.4 mg, 0.96 mmol) obtained in Step 3 above, 4-chloro-5-ethyl-1H-imidazole-2-carboxylate (140 mg, 0.80 mmol) synthesized by the method described in the literature (WO 2009/084614), EDCl (440 mg, 2.29 mmol) and HOBT (110 mg, 0.81 mmol) to obtain title compound (222.4 mg, 72%) as a white solid.
$^1$H-NMR (400 MHz, CDCl$_3$) δ ppm: 10.90 (1H, br s), 7.45 (1H, br s), 4.19-4.35 (3H, m), 3.41 (3H, s), 3.32-3.39 (2H, m), 2.72-2.89 (1H, m), 2.68 (2H, q, J=7.57 Hz), 1.79-1.91 (1H, m), 1.61-1.69 (1H, m), 1.47 (9H, s), 1.26 (3H, t, J=7.57 Hz).

Step 5: Synthesis of ethyl 5-[(3S,4R)-4-{[(4-chloro-5-ethyl-1H-imidazol-2-yl)carbonyl]amino}-3-methoxypiperidin-1-yl]-1,3,4-thiadiazole-2-carboxylate A hydrogen chloride/ethyl acetate solution (4N, 3 mL) was added to a solution of tert-butyl (3S,4R)-4-{[(4-chloro-5-ethyl-1H-imidazol-2-yl)carbonyl]amino}-3-methoxypiperidine-1-carboxylate (1.0 g) obtained in Step 4 in ethyl acetate (3 mL), and the mixture was allowed to stand at room temperature for 30 minutes. The solvent was evaporated under reduced pressure to obtain crude 4-chloro-N-[(3S,4R)-3-methoxypiperidin-4-yl]-5-ethyl-1H-imidazole-2-carboxamide hydrochloride as a colorless amorphous solid.
A suspension of the crude 4-chloro-N-[(3S,4R)-3-methoxypiperidin-4-yl]-5-ethyl-1H-imidazole-2-carboxamide hydrochloride obtained above, ethyl 5-bromo-1,3,4-thiadiazole-2-carboxylate (0.66 g) and sodium bicarbonate (1.05 g) in DMF (40 mL) was stirred at 70° C. for 3 hours. The reaction solution was diluted with ethyl acetate, washed with water and brine, and dried over anhydrous magnesium sulfate. The solvent was evaporated under reduced pressure, and the resulting residue was purified by silica gel column (ethyl acetate-hexane) to obtain title compound (1.4 g) as a colorless solid.
Mass (ESI): m/z 443 (M+H)$^+$.

Step 6: Synthesis of 4-chloro-5-ethyl-N-{(3S,4R)-1-[5-(1-hydroxy-1-methylethyl)-1,3,4-thiadiazol-2-yl]-3-methoxypiperidin-4-yl}-1H-imidazole-2-carboxamide Methylmagnesium bromide (1.12 mol/l THF solution, 10 mL, 11 mmol) was added under ice-cooling to a solution of ethyl 5-[(3S,4R)-4-{[(4-chloro-5-ethyl-1H-imidazol-2-yl)carbonyl]amino}-3-methoxypiperidin-1-yl]-1,3,4-thiadiazole-2-carboxylate obtained in Step 5 (0.35 g, 0.79 mmol) in THF (15 mL), and the mixture was stirred for 40 minutes. A saturated ammonium chloride solution was added thereto, followed by extraction with ethyl acetate, and the organic layer was washed with brine. The residue obtained by the concentration under reduced pressure was purified by silica gel column (ethyl acetate/methanol) to obtain the title compound (0.40 g, 88%) as a colorless amorphous solid.

$^1$H-NMR (400 MHz, CDCl$_3$) δ: 11.29 (1H, s), 7.53 (1H, d, J=9.16 Hz), 4.48-4.45 (1H, m), 4.27-4.22 (1H, m), 3.85-3.82 (1H, m), 3.52 (1H, s), 3.42 (3H, s), 3.31-3.24 (1H, m), 3.15-3.12 (1H, m), 2.92 (1H, s), 2.70 (2H, q, J=7.64 Hz), 2.12-2.07 (1H, m), 1.81-1.79 (1H, m), 1.68 (6H, d, J=2.29 Hz), 1.26 (3H, t, J=7.64 Hz).

Example 3

Synthesis of 4-chloro-5-ethyl-N-{(3S,4R)-1-[5-(1-hydroxyethyl)-1,3,4-thiadiazol-2-yl]-3-methoxypiperidin-4-yl}-1H-imidazole-2-carboxamide (Exemplified Compound No. 3)

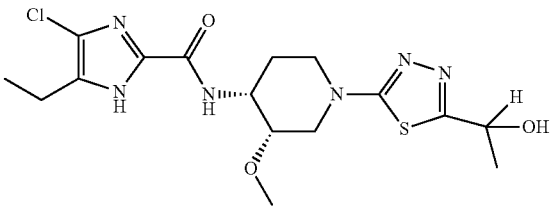

Step 1: Synthesis of 4-chloro-5-ethyl-N-{(3S,4R)-1-[5-(hydroxymethyl)-1,3,4-thiadiazol-2-yl]-3-methoxypiperidin-4-yl}-1H-imidazole-2-carboxamide Sodium borohydride (1.9 g) was added in five divided portions to a solution of ethyl 5-[(3S,4R)-4-{[(4-chloro-5-ethyl-1H-imidazol-2-yl)carbonyl]amino}3-methoxypiperidin-1-yl]-1,3,4-thiadiazole-2-carboxylate obtained in Example 2, Step 5 (1.4 g) in methanol (50 mL) under ice-cooling, and the mixture was stirred. The reaction solution was concentrated under reduced pressure and water was added to a residue, extracted with ethyl acetate, and dried over anhydrous sodium sulfate. Following concentration under reduced pressure, the residue was purified by silica gel column to obtain the title compound (1.0 g) as an amorphous solid.
$^1$H-NMR (400 MHz, CDCl$_3$) δ ppm: 11.14 (1H, s), 7.53 (1H, d, J=9.03 Hz), 4.88 (2H, s), 4.44-4.48 (1H, m), 4.23-4.27 (1H, m), 3.85-3.87 (1H, m), 3.51 (1H, s), 3.41 (3H, s), 3.28-3.31 (1H, m), 3.14-3.18 (1H, m), 2.80 (1H, br s), 2.70 (2H, q, J=7.57 Hz), 2.05-2.12 (1H, m), 1.78-1.81 (1H, m), 1.26 (3H, t, J=7.69 Hz).
Mass (ESI) : m/z 401 (M+H)$^+$.

Step 2: Synthesis of 4-chloro-5-ethyl-N-{(3S,4R)-1-[5-(1-hydroxyethyl)-1,3,4-thiadiazol-2-yl]-3-methoxypiperidin-4-yl}-1H-imidazole-2-carboxamide Manganese dioxide (0.42 g) was added to a solution of 4-chloro-5-ethyl-N-{(3S,4R)-1-[5-(hydroxymethyl)-1,3,4-thiadiazol-2-yl]-3-methoxypiperidin-4-yl}-1H-imidazole-2-carboxamide (0.1 g) obtained in Step 1 in THF (5 mL), and the mixture was stirred at room temperature overnight. After filtering through celite®, the reaction solution was concentrated under reduced pressure to obtain crude 4-chloro-5-ethyl-N-[(3S,4R)-1-(5-formyl-1,3,4-thiadiazol-2-yl)-3-methoxypiperidin-4-yl]-1H-imidazole-2-carboxamide as an amorphous solid.

Methylmagnesium bromide (1.1 mol/L THF solution, 6 mL) was added under ice-cooling to a solution of crude 4-chloro-5-ethyl-N-[(3S,4R)-1-(5-formyl-1,3,4-thiadiazol-2-yl)-3-methoxypiperidin-4-yl]-1H-imidazole-2-carboxamide in THF (5 mL), and the mixture was stirred. Water and 1 mol/L hydrochloric acid were added, followed by extraction with ethyl acetate, and the organic layer was washed with brine. The residue obtained by the concentration under reduced pressure was purified by silica gel column (ethyl acetate/methanol) to obtain the title compound (0.057 g) as an amorphous solid.

$^1$H-NMR (400 MHz, CDCl$_3$) δ ppm: 11.12 (1H, br s), 7.47-7.57 (1H, m), 5.07-5.18 (1H, m), 4.41-4.51 (1H, m), 4.19-4.31 (1H, m), 3.79-3.91 (1H, m), 3.51 (1H, br s), 3.41 (3H, s), 3.23-3.34 (1H, m), 3.15 (1H, br d, J=14.65 Hz), 2.91 (1H, br s), 2.70 (2H, q, J=7.52 Hz), 2.02-2.15 (1H, m), 1.75-1.84 (1H, m), 1.60-1.64 (3H, m), 1.26 (3H, t, J=7.52 Hz).

Mass (ESI) : m/z 415 (M+H)$^+$.

Example 4

Synthesis of 4-chloro-5-ethyl-N-[(3S,4R)-1-{5-[(1R)-1-hydroxyethyl]-1,3,4-thiadiazol-2-yl}-3-methoxypiperidin-4-yl]-1H-imidazole-2-carboxamide, and (Exemplified Compound No. 4)

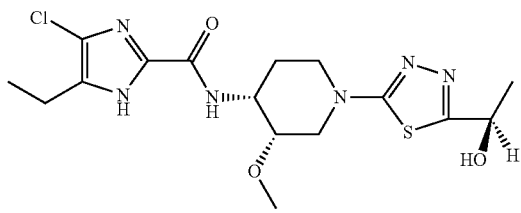

4-Chloro-5-ethyl-N-[(3S,4R)-1-{5-[(1S)-1-hydroxyethyl]-1,3,4-thiadiazol-2-yl}-3-methoxypiperidin-4-yl]-1H-imidazole-2-carboxamide (Exemplified Compound No. 5)

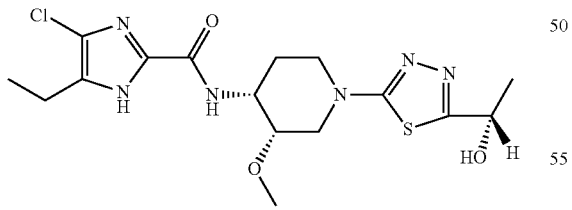

The 4-chloro-5-ethyl-N-{(3S,4R)-1-[5-(1-hydroxyethyl)-1,3,4-thiadiazol-2-yl]-3-methoxypiperidin-4-yl}-1H-imidazole-2-carboxamide obtained in Example 3 (Step 2) (an about 1:1 mixture of diastereomers, 53.2 g) was diastereomerically resolved using an optical activity column (CHIRALPAC IC®, elution solvent: hexane/2-propanol=80/20 (v/v)). The first-eluting peak compound (23.1 g) and the second-eluting peak compound (23.0 g) were obtained as light color non-crystalline solids, respectively.

First-eluting peak compound was Compound No. 4 and Second-eluting peak compound was Compound No. 5.

In Compound No. 4, the configuration of the hydroxy group was determined as R configuration because the present compound was acetylated under stereoselective acetylation reaction conditions using Lipase PS Amano SD/isopropenyl acetate.

$^1$H-NMR (400 MHz, CDCl$_3$) δ ppm: 11.21 (1H, br s), 7.53 (1H, d-like, J=9 Hz), 5.13 (1H, q, J=6.5 Hz), 4.48 (1H, br d, J=13 Hz), 4.26 (1H, m), 3.88 (1H, br d, J=13 Hz), 3.52 (1H, br s), 3.42 (3H, s), 3.32 (1H, td, J=13, 3 Hz), 3.19 (1H, br d, J=ca. 13 Hz), 2.70 (2H, q, J=7.6 Hz), 2.09 (1H, qd, J=13, 4 Hz), 1.80 (1H, dq-like, J=13, ca. 4 Hz), 1.62 (3H, d, J=6.59 Hz), 1.24 (3H, t, J=7.6 Hz).

IR (KBr)cm$^{-1}$ : 2973, 1650, 1532, 1437, 1261, 1116, 1069.

Mass (ESI) : m/z 415 (M+H)$^+$.

High resolution mass spectrum (ESI) : m/z C$_{16}$H$_{24}$ClN$_6$O$_3$S ((M+H)$^+$), calculated; 415.13191, observed; 415.13209.

In Compound No. 5, the configuration of the hydroxy group was determined as S configuration because the present compound was hardly acetylated under stereoselective acetylation reaction conditions using Lipase PS Amano SD/isopropenyl acetate.

$^1$H-NMR (400 MHz, CDCl$_3$) δ ppm: 11.25 (1H, br s), 7.55 (1H, d-like, J=9 Hz), 5.13 (1H, q, J=6.5 Hz), 4.50 (1H, br d, J=13 Hz), 4.26 (1H, m), 3.86 (1H, br d, J=13 Hz), 3.52 (1H, br s), 3.42 (3H, s), 3.32 (1H, td, J=13, 3 Hz), 3.19 (1H, br d, J=ca. 13 Hz), 2.70 (2H, q, J=7.6 Hz), 2.09 (1H, qd, J=13, 4 Hz), 1.81 (1H, dq-like, J=13, ca. 4 Hz), 1.62 (3H, d, J=6.59 Hz), 1.26 (3H, d, J=7.69 Hz). IR (KBr)cm$^{-1}$ : 2973, 1650, 1532, 1437, 1262, 1116, 1069.

Mass (ESI) : m/z 415 (M+H)$^+$.

High resolution mass spectrum (ESI) : m/z C$_{16}$H$_{24}$ClN$_6$O$_3$S ((M+H)$^+$), calculated; 415.13191, observed; 415.13129.

Example 5

Synthesis of 4-chloro-5-ethyl-N-{(3S,4R)-1-[5-(1-hydroxypropan-2-yl)-1,3,4-thiadiazol-2-yl]-3-methoxypiperidin-4-yl}-1H-imidazole-2-carboxamide (Exemplified Compound No. 6)

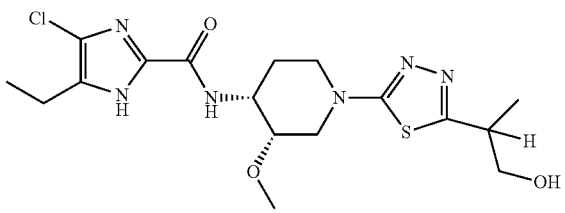

Step 1: Synthesis of 4-chloro-5-ethyl-N-{(3S,4R)-3-methoxy-1-[5-(prop-1-en-2-yl)-1,3,4-thiadiazol-2-yl]piperidin-4-yl}-1H-imidazole-2-carboxamide

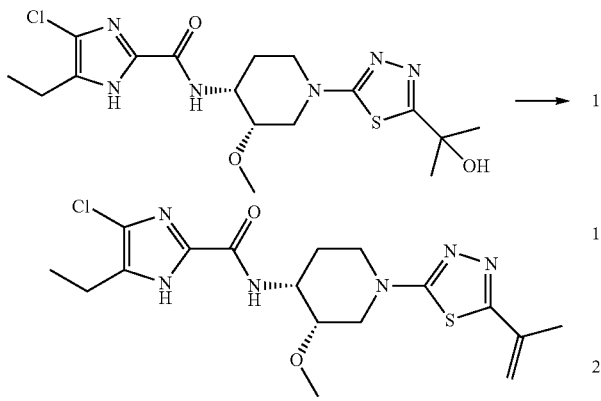

4-Chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (1.0 g, 2.3 mmol) was dissolved in dry toluene (50 mL) at room temperature followed by addition of p-toluenesulfonic acid (39 mg, 0.23 mmol, 0.1 equiv.). The reaction mixture was stirred at 80° C. overnight. After completion of reaction, the reaction mixture was diluted with ethyl acetate and washed with water. The organic layer was separated and concentrated under vacuo. The crude reaction mixture was subjected to column chromatography (methanol-dichloromethane, 5%) to obtain the title compound (575 mg) as pale brown solid.
Mass (ESI) : m/z 411.11 (M+H)$^+$.

Step 2: Synthesis of 4-chloro-5-ethyl-N-{(3S,4R)-1-[5-(1-hydroxypropan-2-yl)-1,3,4-thiadiazol-2-yl]-3-methoxypiperidin-4-yl}-1H-imidazole-2-carboxamide 4-Chloro-5-ethyl-N-{(3S,4R)-3-methoxy-1-[5-(prop-1-en-2-yl)-1,3,4-thiadiazol-2-yl]piperidin-4-yl}-1H-imidazole-2-carboxamide obtained in Step 1 (200 mg, 0.486 mmol) was dissolved in dry THF (10 mL) at room temperature. The solution was cooled to 0° C. followed by addition of borane tetrahydrofuran complex solution (1.944 mmol, 2.0 mL, 1 M). The resulting reaction mixture was stirred at room temperature for 18 hours. Subsequently, sodium hydroxide solution (0.5N, 1.5 mL), water (0.5 mL) and hydrogen peroxide (30% w/v, 0.5 mL) were added to the reaction mixture, stirred at room temperature for 5 hours. After completion of reaction, the reaction mixture was diluted with ethyl acetate (50 mL) and washed with water (20 mL×2). The organic layer was separated and concentrated under vacuo. The crude reaction mixture was subjected to column chromatography (methanol-dichloromethane, 3%) to obtain the title compound (100 mg) as white solid.
$^1$H-NMR (400 MHz, MeOD) δ ppm: 4.28-4.20 (m, 2H), 3.91-3.88 (m, 1H), 3.70 (d, 2H, J=5.96 Hz), 3.58 (brs, 1H), 3.43 (s, 3H), 3.34-3.30 (m, 1H), 3.27-3.20 (m, 2H), 2.31 (q, 2H, J=15.1 Hz, 7.6 Hz), 2.07-1.90 (m, 1H), 1.82-1.76 (m, 1H), 1.33 (dd, 3H, J=7.0 Hz,1.4 Hz), 1.19 (t, 3H, J=15.1 Hz).
Mass (ESI) : m/z 428.89 (M+H)$^+$.

Example 6

Synthesis of 4-chloro-N-{(3S,4R)-3-ethoxy-1-[5-(2-hydroxypropan-2-yl)-1,3,4-thiadiazol-2-yl]piperidin-4-yl}-5-ethyl-1H-imidazole-2-carboxamide (Exemplified Compound No. 7)

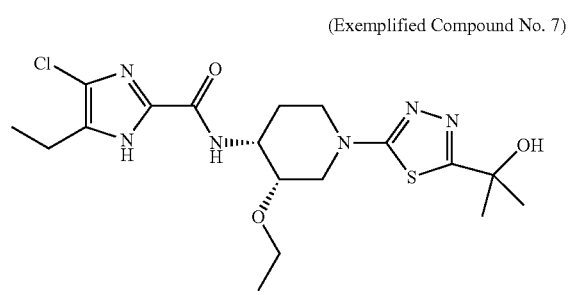 [SMILES: CCO[C@H]1CN(c2nnc(C(C)(C)O)s2)CC[C@H]1NC(=O)c1nc(Cl)c(CC)[nH]1]

The title compound was prepared by an analogous method described in Example 2 using tert-butyl cis(±)-4-amino-3-ethoxypiperidine-1-carboxylate in Step 1 instead of tert-butyl cis(±)-4-amino-3-methoxypiperidine-1-carboxylate.
$^1$H-NMR (400 MHz, MeOD) δ ppm: 4.24-4.17 (m, 2H), 3.96-3.93 (m, 1H), 3.77-3.63 (m, 3H), 3.53-3.47 (m, 1H), 3.36 (d, 1H, J=1.64 Hz), 2.62 (q, 2H, J=15.1 Hz, 7.6 Hz), 2.12-2.02 (m, 1H), 1.85-1.75 (m, 1H), 1.59 (d, 6H, J=3.4 Hz), 1.20 (t, 3H, J=7.6 Hz), 1.13 (t, 3H, J=6.9 Hz).
Mass (ESI) : m/z 442.96 (M+H)$^+$.

Example 7

Synthesis of 4-chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide
and (Exemplified Compound No. 8)

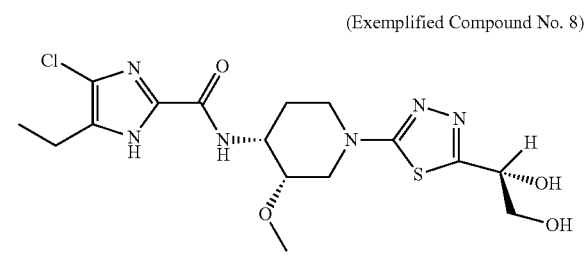 [SMILES: CCc1[nH]c(C(=O)N[C@@H]2CCN(c3nnc([C@H](O)CO)s3)C[C@@H]2OC)nc1Cl]

4-chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide (Exemplified Compound No. 9)

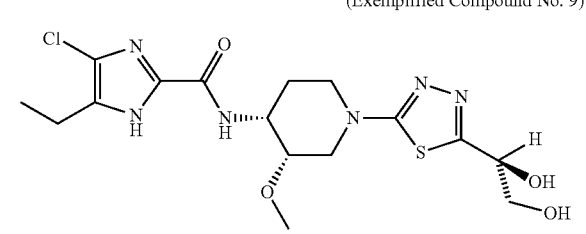

Step 1: Synthesis of N-[(3S,4R)-1-(5-bromo-1,3,4-thiadiazol-2-yl)-3-methoxypiperidin-4-yl]-4-chloro-5-ethyl-1H-imidazole-2-carboxamide The hydrochloride salt of title compound (1.9 g) as white solid was prepared in a similar manner as described in Example 2, Step 5 by using tert-butyl (3S,4R)-4-{[(4-chloro-5-ethyl-1H-imidazol-2-yl)carbonyl]amino}-3-methoxypiperidine-1-carboxylate (2g, 5.17 mmol), ethyl acetate (20 mL), hydrochloric acid solution (20 ml, 4N in dioxane).

To a solution of this compound (0.1 g, 0.31 mmole) in acetonitrile (5 mL), diisopropylethylamine (0.15 mL, 0.93 mmol) and 2,5-dibromo-1,3,4-thiadiazole (0.11 g, 0.46 mmol) were added. The reaction mixture was allowed to stir at 80° C. for 4 hours. The reaction mixture was diluted with ethyl acetate (50 mL) and water (5 mL) and stirred for 10 minutes. The organic layer was separated, washed with brine solution and concentrated. The crude product was purified using column chromatography (ethyl acetate in hexane, 30%) to obtain the title compound (84 mg) as off-white gum.
Mass (ESI) : m/z 451.07 (M+H)⁺.

Step 2: Synthesis of 4-chloro-N-[(3S,4R)-1-(5-ethenyl-1,3,4-thiadiazol-2-yl)-3-methoxypiperidin-4-yl]-5-ethyl-1H-imidazole-2-carboxamide

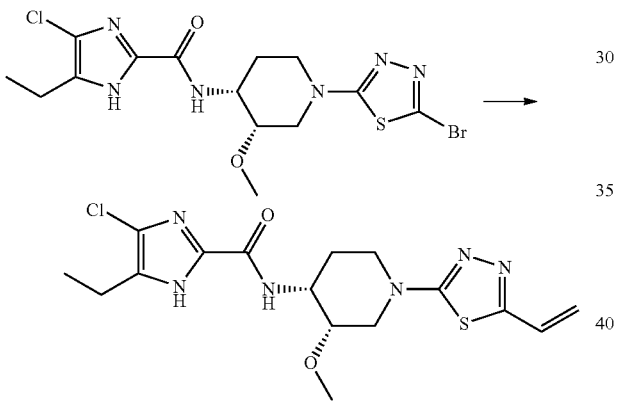

To a solution of N-[(3S,4R)-1-(5-bromo-1,3,4-thiadiazol-2-yl)-3-methoxypiperidin-4-yl]-4-chloro-5-ethyl-1H-imidazole-2-carboxamide (0.08 g, 0.18 mmol) in DMF (5 mL), vinyltributyltin (0.17 mL, 0.53 mmol) and bis-triphenylphosphinepalladium dichloride (0.025 g, 0.03 mmol) were added. The reaction mixture was allowed to stir at 90° C. for 4 hours. The reaction mixture was diluted with ethyl acetate (50 mL) and water (5 mL) and stirred for 10 minutes. The organic layer was separated, washed with brine, and concentrated. The crude product was purified using column chromatography (ethyl acetate in hexane, 40%) to obtain the title compound (26 mg) as off-white gum.
Mass (ESI) : m/z 397.14 (M+H)⁺.

Step 3: Synthesis of 4-chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide, and 4-chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide To a solution of AD-mix-β® (741 mg, 1.4 g/mmol) in t-butanol and water (3 mL each), methanesulfonamide (0.05 g, 0.53 mmol) was added and the reaction mixture was allowed to stir at 0° C. for 20 minutes. 4-Chloro-N-[(3S,4R)-1-(5-ethenyl-1,3,4-thiadiazol-2-yl)-3-methoxypiperidin-4-yl]-5-ethyl-1H-imidazole-2-carboxamide (0.21g, 0.53 mmol; Obtained in Step 2) was added to the reaction mixture and the mixture was stirred at room temperature for 18 hours. The reaction mixture was quenched by sodium sulfite solution and the reaction mixture was diluted with ethyl acetate (100 mL) and water (5 mL). The organic layer was separated, washed with brine, and concentrated. The crude product was purified using column chromatography (methanol in dichloromethane, 10%) to obtain 4-chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide (105 mg) as white solid.
¹H-NMR (400 MHz, MeOD) δ ppm: 4.30-4.20 (m, 2H), 3.93-3.81 (m, 2H), 3.75-3.71 (m, 1H), 3.60-3.55 (bs, 1H), 3.44 (s, 3H), 3.40-3.30 (m, 3H), 2.64 (q, 2H, J=14.8 and 7.6 Hz), 2.04-1.98 (m, 1H), 1.83-1.78 (m, 1H), 1.23 (t, 3H, J=7.6 Hz).
Mass: m/z 430.84 (M+H)⁺.

Similarly, 4-chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide (32 mg) was prepared using AD-mix-α® (247 mg, 1.4 g/mmol), methanesulfonamide (0.02 g, 0.17 mmol) and 4-chloro-N-[(3S,4R)-1-(5-ethenyl-1,3,4-thiadiazol-2-yl)-3-methoxypiperidin-4-yl]-5-ethyl-1H-imidazole-2-carboxamide (0.07 g, 0.17 mmol).
¹H-NMR (400 MHz, MeOD) δ ppm: 4.30-4.20 (m, 2H), 3.94-3.81 (m, 2H), 3.76-3.71 (m, 1H), 3.60-3.56 (bs, 1H), 3.44 (s, 3H), 3.40-3.30 (m, 3H), 2.64 (q, 2H, J=15.2 and 7.6 Hz), 2.04-1.98 (m, 1H), 1.81-1.79 (m, 1H), 1.21 (t, 3H, J=7.6 Hz).
Mass: m/z 430.88 (M+H)⁺.

Example 8

Synthesis of 4-chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide (Exemplified Compound No. 10)

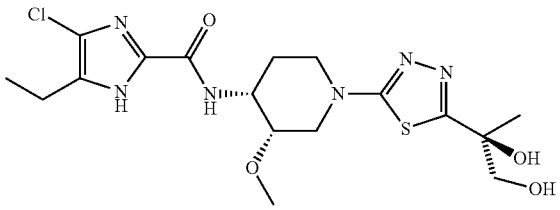

To a solution of AD-mix-α® (20.4 g, 1.4 g/mmol) in t-butanol and water (300 mL each), methanesulfonamide (1.38 g, 14.6 mmol) was added, and the reaction mixture was allowed to stir at 0° C. for 20 minutes. 4-Chloro-5-ethyl-N-{(3S,4R)-3-methoxy-1-[5-(prop-1-en-2-yl)-1,3,4-thiadiazol-2-yl]piperidin-4-yl}-1H-imidazole-2-carboxamide obtained in Example 5, Step 1 (6.0 g, 14.6 mmol) was added to the reaction mixture and the mixture was stirred at room temperature for 18 hours. The reaction mixture was quenched by sodium sulfite solution and the reaction mixture was diluted with ethyl acetate (500 mL) and water (50 mL). The organic layer was separated, washed with brine and concentrated. The crude product was purified using column chromatography (10% methanol in dichloromethane) to obtain 4-chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide (3.6 g) as off-white amorphous solid.

$^1$H-NMR (400 MHz, CDCl$_3$) δ ppm: 11.89 (s,1H), 7.64 (d,1H, J=8.96 Hz), 4.37 (d, 1H, J=13.84 Hz), 4.30-4.20 (m, 1H), 4.13 (d, 1H, J=11.4 Hz), 3.80 (d, 1H, J=13.28 Hz), 3.69 (d, 1H, J=11.36 Hz), 3.50 (s, 1H), 3.37 (s, 3H), 3.22 (dt, 1H, J=13.2, 3.0 Hz), 3.11 (d, 1H, J=13.24 Hz), 2.66 (q, 2H, J=15.16, 7.56 Hz), 2.15-2.05 (m, 1 H), 1.80-1.70 (m, 2H), 1.54 (s, 3H), 1.23 (t, 3H, J=7.56 Hz).

Mass: m/z 445.10 (M+H)$^+$.

Example 9

Synthesis of 4-chloro-N-[(3S,4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamide (Exemplified Compound No. 11)

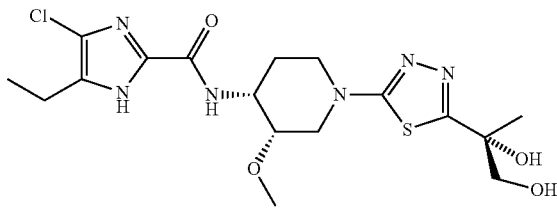

To a solution of AD-mix-β® (17.08 g, 1.4 g/mmol) in t-butanol and water (75 mL each), methanesulfonamide (1.16 g, 12.2 mmol) was added, and the reaction mixture was allowed to stir at 0° C. for 20 minutes. 4-Chloro-5-ethyl-N-{(3S,4R)-3-methoxy-1-[5-(prop-1-en-2-yl)-1,3,4-thiadiazol-2-yl]piperidin-4-yl}-1H-imidazole-2-carboxamide obtained in Example 5, Step 1 (5.0 g, 12.2 mmol) was added to the reaction mixture and the mixture was stirred at room temperature for 18 hours. The reaction mixture was quenched by sodium sulfite solution and the reaction mixture was diluted with ethyl acetate (400 mL) and water (30 mL). The organic layer was separated, washed with brine, and concentrated. The crude product was purified using column chromatography (10% methanol in dichloromethane) to obtain the title compound (3.1 g) as amorphous solid.

$^1$H-NMR (400 MHz, CDCl$_3$) δ ppm: 11.79 (bs,1H), 7.62 (d,1H, J=8.96 Hz), 4.40-4.35 (m, 1H), 4.30-4.20 (m, 2H), 4.13 (s, 1H), 3.85-3.80 (m, 1H), 3.70-3.60 (m, 2H), 3.37 (s, 3H), 3.23 (dt, 1H, J=12.9, 2.9 Hz), 3.11 (d, 1H, J=12.92 Hz), 2.66 (q, 2H, J=15.2, 7.56 Hz), 2.15-2.05 (m, 1H), 1.80-1.75 (m, 2H), 1.54 (s, 3H), 1.23 (t, 3H, J=7.56 Hz).

Mass: m/z 445.11 (M+H)$^+$.

Example 10

Synthesis of crystalline 2/3 hydrate form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (Form I)

Water (100 μL) was added to 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (about 20 mg), and the mixture was stirred at 40° C. for about 3 weeks. A solid was collected and dried at room temperature over-night to obtain a crystalline 2/3 hydrate of the title compound designated as Form I.

The Form I thus obtained was characterized by i) the diffraction pattern obtained from powder X-ray diffraction analysis (CuK, λ=1.54 Å, scan rate=20°/min) (FIG. 2) and ii) the thermogravimetric analysis pattern (TG/DTA pattern) obtained from measurement of sample (3 mg) at heating rate of about 10° C./minute (FIG. 3). The compound showed mass loss corresponded to 2/3 hydrate (theoretical amount: 2.7%). Further, the pattern of change of weight of the sample was shown (FIG. 4), which was observed when relative humidity was varied stepwise. The change of weight of this compound stayed within 0.3%, the change of weight was small and did not show weight change due to absorption or desorption of moisture.

Example 11

Synthesis of anhydrous crystalline form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (Form II)

4-Chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide was dried under reduced pressure at 40° C. over-night, then toluene (10 mL) was added to the compound (2 g), the mixture was stirred magnetically for about 3 days with occasional stirring with spatula. The solid thus obtained was dried under air to obtain anhydrous crystalline form of the title compound designated as Form II.

The diffraction pattern obtained from powder X-ray diffraction analysis (CuK, λ=1.54 Å, scan rate=20°/min) for this anhydrate is shown in FIG. 5.

The thermogravimetric analysis pattern (TG/DTA pattern) obtained from measurement of sample (3 mg) at heating rate of about 10° C./minute is as depicted in FIG. 6. The mass loss corresponds to the level of decrease of absorbed water, and this strongly suggested that the compound was anhydrate. Further, the pattern of change of weight of the sample was shown in FIG. 7, which was observed when relative humidity was varied stepwise. This compound substantilally showed no weight change due absorption or desorption of moisture.

Example 12

Synthesis of anhydrous crystalline form of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (Form Ill)

Toluene (100 μL) was added to 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (about 20 mg), and the mixture was stirred at 40° C. for about 3 weeks. A solid was collected and dried at room temperature over-night to obtain anhydrous crystalline form of the title compound designated as Form Ill.

Example 13

Synthesis of crystalline form of 4-chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide (Form A)

Charged 4-chloro-N-[(3S,4R)-1-{5-[(2R)-1,2-dihydroxypropan-2-yl]-1,3,4-thiadiazol-2-yl}-3-methoxypiperidin-4- yl]-5-ethyl-1H-imidazole-2-carboxamide (225 g) with acetonitrile (4.5 L) and the mixture was heated to reflux for 1 hour. The mixture was allowed to cool to room temperature and stirred at same temperature for overnight. The insolubles were filtered and the clear solution thus obtained was allowed to stir at room temperature for 2 days. The solid was obtained, which was filtered, washed with acetonitrile (750 mL) and dried in air oven at 60° C. for overnight to obtain crystalline form of the title compound (125 g), designated as Form A.

The powder X-ray diffraction pattern of crystalline form of the title compound is shown in FIG. 8.

Example 14

Synthesis of crystalline form of 4-chloro-N-[(3S, 4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamide (Form B)

4-Chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide (10 mg) was placed in a small vial. This vial was placed in a bigger vial containing ethyl acetate (4 mL), which was capped and sealed using Teflon. This system was kept at 40° C. for 4 days to obtain crystals of the title compound, designated as Form B. (Solvent-Vapor Method).

The powder X-ray diffraction pattern of crystalline form of title compound is shown in FIG. 9.

Example 15

Synthesis of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide (Exemplified Compound No. 2)

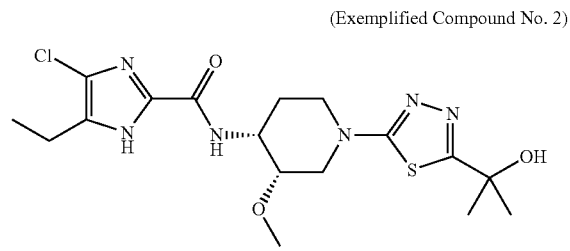 [SMILES: CCc1[nH]c(C(=O)N[C@@H]2CCN(c3nnc(C(C)(C)O)s3)C[C@@H]2OC)nc1Cl]

Step 1: Synthesis of 2-(5-amino-1,3,4-thiadiazol-2-yl)propan-2-yl benzoate

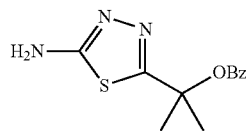

To a 1,4-dioxane (100 mL) solution of hydrazinecarbothioamide (10 g, 109.72 mmol), were added 2-(benzoyloxy)-2-methylpropanoic acid (22.85 g, 109.72 mmol) and phosphorous oxychloride (25.24 g, 164.58 mmol). The mixture was heated to 50 to 55° C. and stirred at that temperature for 8 hours. The reaction mixture was cooled below 5° C., and after ethyl acetate (50 mL) and water (70 mL) were added thereto, pH of the mixture was adjusted to 8 by 8M potassium hydroxide aqueous solution. To the mixture, ethyl acetate (50 mL), tetrahydrofuran (20 mL) and water (10 mL) were added and organic layer was collected. After the organic layer was washed with 10% sodium chloride aqueous solution (30 mL), the organic solution was concentrated under reduced pressure to about 100 mL of volume. To the concentrate, was added ethyl acetate (50 mL), then the mixture was concentrated under reduced pressure to about 100 mL of volume. To the concentrate, was added heptane (50 mL), then the mixture was cooled below 5° C. and stirred at that temperature for 1 hour to yield a slurry mixture. A solid in the slurry was collected by filtration and washed with cold mixture of ethyl acetate/heptane (2/1; 20 mL). The solid was dried at 50° C. for over 10 hours to yield 19.98 g (69.2%) of the titled compound as a colorless solid.

$^1$H-NMR (400 MHz, DMSO-$d_6$) δ ppm: 7.26-7.22 (m, 2H), 7.01-6.95 (m, 1H), 6.88-6.81 (m, 2H), 6.57-6.48 (brs, 2H), 1.90 (s, 6H).

Step 2: Synthesis of 2-(5-bromo-1,3,4-thiadiazol-2-yl)propan-2-yl benzoate

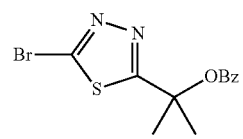

To an acetonitrile (100 mL) solution of 2-(5-amino-1,3,4-thiadiazol-2-yl)propan-2-yl benzoate (10 g, 37.98 mmol), was added water (5 mL) and the mixture was cooled below 5° C., then, 48% hydrobromic acid (25.62 g) was added thereto. To the solution, was added an aqueous solution of sodium nitrite (5.24 g/10 mL) keeping the temperature below 10° C. for over 2 hours, then, the mixture was stirred at that temperature for 30 minutes. After the mixture was adjusted to pH 3.4 by 25% sodium hydroxide aqueous solution, ethyl acetate (50 mL) and 20% sodium sulfite aqueous solution (50 mL) were added thereto, then, the mixture was stirred at room temperature for 30 minutes. Organic layer was collected and washed with 20% sodium chloride aqueous solution (30 mL), the organic layer was concentrated under reduced pressure to about 20 mL of volume. To the concentrate, were added 2-propanol (60 mL) and active charcoal (1 g), and the mixture was stirred for 5 minutes, then, charcoal was removed by filtration. Collected charcoal was washed with 2-propanol (30 mL), then the combined filtrate and washings were concentrated under reduced pressure to about 20 mL of volume. To a concentrate, was added 2-propanol (20 mL), then, the mixture was cooled below 5° C. An authentic seed crystal (0.1 g) prepared separately was added thereto and the mixture was stirred at that temperature for 15 hours to yield a slurry mixture. To the slurry mixture, was added water (30 mL) and the mixture was stirred for 1 hour, then, water (30 mL) was added and the mixture was stirred for further 1 hour. Solid in the slurry was collected by filtration, and washed with cold aqueous 2-propanol (2-propanol/water=1/2, 30 mL).

The solid was dried at 40° C. for over 10 hours to yield 11.09 g (89.2%) of the titled compound as yellowish colorless solid.

¹H-NMR (400 MHz, CDCl₃) δ ppm: 8.03-7.99 (m, 2H), 7.62-7.57 (m, 1H), 7.49-7.44 (m, 2H), 2.08 (s, 6H).

Step 3: Synthesis of 2-{5-[(3S,4R)-4-{[(4-Chloro-5-ethyl-1H-imidazol-2-yl)carbonyl]amino}-3-methoxypipendin-1-yl]-1,3,4-thiadiazol-2-yl}propan-2-yl benzoate

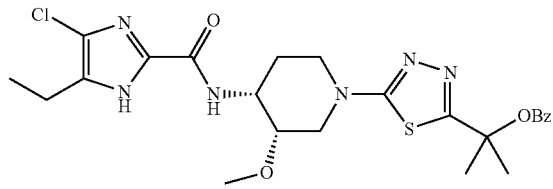

To a dimethylacetamide (90 mL) solution of 4-chloro-5-ethyl-N-[(3S,4R)-3-methoxypiperidin-4-yl]-1H-imidazole-2-carboxamide (18 g, 62.77 mmol) [obtained by treatment of hydrochloride thereof obtained in Step 5, Example 2 with a base], were added 2-(5-bromo-1,3,4-thiadiazol-2-yl)propan-2-yl benzoate (24.6 g, 75.32 mmol) and tripotassium phosphate (17.3 g), and the mixture was heated to 60° C., then the mixture was stirred at that temperature for 26 hours. The reaction mixture was cooled to room temperature, and to the mixture were added toluene (126 mL) and water (90 mL), then the mixture was stirred to yield a three layer mixture. The lowest layer was removed. The lower layer of the rest two layer mixture was separated. To the separated lower layer of aqueous dimethylacetamide layer, was added toluene (126 mL), then the lower layer was removed. The organic layer was combined with upper layer and this was washed with 20% sodium chloride aqueous solution (54 mL), and the organic layer was concentrated under reduced pressure. The concentrated mixture containing the titled compound was used in the next step without further purification.

¹H-NMR (400 MHz, CDCl₃) δ ppm: 12.28 (s, 1H), 8.04-7.99 (m, 2H), 7.59-7.54 (m, 1 H), 7.63-7.59 (m, 1H), 7.47-7.41 (m, 2H), 4.55-4.48 (m, 1H), 4.27-4.20 (m, 1H), 3.86-3.80 (m, 1H), 3.54-3.51 (m, 1H), 3.42 (s, 3H), 3.31-3.23 (m, 1H), 3.16-3.10 (m, 1H), 2.70 (q, 2H, J=6.0 Hz), 2.17-2.06 (m, 1H), 2.03 (s, 3H), 2.03 (s, 3H),1.83-1.77 (m, 1H), 1.26 (t, 3H, J=6.0 Hz).

Step 4: Synthesis of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide To a toluene (72 mL) solution of 2-{5-[(3S,4R)-4-{[(4-chloro-5-ethyl-1H-imidazol-2-yl)carbonyl]amino}-3-methoxypiperidin-1-yl]-1,3,4-thiadiazol-2-yl}propan-2-yl benzoate prepared in the previous step, were added methanol (72 mL) and 28% methanol solution of sodium methoxide (36 mL), and the mixture was stirred at room temperature for 30 minutes. To the mixture, were added toluene (90 mL), methanol (54 mL) and water (90 mL), and the mixture was stirred, then toluene layer was removed. To the aqueous methanol solution, was added toluene (90 mL), and the mixture was adjusted to pH 7.6 by hydrochloric acid and the mixture was stirred. The toluene layer was separated to yield toluene layer-1, and the aqueous methanol layer was separated to yield aqueous methanol layer-1. To the aqueous methanol layer-1, was added toluene (90 mL), and the mixture was stirred. The toluene layer was separated to yield toluene layer-2, and the aqueous methanol layer was separated to yield aqueous methanol layer-2. To a combined toluene layer-1 and -2, were added methanol (90 mL) and water (54 mL), and the mixture was stirred. The aqueous methanol layer was separated and combined with aqueous methanol layer-2. The combined aqueous methanol layer was concentrated under reduced pressure to about 180 mL of volume. To the concentrate, was added ethyl acetate (180 mL), then hydrochloric acid was added to adjust pH to 5.9. The mixture was stirred and the organic layer was separated. This organic layer was washed with 20% sodium chloride aqueous solution (54 mL), then the organic layer was concentrated under reduced pressure to about 54 mL of volume. To the concentrate, was added ethyl acetate (180 mL), then the mixture was concentrated under reduced pressure to about 54 mL of volume. To the concentrate, were added ethyl acetate (90 mL) and heptane (90 mL). The mixture was heated to 45° C. and stirred at that temperature for 30 minutes. After heptane (54 mL) was added thereto, the mixture was stirred for 30 minutes to yield a slurry mixture. The slurry mixture was cooled below 5° C. and stirred for further 1 hour. The solid in the slurry was collected by filtration and the collected solid was washed with cold mixture of ethyl acetate/heptane (1/1, 90 mL). The solid was dried at 50° C. for over 10 hours to yield 21.42 g (79.6%) of the titled compound as a white solid.

Alternatively, 2-{5-[(3S,4R)-4-{[(4-Chloro-5-ethyl-1H-imidazol-2-yl)carbonyl]amino}-3-methoxypipendin-1-yl]-1,3,4-thiadiazol-2-yl}propan-2-yl benzoate

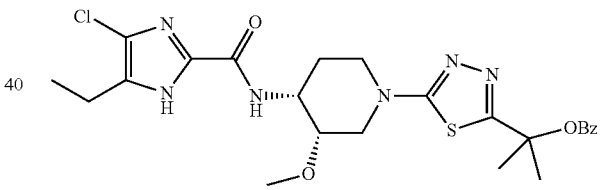

was also prepared as follows:

Step 1: Synthesis of tert-butyl (3S,4R)-3-methoxy-4-{[(1R)-1-phenylethyl]amino}piperidine-1-carboxylate monobutanedioate

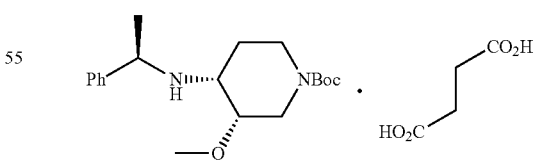

To a dimethylacetamide (1000 mL) solution of tert-butyl 3-methoxy-4-oxopiperidine-1-carboxylate (200 g, 872 mmol), were added acetic acid (100 mL), (1R)-1-phenylethanamine (134 mL), dimethyl sulfoxide (5 mL) and 5% platinum-alumina (10 g), and the mixture was heated to 60° C., then the mixture was stirred at that temperature for 8 hours under hydrogen atmosphere (0.3 MPa). The reaction mixture was cooled to room temperature, then platinum-alumina was removed by filtration. Collected platinum-alumina was washed with toluene (1000 mL), and to the combined filtrate were added toluene (1000 mL) and water (1000 mL) then the mixture was adjusted to pH 6.9 by 25% sodium hydroxide aqueous solution. The mixture was stirred and the organic layer was separated. To the separated aqueous layer was added toluene (1000 mL), then the aqueous layer was removed. The organic layer was combined and washed with 2M sodium hydroxide aqueous solution (1000 mL) and 20% sodium chloride aqueous solution (1000 mL), then the organic layer was concentrated under reduced pressure to about 400 mL of volume. To the concentrate, was added acetonitrile (2000 mL), then the mixture was concentrated under reduced pressure to about 400 mL of volume. To the concentrate, were added acetonitrile (1600 mL) and the mixture was heated to 50° C. Then to the mixture was added succinic acid (113.3 g) and the mixture was stirred at that temperature for 30 minutes to yield a slurry mixture. The slurry mixture was cooled to room temperature and stirred for further 1 hour and then the slurry mixture was cooled below 5° C. and stirred for further 1 hour. The solid in the slurry was collected by filtration and the collected solid was washed with cold acetonitrile (600 mL). The solid was dried at 50° C. for over 10 hours to yield 329.3 g (83.4%) of the titled compound as a white solid.

$^1$H NMR (400 MHz, DMSO-$d_6$) δ ppm : 7.42-7.37 (m, 2H), 7.35-7.30 (m, 2H), 7.26-7.21 (m, 1H), 4.16-4.06 (m, 1H), 4.03-3.95 (m, 1H), 3.90-3.64 (m, 1H), 3.46-3.30 (m, 1H), 3.38 (s, 3H), 2.80-2.40 (m, 3H), 2.38 (s, 4H), 1.45-1.35 (m, 2H), 1.38 (s, 9H), 1.26 (d, 3H, J=5.2 Hz)

Step 2: 2-{5-[(3S,4R)-4-Amino-3-methoxypiperidin-1-yl]-1,3,4-thiadiazol-2-yl}propan-2-yl benzoate monopropanoate

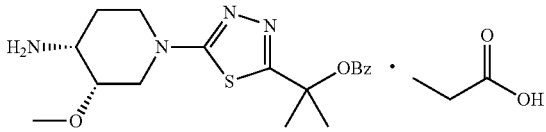

To a suspension of tert-butyl (3S,4R)-3-methoxy-4-{[(1R)-1-phenylethyl]amino}piperidine-1-carboxylate monobutanedioate (200 g, 441.9 mmol) in ethyl acetate (1000 mL), was added 2M sodium hydroxide aqueous solution (1000 mL). The mixture was stirred for a while and aqueous layer was removed, then the organic layer was washed with 20% sodium chloride aqueous solution (1000 mL×2). The organic layer was concentrated under reduced pressure to about 500 mL of volume. To the concentrate, was added methanol (500 mL), then the mixture was concentrated under reduced pressure to about 300 mL of volume. To the concentrate were added methanol (500 mL) and hydrochloric acid (111.9 g), then the mixture was heated to 55° C. The mixture was stirred at that temperature for 4 hours and cooled to room temperature. To the reaction mixture were added water (300 mL) and 25% sodium hydroxide aqueous solution (177 g), then the mixture was stirred and concentrated under reduced pressure to about 500 mL of volume. To the concentrate was added ethyl acetate (700 mL). The mixture was stirred and the organic layer was separated. To the separated aqueous layer was added ethyl acetate (700 mL), then the aqueous layer was removed. The organic layer was combined and washed with 20% sodium chloride aqueous solution (600 mL), then the organic layer was concentrated under reduced pressure to about 500 mL of volume. To the concentrate, was added methanol (500 mL), then the mixture was concentrated under reduced pressure to about 300 mL of volume to yield methanol solution of (3S,4R)-3-methoxy-N-[(1R)-1-phenylethyl]piperidin-4-amine.

To the methanol solution of (3S,4R)-3-methoxy-N-[(1R)-1-phenylethyl]piperidin-4-amine. were added methanol (400 mL) and 5% palladium-carbon (6.0 g), then the mixture was heated to 55° C. The mixture was stirred at that temperature for 6 hours under hydrogen atmosphere (0.3 MPa). The reaction mixture was cooled to room temperature, then palladium-carbon was removed by filtration. Collected palladium-carbon was washed with methanol (200 mL), and the combined filtrate was concentrated under reduced pressure to about 200 mL of volume. To the concentrate, was added acetonitrile (1000 mL), then the mixture was concentrated under reduced pressure to about 200 mL of volume to yield acetonitrile solution of (3S,4R)-3-methoxypiperidin-4-amine.

To the acetonitrile solution of (3S,4R)-3-methoxypiperidin-4-amine, were added 2-(5-bromo-1,3,4-thiadiazol-2-yl)propan-2-yl benzoate (173.5 g), potassium carbonate (73.3 g) and acetonitrile (40 mL) then the mixture was heated to 45° C. and stirred at that temperature for 22 hours. The reaction mixture was cooled to room temperature, and to the mixture, were added ethyl acetate (1000 mL) and water (300 mL). The mixture was stirred and an aqueous layer was removed. After the organic layer was washed with 20% sodium chloride aqueous solution (300 mL), the organic layer was concentrated under reduced pressure to about 600 mL of volume. To the concentrate, were added ethyl acetate (1000 mL) and the mixture was concentrated under reduced pressure to about 1000 mL of volume. To the concentrate were added ethyl acetate (400 mL) and propionic acid (32.7 g), then the mixture was stirred at room temperature for 1 hour to yield a slurry mixture. After heptane (1000 mL) was added thereto, the mixture was stirred for 1 hour. The solid in the slurry was collected by filtration and washed with mixture of ethyl acetate/heptane (1/1, 1000 mL). The collected solid was dried at 50° C. for over 10 hours to yield 144.0 g (72.3%) of the titled compound as a colorless solid.

Step 3: Synthesis of 2-{5-[(3S,4R)-4-{[(4-chloro-5-ethyl-1H-imidazol-2-yl)carbonyl]amino}-3-methoxypiperidin-1-yl]-1,3,4-thiadiazol-2-yl}propan-2-yl benzoate To a suspension of 2-{5-[(3S,4R)-4-amino-3-methoxypiperidin-1-yl]-1,3,4-thiadiazol-2-yl}propan-2-yl benzoate monopropanoate (4.0 g, 8.88 mmol) in a mixture of toluene (20 mL) and acetonitrile (20 mL), was added 20% sodium chloride aqueous solution (12 mL), then pH thereof was adjusted over 11 by 25% sodium hydroxide aqueous solution. The mixture was stirred for a while and aqueous layer was removed, then the organic layer was washed with 20% sodium chloride aqueous solution (12 mL). To the organic layer, were added 4-chloro-5-ethyl-1H-imidazole-2-carboxylic acid (1.70 g, 9.73 mmol) and 1-hydroxybenzotriazole monohydrate (1.36 g), and the mixture was cooled below 5° C. To the mixture, was added 1-ethyl-3-(3-dimethylaminopropyl)carbodiimide monohydrochloride (2.55 g), and the mixture was stirred at that temperature for 1.5 hour. To the mixture, were added toluene (20 mL) and water (20 mL), and after the mixture was stirred, the aqueous layer was removed. The organic layer was washed with water (20 mL), and the organic layer was concentrated under reduced pressure. The concentrate of 2-{5-[(3S,4R)-4-{[(4-chloro-5-ethyl-1H-imidazol-2-yl)carbonyl]amino}-3-methoxypiperidin-1-yl]-1,3,4-thiadiazol-2-yl}propan-2-yl benzoate was used for further modification process.

Biological Assay

A number of different assays can be utilized. In addition to assays mentioned hereinafter, one of ordinary skill in the art will know of other assays that can be utilized and can modify an assay for a particular application. Such assays and modification thereon are within the spirit and scope of the present invention.

Test Example 1

Method for Testing Inhibitory Activity of Enzymes
(a) The ATP hydrolysis activity of GyrB and ParE was measured by correlating an ATP consumption with a relative light unit, using a light emitting Kinase-Glo® reagent in an ATP amount-dependent manner.

In the ATP hydrolysis assay wherein an ATP consumption is correlated with a relative light unit using a light emitting Kinase-Glo® reagent in an ATP amount-dependent manner, solutions of the test compound serially 4-fold diluted in dimethylsulfoxide:methanol (9:1) were added at a final concentration of 2% (v/v). After mixing with an enzyme at a final concentration of 40 U/mL (in the case of GyrB or ParE of *Streptococcus pneumoniae* or ParE of *Haemophilus infuenzae*) or an enzyme at a final concentration of 20 U/mL (in the case of GyrB of *Haemophilus infuenzae*), 100 mM Tris-HCl (pH 7.5), 150 mM potassium chloride (KCl), 5 mM magnesium chloride ($MgCl_2$), 10 mM DTT, 2 μM ATP and 50 μg/mL BSA were added thereto at the final concentration and mixed. The reaction solution was incubated at 30° C. for 2 hours (2.5 hours in the case of GyrB of *Haemophilus infuenzae*). After completion of the reaction, $^{KinaseGlo}$® reagent was added in an amount equal to the reaction solution, mixed and reacted at room temperature for 10 minutes, and then assayed for a relative light unit. As a control with an inhibition rate of 0%, the reaction was carried out by adding a dimethylsulfoxide:methanol (9:1) solution, and as a control with an inhibition rate of 100%, the reaction with a sterile water added in place of the enzyme was carried out. The activity rate (%) was calculated by dividing the value obtained by subtracting the relative light unit of each reaction from the relative light unit of the control with an inhibition rate of 100% by the value obtained by subtracting the relative light unit of the control with an inhibition rate of 0% from the relative light unit of the control with an inhibition rate of 100%, and the activity rate was subtracted from 100 to determine an ATP hydrolysis inhibition rate (%). The 50% inhibition concentration ($IC_{50}$) was calculated from the reaction performed in the presence of 8 different concentrations of the test compound.

All compounds disclosed herein had an $IC_{50}$ of less than 0.05 μg/mL for GyrB of *Streptococcus pneumoniae* or *Haemophilus influenzae*.

(b) The potential of the compounds of the present invention against DNA gyrase was measured by inhibition of supercoiling activity of *Clostridium difficile* DNA gyrase. DNA supercoiling assays (30 μL reaction) were performed in a buffer containing 15 mM Tris-HCl pH 7.5, 13% glycerol, 6 mM $MgCl_2$, 0.1 mg/mL BSA, 70 mM KCl, 1 mM dithioerythritol, 400 ng of DNA substrate (relaxed pBR322 DNA) and different concentrations of test compounds and/or standards. The dilutions of test compounds and standards were prepared in 20% dimethylsulfoxide (DMSO) and added 3 μL/reaction. The reaction was started by adding 2 μL amounts of *Clostridium difficile* DNA gyrase into the reaction mixtures and reactions were allowed to proceed for 60 minutes at 37° C. A reaction was carried out by adding 3 μL of 20% DMSO instead of test compound as full reaction control, and another reaction was carried out by adding sterile water instead of the enzyme as no reaction control.

Reactions were stopped by the addition of 5 μL of 6×loading dye and were analyzed by electrophoresis through 1.0% agarose gels with 1×TAE running buffer. Gels were run at 60 V for 3 hours, stained with EtBr, and visualized by Gel Doc system (BioRad). Intensity of the supercoiled DNA bands was quantified, and the $IC_{50}$ of *Clostridium difficile* DNA gyrase was calculated using Graph Pad Prism.

All compounds disclosed herein had an $IC_{50}$ of less than 0.05 μg/mL for *Clostridium difficile* DNA gyrase, for example, compound Nos. 1, 2, 4, 5, 10 and 11 had an $IC_{50}$ of 0.0037, 0.0200, 0.0060, 0.0090, 0.0270 and 0.0120 μg/mL, respectively.

Test Example 2

(a) Method of Testing Susceptibility of Bacteria

The antibacterial activity of the compounds of the present invention was tested by the broth microdilution method. The assay was carried out according to the CLSI guidelines for managing the procedures of susceptibility tests: "M7-A7 Methods for Dilution Antimicrobial Susceptibility Tests for Bacteria That Grow Aerobically; Approved Standard-Seventh Edition (2006)".

Test strains were grown on appropriate agar plates overnight. A broth containing the test compound diluted serially 2-fold and diluents were dispensed at 100 μL to each well of a 96-well microplate. As a growth control, a well with a broth not containing the test compound was also prepared. Colonies grown on the plates were suspended in saline, adjusted to 0.5 McFarland ($OD_{625}$=0.08 to 0.10) using a colorimeter, and then diluted 10-fold with saline. The bacterial suspension was inoculated at 4 μL into each well of the microplate using a bacterial suspension inoculation apparatus. The inoculated microplate was incubated at 35° C. overnight (about 20 hours). The growth condition was observed by the naked eye, and the minimum concentration to inhibit bacterial proliferation was defined as a minimum inhibitory concentration (MIC).

The MICs of compounds disclosed herein for *E. faecium*, *Streptococcus pneumoniae* and *Haemophilus influenzae* are shown in Table 2, while for *S. aureus* in Table 3.

TABLE 2

| | [MIC, μg/mL] | | |
|---|---|---|---|
| Compound No. | *E. faecium* ATCC 29212 | *Streptococcus pneumoniae* ATCC 49619 | *Haemophilus influenzae* ATCC 49247 |
| 1 | 0.25 | 0.25 | 2 |
| 2 | 0.25 | 0.25 | 0.5 |
| 4 | 0.25 | 0.25 | 1 |
| 5 | 0.25 | 0.25 | 1 |

(b) Method of Testing Susceptibility of *Clostridium Difficile*

The antibacterial activity of the compounds of the present invention against *Clostridium difficile* clinical isolates was tested by the agar dilution method. The assay was carried out according to the CLSI guidelines for managing the procedures of susceptibility tests "M11-A8, Methods for Antimicrobial Susceptibility Testing of Anaerobic Bacteria; Approved Standard-Eighth Edition. CLSI document (2012)".

The test strains were spread on supplemented Brucella agar (SBA) plates and grown at 36° C. under anaerobic condition for 42 to 48 hours. The test compound dilutions were prepared with Brucella broth and SBA plates containing dilution of test compound were prepared. As an anaerobic growth control, plates not containing the test compound were also prepared. Colonies grown on plates were suspended with Brucella broth to adjust the turbidity to 0.5 McFarland using a densitometer. Suspension (1-2 µL) of the test strains was inoculated onto each agar surface by using a bacterial suspension inoculation apparatus. After anaerobic incubation at 36° C. for 42 to 48 hours, absence and presence of growth of each strain were examined with unaided eye. The MIC was determined at which a marked reduction occurs in the appearance of growth on the test plate as compared to that of growth on the anaerobic control plates.

The MICs of compounds disclosed herein for *Clostridium difficile* are as shown in Table 3.

TABLE 3

| | [MIC, µg/mL] | |
|---|---|---|
| Compound No. | *S. aureus* ATCC 29213 | *Clostridium difficile* ATCC 43255 |
| 1 | 0.5 | 0.03 |
| 2 | 0.25 | 0.06 |
| 3 | 0.5 | 0.125 |
| 4 | 0.5 | 0.06 |
| 5 | 0.5 | 0.125 |
| 6 | 0.5 | 0.125 |
| 7 | 0.5 | 0.125 |
| 8 | 4 | 0.125 |
| 9 | 4 | 0.125 |
| 10 | 1 | 0.06 |
| 11 | 1 | 0.06 |

Test Example 3

Method of Testing Cytotoxicity

Liver cell line, HepG2, was cultured into each well of a 96-well microplate at 5000 cells per well. These cells were treated with test compounds or DMSO (1%) for 24 hours, at culture conditions (37° C., 5% $CO_2$). Amphotericin B and Aspirin were included as positive control and negative control, respectively. Post compound treatment, cells were washed and incubated with WST-8 solution in serum free media for 2 hours, at culture conditions. Cell plate was read in Infinite M-1000 (Tecan), an automated plate reader, for absorbance measurement at 450 nm. Absorbance data was processed by 'Blank' subtraction and value of negative control (Aspirin in this case) is also taken into account for each concentration. Reduction in cell viability was calculated and $IC_{50}$ of these compounds have been calculated for ease of comparison.

All compounds of the present invention had $IC_{50}$ of more than 100 µg/mL.

Test Example 4

Method of Testing Solubility in Water

A 10 mmol/L solution of the test compound was prepared in DMSO and dispensed 100 µL of 10 mmol/L DMSO stock solutions into labeled glass tubes in duplicate, one for Japanese Pharmacopeia First Fluid (JP1) and second for Japanese Pharmacopeia Second Fluid (JP2). After evaporation of DMSO from each tube, 500 µL of JP1 and JP2 fluid were added in each tube, respectively. These tubes were sonicated for 1 minute and placed on shaker for 30 minutes with an interval of 30 seconds at every 5 minute. Tubes were placed in dark at room temperature for 1 hour and solution was filtered through membrane filter. The filtrate was diluted 2-fold and 10-fold. The resulting test solutions was analyzed and quantified against the standards using UPLC (standard preparation—10 mmol/L solution in DMSO is serially diluted with 50% aqueous acetonitrile solution to prepare 2 solutions; 100 µmol/L standard solution and 5 µmol/L standard solutions).

TABLE 4

| | [Solubility, µg/mL] | |
|---|---|---|
| Compound No. | JP1 | JP2 |
| 2 | 706 | 256 |
| 4 | 612 | 304 |
| 5 | 680 | 359 |
| 7 | — | 611 |
| 8 | 728 | 125 |
| 9 | 862 | 220 |
| 10 | 887 | 429 |
| 11 | 884 | 264 |

Test Example 5

Method for Testing Oral Bioavailability (BA) in Rats and Monkeys

To SD male rats (7 week-old) fasted overnight, a solution of the test compound Captisol® was administered into the jugular vein (3 animals) and a solution of Lutrol® F68 was administered orally (3 animals). The dose of the test compounds was 2 mg/kg body weight of the rat for both administration routes. The amount of Captisol® used was 0.36 mg/kg body weight of the rat. The amount of Lutrol® F68 used was 0.02 mg/kg body weight of the rat. The BA value was calculated by the formula below using the integration value (AUCiv(0-∞)) of the blood concentration extrapolated from time 0 to infinity after administration of both test compounds.

To male Macaca fascicularis (3 or 4 year-old) fasted overnight, a solution of the test compound Captisol® was administered into the jugular vein (3 animals) and a solution of Lutrol® F68 was orally administered (3 animals). The dose of both test compounds was 1 mg/kg body weight of the monkey. The amount of Captisol® used was 0.18 mg/kg body weight of the monkey. The amount of Lutrol® F68 used was 0.02 mg/kg body weight of the monkey. The BA value was calculated by the formula below using the integration value (AUCiv(0-∞)) of the blood concentration extrapolated from time 0 to infinity after administration of both test compounds.

BA(%)=[[(AUCpo(0-∞))/(dose po)]/[(AUCiv(0-∞))/(dose iv)]]×100

The greater a BA value of the compound shown, the higher the oral bioavailability is.

The exemplified compounds have good bioavailability (%) in Rat and Monkey, for instance, compound Nos. 2, 3, and 5 have 98, 51 and 60 in Rat and compounds Nos. 2, 3, 4 and 5 have 85, 100, 92 and 100 in Monkey, respectively.

Test Example 6

(a) Method for Testing Therapeutic Effect Using Mouse Lung Infection Model by *Streptococcos Pneumoniae*

The *Streptococcos pneumoniae* strain cultured using Todd Hewitt broth was harvested by centrifugation, suspended in saline, and nasally inoculated into CBA/JNCrlj mice (3- to 6-week-old, Charles River Laboratories Japan Inc.: 4 mice per group) under anesthesia with a ketamine-xylazine mixture. The drug was administered to the mice twice at an interval of 6 to 10 hours. The number of bacteria in the lung was determined in the non-treated group immediately before initial administration of the drug (pre-control) and in the non-treated group (post-control) and the drug-administered group on the next day of administration of the drug and infection. A change in the number of bacteria in the lung was used as an index of therapeutic effect.

All compounds of Examples exhibited a therapeutic effect in this test method, for example, FIG. 1 depicts the values for compound Nos. 1 to 5.

(b) Method for Testing Therapeutic Effect Using Neutropenic Mouse Thigh or Calf Muscle Infection Model After culture in broth medium (i) suitable diluent of a bacterial suspension of the *Staphylococcus aureus* strain, or (ii) equivalent mixture of suitable diluent of a bacterial suspension of the *Enterococcus faecium* strain and a 10% mucin suspension were used as the inoculum. The bacterial suspension was inoculated under anesthesia with a ketamine-xylazine mixture into the thigh or calf muscle of Swiss albino mice or ICR mice (4- to 6-week-old) compromised by the cyclophosphamide administration. The drug was administered to the mice 1 to 8 times at an interval of 3 to 24 hours. The number of bacteria in the thigh or calf muscle was counted for the non-treated group immediately before initial administration of the drug (pre-control), for the non-treated group (post-control) and for the drug-administered group on the next day of administration of the drug and infection. A change in the number of bacteria in the thigh or calf muscle was used as an index of therapeutic effect.

The exemplified Compound Nos. 2, 4 and 5 exhibited the therapeutic effect against *Staphylococcus aureus* equivalent to or higher than linezolid by this test method.

(c) Method for Testing Therapeutic Effect Using Mouse Systemic Infection Model

After suitably diluting a bacterial suspension of 1) the *Staphylococcus aureus* strain, 2) the *Streptococcus pneumoniae* strain, and 3) the *Enterococcus faecium* strain cultured using liquid medium, a 10% mucin suspension was added in the equivalent amount, and intraperitoneally inoculated into Swiss albino mice or ddY mice (4- to 6-week-old). The drug was administered to this infection model twice at an interval of 4 to 6 hours. The survival rates on day 7 of the non-treated group and the drug-administered group were confirmed.

(d) Method for Testing Therapeutic Effect in Hamster CDI Model

The in vivo efficacy of test compounds were evaluated in a hamster CDI model caused by *Clostridium difficile* 2009155, a NAP1/027 strain. Syrine hamsters (6-8-weeks old) were primed with a single subcutaneous injection of clindamycin (30 mg/kg) 1-5 days prior to infection. Hamsters were infected by oral gavage with 1 ml of spore suspension ($2 \times 10^4$-$3 \times 10$) prepared in PBS. The drug was administered to the hamsters 6 hours post infection by oral or subcutaneous route at an interval of 24 hours for 5 days. The death and survival of the non-treated group and the drug-administered group were recorded once daily for 35 days.

All compounds disclosed herein exhibited therapeutic effect in this test method, for example, compound Nos. 1, 2, 5, 10 and 11 exhibited 100% survival on day 35 at 0.3 mg/kg/day by oral route.

Test Example 7

Method of Testing Susceptibility of *P. Acnes*

The antibacterial activity of the compounds of the present invention against *P. acnes* clinical isolates was tested by the agar dilution method. The assay was carried out according to the CLSI guidelines document (Clinical and Laboratory Standards Institute, 2012 & 2016). The test strains were spread on supplemented Brucella agar (SBA) plates and grown for 42 to 48 hours at 36° C. under anaerobic condition. The test compound dilutions were prepared with Brucella broth and SBA plates containing dilution of test compound were prepared. As an anaerobic growth control and to check the aerobic contamination, plates not containing the test compound were also prepared. Colonies grown on plates were suspended with Brucella broth to adjust the turbidity to 0.5 McFarland using a densitometer. Suspension (1-2 μL) of the test strains was inoculated onto each agar surface by using a bacterial suspension inoculation apparatus (multipoint inoculator). After anaerobic incubation for 42 to 48 hours at 36° C., absence and presence of growth of each strain on growth control plates and test compounds plate were examined with unaided eye. The MIC was determined at which a marked reduction occurs in the appearance of growth on the test plate as compared to that of growth on the anaerobic control plates.

TABLE 5

| | [MIC, μg/mL] | | | |
|---|---|---|---|---|
| Compound No. | *P. acnes* ATCC 6921 | *P. acnes* ATCC 6523 | *P. acnes* IHMA 103740 | *P. acnes* IHMA 775486 |
| 2 | 0.125 | 0.125 | 0.125 | 0.125 |
| 6 | 0.125 | 0.125 | 0.25 | 0.25 |
| 8 | 0.25 | 0.25 | 0.25 | 0.25 |
| 9 | 0.125 | 0.125 | 0.125 | 0.125 |
| 10 | 0.125 | 0.125 | 0.125 | 0.125 |

Test Example 8

Method of Testing Susceptibility of *N. Gonorrhoeae*

The antibacterial activity of the compounds of the present invention against *N. gonorrhoeae* clinical isolates was tested by the agar dilution method [*Clinical and Laboratory Standards Institute*, 2016]. The test strains were spread on chocolate agar plates and grown for 20-24 h at 36° C. in 5% carbon dioxide. The test compound dilutions were prepared with broth and agar MIC plates were prepared using GC agar base supplemented with haemoglobin and 1% IsoVitaleX plates. As growth control plates not containing the test compound were also prepared. Colonies grown on plates were suspended with broth to adjust the turbidity to 0.5 McFarland using a densitometer. Suspension (1-2 μL) of the test strains was inoculated onto each agar surface by using a bacterial suspension inoculation apparatus (multipoint inoculator). After aerobic incubation for 20-24 h at 36° C. in 5% carbon dioxide, absence and presence of growth of each strain on growth control plates and test compounds plate were examined with unaided eye. The MIC was determined at which a marked reduction occurs in the appearance of growth on the test plate as compared to that of growth on the aerobic control plates.

Compounds disclosed herein exhibited very good MICs, for example, compound Nos. 2 and 10 had MICs of 0.25 and 0.125, respectively.

The invention claimed is:

1. A compound represented by formula (I), or a tautomer, or stereoisomers, or a pharmaceutically acceptable salt thereof;

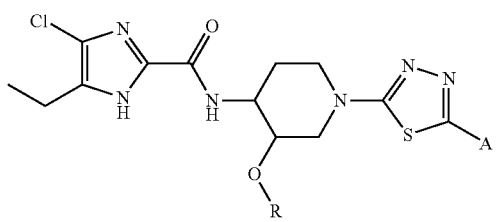

wherein R represents (C$_1$-C$_3$) alkyl, and
A represents the following formulae:

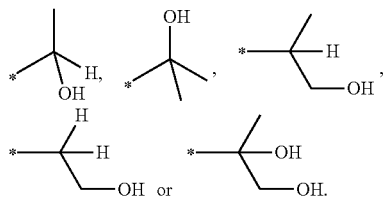

2. The compound, a tautomer, or a pharmaceutically acceptable salt thereof according to claim 1, wherein the compound of formula (I) has following structure:

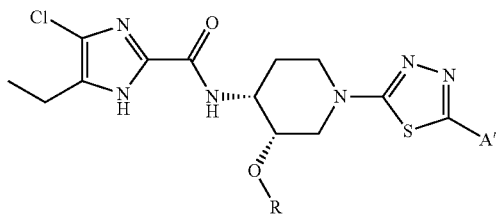

wherein R represents (C$_1$-C$_3$) alkyl, and
A' represents following formulae:

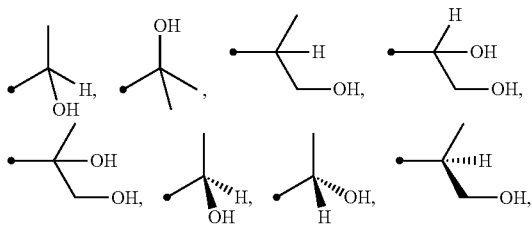

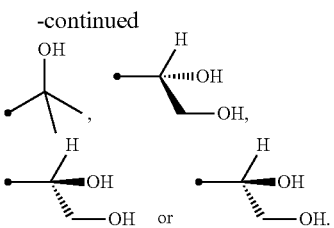

3. The compound, a stereoisomer, a tautomer, or a pharmaceutically acceptable salt thereof according to claim 1, wherein R represents methyl or ethyl.

4. The compound according to claim 1, wherein the compound is selected from:
4-Chloro-N-{(3S,4R)-3-ethoxy-1-[5-(1-hydroxyethyl)-1,3,4-thiadiazol-2-yl]piperidin-4-yl}-5-ethyl-1H-imidazole-2-carboxamide,
4-Chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide,
4-Chloro-5-ethyl-N-{(3S,4R)-1-[5-(1-hydroxyethyl)-1,3,4-thiadiazol-2-yl]-3-methoxypiperidin-4-yl}-1H-imidazole-2-carboxamide,
4-Chloro-5-ethyl-N-[(3S,4R)-1-{5-[(1R)-1-hydroxyethyl]-1,3,4-thiadiazol-2-yl}-3-methoxypiperidin-4-yl]-1H-imidazole-2-carboxamide,
4-Chloro-5-ethyl-N-[(3S,4R)-1-{5-[(1S)-1-hydroxyethyl]-1,3,4-thiadiazol-2-yl}-3-methoxypiperidin-4-yl]-1H-imidazole-2-carboxamide,
4-Chloro-5-ethyl-N-{(3S,4R)-1-[5-(1-hydroxypropan-2-yl)-1,3,4-thiadiazol-2-yl]-3-methoxypiperidin-4-yl}-1H-imidazole-2-carboxamide,
4-Chloro-N-{(3S,4R)-3-ethoxy-1-[5-(2-hydroxypropan-2-yl)-1,3,4-thiadiazol-2-yl]piperidin-4-yl}-5-ethyl-1H-imidazole-2-carboxamide,
4-Chloro-N-[(3S,4R)-1-{5-[(1S)-1,2-dihydroxyethyl]-1,3,4-thiadiazol-2-yl}-3-methoxypiperidin-4-yl]-5-ethyl-1H-imidazole-2-carboxamide,
4-Chloro-N-[(3S,4R)-1-{5-[(1R)-1,2-dihydroxyethyl]-1,3,4-thiadiazol-2-yl}-3-methoxypiperidin-4-yl]-5-ethyl-1H-imidazole-2-carboxamide,
4-Chloro-N-[(3S,4R)-1-{5-[(2R)-1,2-dihydroxypropan-2-yl]-1,3,4-thiadiazol-2-yl}-3-methoxypiperidin-4-yl]-5-ethyl-1H-imidazole-2-carboxamide,
4-Chloro-N-[(3S,4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamide, or
a tautomer, or a pharmaceutically acceptable salt thereof.

5. The compound according to claim 4, wherein 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide is selected from Form I, or Form II, characterized by powder x-ray diffraction (XRD) spectrum (CuK, λ=1.54 Å), wherein Form I has characteristic peaks 2θ (d) at 8.38 (10.54), 10.90 (8.11), 14.50 (6.08), 14.94 (5.92), 19.82 (4.48), and 24.68 (3.60), and wherein Form II has characteristic peaks 2θ (d) at 13.20 (6.67), 14.94 (5.92), 16.08 (5.51), 17.76 (4.99), 19.46 (4.56), and 24.82 (3.58).

6. The compound according to claim 4, wherein 4-chloro-N-[(3S,4R)-1-{5-[(2R)-1,2-dihydroxypropan-2-yl]-1,3,4-thiadiazol-2-yl}-3-methoxypiperidin-4-yl]-5ethyl-1H-imidazole-2-carboxamide is crystalline solid, designated as Form A, characterized by powder x-ray diffraction (XRD) spectrum (CuK, λ=1.54 Å), wherein Form A has characteristic peaks 2θ (d) at 15.70 (5.63), 17.06 (5.19), 19.10 (4.64), and 21.92 (4.05).

7. The compound according to claim 4, wherein 4-chloro-N-[(3S,4R)-1-{5-[(2S)-1,2-dihydroxypropan-2-yl]-1,3,4-thiadiazol-2-yl}-3-methoxypiperidin-4-yl]-5-ethyl-1H-imidazole-2-carboxamide is crystalline solid, designated as Form B, characterized by powder x-ray diffraction (XRD) spectrum (CuK, λ=1.54 Å), wherein Form B has characteristic peaks 2θ (d) at 13.13 (6.73), 14.27 (6.20), and 19.10 (4.64).

8. A pharmaceutical composition comprising a therapeutically effective amount of a compound, a stereoisomer, a tautomer, or a pharmaceutically acceptable salt thereof according to claim 1, as its active ingredient.

9. A method for the treatment of a bacterial infectious disease treatable by inhibiting a DNA gyrase GyrB subunit and/or a topoisomerase IV ParE subunit, comprising administering to a subject in need thereof a therapeutically effective amount of a compound of claim 1, a tautomer, or pharmaceutically acceptable salt thereof.

10. The method according to claim 9, wherein said bacterial infectious disease is caused by Gram-positive bacteria selected from genus *Staphylococcus, Streptococcus, Enterococcus, Clostridium, Bacillus, Corynebacterium*, or *Listeria* species.

11. The method according to claim 9, wherein said bacterial infectious disease is caused by resistant bacteria selected from methicillin-resistant *Staphylococcus aureus*, penicillin-resistant *Streptococcus pneumoniae*, or vancomycin-resistant *Enterococcus*.

12. The method according to claim 9, wherein said bacterial infectious disease is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, *Clostridium difficile* infections, acne vulgaris, gonorrhea, gas gangrene, food poisoning, tetanus, botulism, diarrhea, pseudomembranous colitis, toxic mega colon, or perforation of colon.

13. The method according to claim 9, wherein said bacterial infectious disease is selected from community-acquired respiratory infections, hospital-acquired infections, or *Clostridium difficile* infections.

14. The method according to claim 9, wherein the compound is represented by

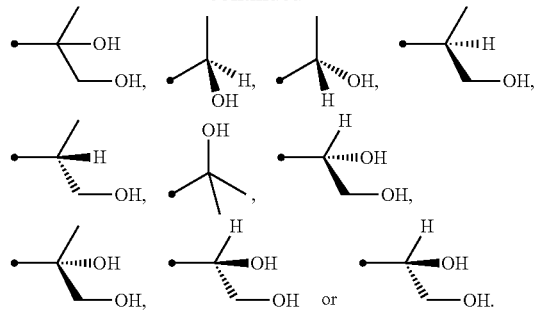

wherein R represents (C$_1$-C$_3$) alkyl, and
A' represents following formulae:

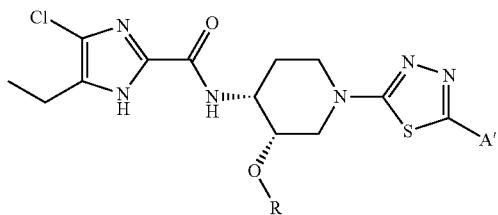

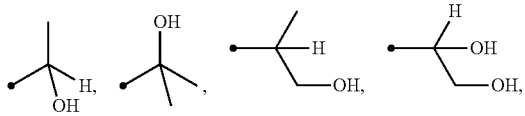

15. A method for inhibiting a DNA gyrase GyrB subunit and/or a topoisomerase IV ParE subunit in a subject comprising administering to a subject an amount of a compound of claim 1, a tautomer, or pharmaceutically acceptable salt thereof, effective to inhibit the DNA gyrase GyrB subunit and/or the topoisomerase IV ParE subunit.

16. A ⅔ hydrate of 4-chloro-5-ethyl-N-{(3S,4R)-1-[5-(2-hydroxypropan-2-yl)-1,3,4-thiadiazol-2-yl]-3-methoxypiperidin-4-yl}-1H-imidazole-2-carboxamide, or a pharmaceutically acceptable salt thereof.

17. A pharmaceutical composition comprising a therapeutically effective amount of a compound, a tautomer, or a pharmaceutically acceptable salt thereof according to claim 16, as its active ingredient.

18. A method for the treatment of a bacterial infectious disease treatable by inhibiting a DNA gyrase GyrB subunit and/or a topoisomerase IV ParE subunit, comprising administering to a subject in need thereof a therapeutically effective amount of a compound of claim 16, a tautomer, or pharmaceutically acceptable salt thereof.

19. The method according to claim 18, wherein said bacterial infectious disease is caused by Gram-positive bacteria selected from genus *Staphylococcus, Streptococcus, Enterococcus, Clostridium, Bacillus, Corynebacterium*, or *Listeria* species.

20. The method according to claim 18, wherein said bacterial infectious disease is caused by resistant bacteria selected from methicillin-resistant *Staphylococcus aureus*, penicillin-resistant *Streptococcus pneumoniae*, or vancomycin-resistant *Enterococcus*.

21. The method according to claim 18, wherein said bacterial infectious disease is selected from pimples, impetigo, boils, cellulitis folliculitis, furuncles, carbuncles, scalded skin syndrome, pneumonia, meningitis, osteomyelitis, endocarditis, toxic shock syndrome, bronchitis, rhinitis, acute sinusitis, otitis media, conjunctivitis, bacteremia, sepsis, osteomyelitis, septic arthritis, peritonitis, pericarditis, cellulitis, brain abscess, urinary tract infections, Clostridium difficile infections, acne vulgaris, gonorrhea, gas gangrene, food poisoning, tetanus, botulism, diarrhea, pseudomembranous colitis, toxic mega colon, or perforation of colon.

22. The method according to claim 18, wherein said bacterial infectious disease is selected from community-acquired respiratory infections, hospital-acquired infections, or *Clostridium difficile* infections.

23. A method for inhibiting a DNA gyrase GyrB subunit and/or a topoisomerase IV ParE subunit in a subject comprising administering to a subject an amount of a compound of claim 16, a tautomer, or pharmaceutically acceptable salt thereof, effective to inhibit the DNA gyrase GyrB subunit and/or the topoisomerase IV ParE subunit.

* * * * *

UNITED STATES PATENT AND TRADEMARK OFFICE
CERTIFICATE OF CORRECTION

PATENT NO.        : 10,399,968 B2
APPLICATION NO.   : 15/764264
DATED             : September 3, 2019
INVENTOR(S)       : M. K. Khera et al.

Page 1 of 1

It is certified that error appears in the above-identified patent and that said Letters Patent is hereby corrected as shown below:

On the Title Page

| Item (57) | Abstract | "exhibit" should read --exhibits-- |
| Column 2 | Line 3 | |

| Item (57) | Abstract | "an" should read --and-- |
| Column 2 | Line 5 | |

In the Claims

| Column 74 | Line 11 | Delete "a tautomer," |
| (Claim 3, Line 1) | | |

Signed and Sealed this
Twenty-eighth Day of July, 2020

Andrei Iancu
*Director of the United States Patent and Trademark Office*